US010787515B2

United States Patent
Keefe et al.

(10) Patent No.: US 10,787,515 B2
(45) Date of Patent: Sep. 29, 2020

(54) ANTI-FLT-1 ANTIBODIES FOR TREATING DUCHENNE MUSCULAR DYSTROPHY

(71) Applicant: SHIRE HUMAN GENETIC THERAPIES, INC., Lexington, MA (US)

(72) Inventors: Dennis Keefe, Lexington, MA (US); Hans De Haard, Zwijnaarde (BE); Natalie De Jonge, Zwijnaarde (BE); Sofie Gabriels, Zwijnaarde (BE)

(73) Assignee: Shire Human Genetic Therapies, Inc., Lexington, MA (US)

( * ) Notice: Subject to any disclaimer, the term of this patent is extended or adjusted under 35 U.S.C. 154(b) by 77 days.

(21) Appl. No.: 15/564,976

(22) PCT Filed: Apr. 7, 2016

(86) PCT No.: PCT/US2016/263520
§ 371 (c)(1),
(2) Date: Oct. 6, 2017

(87) PCT Pub. No.: WO2016/164528
PCT Pub. Date: Oct. 13, 2016

(65) Prior Publication Data
US 2018/0072806 A1 Mar. 15, 2018

Related U.S. Application Data

(60) Provisional application No. 62/144,251, filed on Apr. 7, 2015, provisional application No. 62/307,645, filed on Mar. 14, 2016.

(51) Int. Cl.
*C07K 16/28* (2006.01)
*A61K 39/395* (2006.01)
*A61K 39/00* (2006.01)

(52) U.S. Cl.
CPC .... *C07K 16/2863* (2013.01); *A61K 39/39566* (2013.01); *A61K 2039/505* (2013.01); *C07K 2317/22* (2013.01); *C07K 2317/24* (2013.01); *C07K 2317/33* (2013.01); *C07K 2317/34* (2013.01); *C07K 2317/50* (2013.01); *C07K 2317/515* (2013.01); *C07K 2317/55* (2013.01); *C07K 2317/565* (2013.01); *C07K 2317/569* (2013.01); *C07K 2317/70* (2013.01); *C07K 2317/74* (2013.01); *C07K 2317/76* (2013.01); *C07K 2317/92* (2013.01); *C07K 2317/94* (2013.01)

(58) Field of Classification Search
CPC .......... C07K 16/2863; C07K 2317/515; C07K 2317/565; C07K 2317/22; C07K 2317/55; C07K 2317/569; C07K 2317/33; C07K 2317/24; A61K 2039/505
See application file for complete search history.

(56) References Cited

U.S. PATENT DOCUMENTS 9,957,324 B2 * 5/2018 Josiah ................ C07K 16/2866
2018/0312593 A1 11/2018 Josiah et al.

FOREIGN PATENT DOCUMENTS

| WO | WO-2006/055809 A2 | 5/2006 |
| WO | WO-2012/109282 A2 | 8/2012 |
| WO | WO-2014/117160 A1 | 7/2014 |
| WO | WO-2014/150314 A1 | 9/2014 |

OTHER PUBLICATIONS

Ennen et al., "Vascular-targeted therapies for Duchenne muscular dystrophy", Skeletal Muscle. 3(1):9 (2013).
International Search Report and Written Opinion for PCT/US14/13402, dated Jul. 31, 2014 (15 pages).
International Search Report and Written Opinion for PCT/US16/26352, dated Oct. 13, 2016 (20 pages).
Messina et al., "VEGF overexpression via adeno-associated virus gene transfer promotes skeletal muscle regeneration and enhances muscle function in mdx mice", The Faseb Journal. 21(13):3737-3746 (2007).
Sanz et al., "Antibodies and gene therapy: teaching old 'magic bullets' new tricks", Trends in Immunology. 25(2):85-91 (2004).
Shibuya et al., "Differential Roles of Vascular Endothelial Growth Factor Receptor-1 and Receptor-2 in Angiogenesis", Journal of Biochemistry and Molecular Biology. 39(5):469-478 (2006).
Shimizu-Motohashi and Asakura: "Angiogenesis as a novel therapeutic strategy for Duchenne muscular dystrophy through decreased ischemia and increased satellite cells", Frontiers in Physiology. 5(50):1-17 (2014).
Verma et al., "Flt-1 haploinsufficiency ameliorates muscular dystrophy phenotype by developmentally increased vasculature in mdx mice", Human Molecular Genetics. 19(21): 4145-4159 (2010).
Wu et al., "Anti-Vascular Endothelial Growth Factor Receptor-1 Antagonist Antibody as a Therapeutic Agent for Cancer", Clinical Cancer Research. 12(21):6573-6584 (2006).

* cited by examiner

*Primary Examiner* — Ruixiang Li
(74) *Attorney, Agent, or Firm* — Proskauer Rose LLP; Fangli Chen; Julio J. Mendez

(57) ABSTRACT

The present invention provides, among other things, anti-Flt-1 antibodies and methods for treating muscular dystrophy, in particular, Duchenne muscular dystrophy (DMD). In some embodiments, a method according to the present invention includes administering to an individual who is suffering from or susceptible to DMD an effective amount of an anti-Flt-1 antibody or antigen-binding protein thereof such that at least one symptom or feature of DMD is reduced in intensity, severity, or frequency, or has delayed onset.

11 Claims, 47 Drawing Sheets
Specification includes a Sequence Listing.

Isotype Control

Commercial control Ab

13B4

10G12

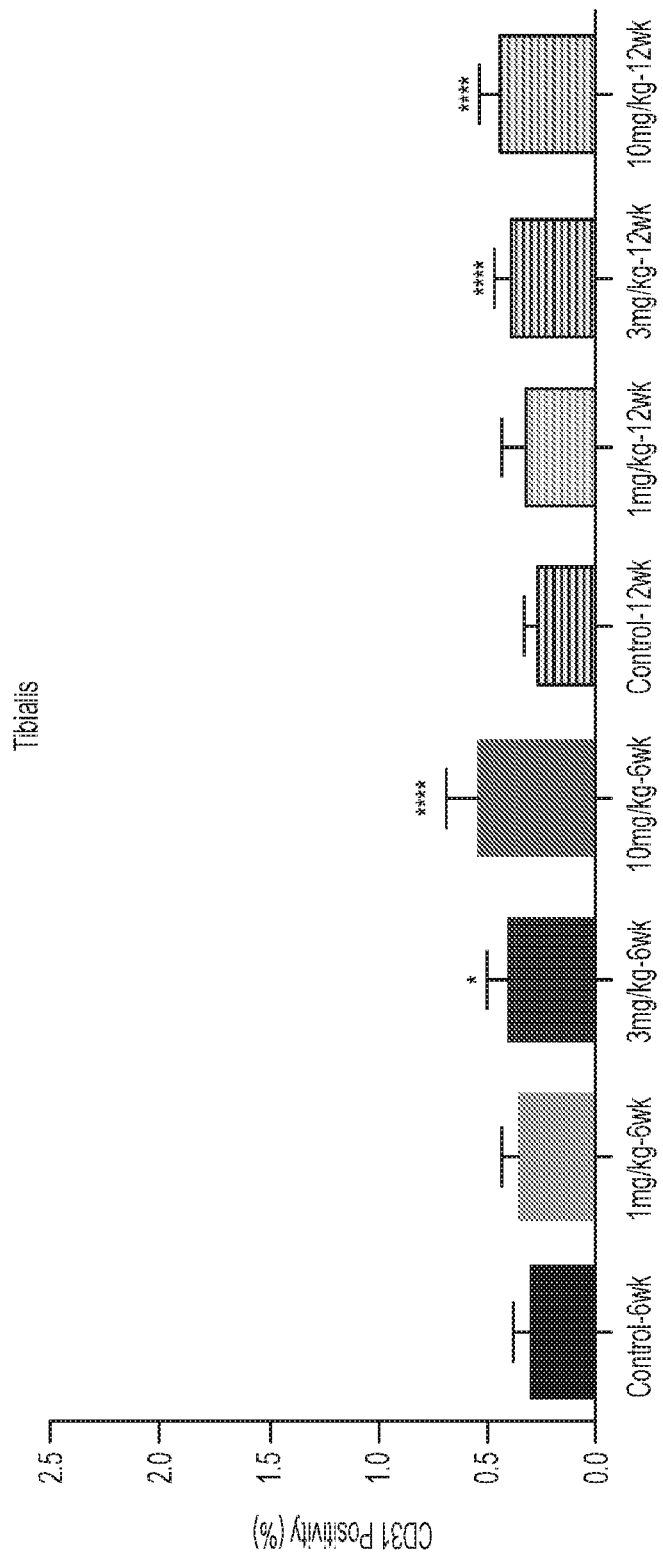

SEQUENCE LISTING

```
<160> NUMBER OF SEQ ID NOS: 111

<210> SEQ ID NO 1
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 1

Ser Tyr Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 2

Asp Tyr Ser Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 3

Asp Tyr Ser Ala Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Oligopeptide

<400> SEQUENCE: 4

Asp Tyr Ser Leu Ser
1               5
```

-continued

```
<210> SEQ ID NO 5
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 5

Ala Ile Ser Gly Ser Gly Gly Ser Thr Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 6

Ala Ile Ser Trp Asn Gly Asp Ser Thr Tyr Tyr Ala Glu Ser Met Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 7

Ala Ile Ser Trp Asn Gly Asp Ser Thr Tyr Tyr Ala Glu Ser Leu Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 8

Ala Ile Ser Trp Asn Gly Asp Ser Thr Tyr Tyr Ala Glu Ser Ala Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 9

Ala Ile Ser Trp Asn Gly Asp Ser Thr Tyr Tyr Ala Glu Ser Val Lys
1               5                   10                  15

Gly

<210> SEQ ID NO 10
<211> LENGTH: 17
<212> TYPE: PRT
<213> ORGANISM: Artificial Sequence
```

<220> FEATURE:
<223> OTHER INFORMATION: Synthetic Oligopeptide

<400> SEQUENCE: 10

Ala Ile Thr Trp Ser Gly Asp Ser Thr Tyr Tyr Ala Glu Ser Val Lys
1               5                   10                  15
Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 11

Ala Ile Ser Trp Ser Gly Asp Ser Thr Tyr Tyr Ala Glu Ser Leu Lys
1               5                   10                  15
Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 12

Ala Ile Ser Trp Ser Gly Asp Ser Thr Tyr Tyr Ala Glu Ser Val Lys
1               5                   10                  15
Gly

<210> SEQ ID NO 13
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 13

Ala Ile Ser Trp Gln Gly Asp Ser Thr Tyr Tyr Ala Glu Ser Ala Lys
1               5                   10                  15
Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 14

Ala Ile Ser Trp Asn Ala Asp Ser Thr Tyr Tyr Ala Glu Ser Ala Lys
1               5                   10                  15
Gly

<210> SEQ ID NO 15
<211> LENGTH: 2
<212> TYPE: PRT
<213> ORGANISM: Artificial Sequence
<220> FEATURE:
<223> OTHER INFORMATION: Synthetic Oligopeptide

<400> SEQUENCE: 15

Asp Tyr
1

<210> SEQ ID NO 16
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 16

Ser Trp Ala Thr Pro Ile Glu Ser Leu Tyr Tyr Tyr Gly Met Asp Tyr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 17

Ser Trp Ala Thr Pro Ile Glu Ser Leu Tyr Tyr Tyr Gly Ser Asp Tyr
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Oligopeptide

<400> SEQUENCE: 18

Ser Trp Ala Thr Pro Ile Glu Ser Leu Tyr Tyr Tyr Gly Thr Asp Tyr
1               5                   10                  15

<210> SEQ ID NO 19
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 19

Gly Gly Asn Asn Ile Gly Ser Lys Asn Val His
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 20

Gly Gly Asn Asn Leu Gly Tyr Lys Ser Val His
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 21

```
Gly Gly Asn Asn Ile Gly Ser Gln Thr Ala Gln
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 22

Arg Asp Ser Asn Arg Pro Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 23

Arg Asp Asn Asn Arg Pro Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 24

Ala Asn Asn Arg Arg Pro Ser
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic Oligopeptide

<400> SEQUENCE: 25

Gln Val Val Val
1

<210> SEQ ID NO 26
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 26

Gln Val Trp Asp Gly Ser Thr Gln Ala Ile Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 27

Gln Val Trp Glu Asp Ser Thr Gln Ala Ile Val
```

```
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 28

```
Gln Val Trp Asp Glu Ser Thr Gln Ala Ile Val
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 29

```
Gln Val Trp Ala Ala Ser Thr Gln Ala Ile Val
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 30

```
Gln Val Trp Asp Asp Ser Thr Gln Ala Ile Val
1               5                   10
```

<210> SEQ ID NO 31
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 31

```
Gln Val Trp Glu Ala Ser Thr Gln Ala Ile Val
1               5                   10
```

<210> SEQ ID NO 32
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 32

```
Gln Val Trp Asp Ala Ser Thr Gln Ala Ile Val
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 33

```
Gln Val Trp Glu Glu Ser Thr Gln Ala Ile Val
1               5                   10
```

<210> SEQ ID NO 34
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 34

Gln Val Trp Glu Gly Ser Thr Gln Ala Ile Val
1               5                   10

<210> SEQ ID NO 35
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Trp Gly Gln Gly Thr Leu Val Thr Val Ser Ser
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Trp Gly Gln Gly Thr Leu Val Thr Val Ser Ser
            100                 105                 110

<210> SEQ ID NO 37
<211> LENGTH: 125

<212> TYPE: PRT
<213> ORGANISM: Artificial Sequence
<220> FEATURE:
<223> OTHER INFORMATION: Synthetic Polypeptide

<400> SEQUENCE: 37

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ser Trp Ala Thr Pro Ile Glu Ser Leu Tyr Tyr Tyr Gly Met
            100                 105                 110

Asp Tyr Trp Gly Lys Gly Thr Leu Val Thr Val Ser Ser
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 38

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 39
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr

```
                    20                  25                  30
Ser Met Ser Trp Val Arg Gln Ala Pro Gly Lys Gly Leu Glu Trp Val
            35                  40                  45

Ser Ala Ile Ser Trp Asn Gly Asp Ser Thr Tyr Tyr Ala Glu Ser Ala
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 40
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Ala Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 41
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Thr Trp Ser Gly Asp Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Thr
            100                 105                 110

Asp Tyr Trp Gly Lys Gly Thr Leu Val Thr Val Ser Ser
        115                 120                 125

<210> SEQ ID NO 42
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 43
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Leu Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Lys Gly Thr Leu Val Thr Val Ser Ser
        115                 120                 125

<210> SEQ ID NO 44

<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Lys Gly Thr Leu Val Thr Val Ser Ser
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 45

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 46

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Gln Gly Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
            115                 120                 125

<210> SEQ ID NO 47
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
            115                 120                 125

<210> SEQ ID NO 48
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser
        115                 120                 125
```

<210> SEQ ID NO 49
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 49

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Val Val Phe Gly Gly Gly Thr
                85                  90                  95

Lys Leu Thr Val Leu
            100
```

<210> SEQ ID NO 50
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 50

```
Ser Tyr Glu Leu Thr Gln Pro Leu Ser Val Ser Val Ala Leu Gly Gln
1               5                   10                  15

Ala Ala Arg Ile Thr Cys Gly Gly Asn Asn Leu Gly Tyr Lys Ser Val
            20                  25                  30

His Trp Tyr Gln Gln Lys Pro Gly Gln Ala Pro Val Leu Val Ile Tyr
        35                  40                  45

Arg Asp Asn Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Val Val Phe Gly Gly Gly Thr
                85                  90                  95

Lys Leu Thr Val Leu
            100
```

<210> SEQ ID NO 51
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 51

Ser Tyr Glu Leu Thr Gln Ser Pro Ser Val Ser Val Ala Leu Arg Gln
1               5                   10                  15

Thr Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Gly Ala Gln Ala Glu
65                  70                  75                  80

Asp Glu Ala Asp Tyr Tyr Cys Gln Val Trp Asp Gly Ser Thr Gln Ala
                85                  90                  95

Ile Val Phe Gly Gly Gly Thr His Leu Thr Val Leu
            100                 105

<210> SEQ ID NO 52
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 52

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Ser Ser Thr Gln Ala
                85                  90                  95

Ile Val Phe Gly Gly Gly Thr Lys Leu Thr Val Leu
            100                 105

<210> SEQ ID NO 53
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 53

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Ser Thr Gln Ala
                85                  90                  95

Ile Val Phe Gly Gly Gly Thr Lys Leu Thr Val Leu
            100                 105

<210> SEQ ID NO 54
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 54

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Gly Ala Gln Ala Glu
65                  70                  75                  80

Asp Glu Ala Asp Tyr Tyr Cys Gln Val Trp Ala Ala Ser Thr Gln Ala
                85                  90                  95

Ile Val Phe Gly Gly Gly Thr Lys Leu Thr Val Leu
            100                 105

<210> SEQ ID NO 55
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 55

Ser Tyr Glu Leu Thr Gln Pro Leu Ser Val Ser Val Ala Leu Arg Gln
1               5                   10                  15

Ala Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Asp Ser Thr Gln Ala
                85                  90                  95

Ile Val Phe Gly Gly Gly Thr Lys Leu Thr Val Leu
            100                 105

<210> SEQ ID NO 56
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 56

Ser Tyr Glu Leu Thr Gln Pro Leu Ser Val Ser Val Ala Leu Arg Gln
1               5                   10                  15

Ala Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Ala Ser Thr Gln Ala
                85                  90                  95

Ile Val Phe Gly Gly Gly Thr Lys Leu Thr Val Leu
            100                 105

<210> SEQ ID NO 57
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 57

Ser Tyr Glu Leu Thr Gln Ser Pro Ser Val Ser Val Ala Leu Arg Gln
1               5                   10                  15

Thr Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Gly Ala Gln Ala Gly
65                  70                  75                  80

Asp Glu Ala Asp Tyr Tyr Cys Gln Val Trp Asp Ala Ser Thr Gln Ala
                85                  90                  95

Ile Val Phe Gly Gly Gly Thr Lys Leu Thr Val Leu
            100                 105

<210> SEQ ID NO 58
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 58

Ser Tyr Glu Leu Thr Gln Pro Leu Ser Val Ser Val Ala Leu Gly Gln
1               5                   10                  15

Thr Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Glu Ser Thr Gln Ala
                85                  90                  95

```
Ile Val Phe Gly Gly Gly Thr His Leu Thr Val Leu
            100                 105

<210> SEQ ID NO 59
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 59

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Gly Ser Thr Gln Ala
                85                  90                  95

Ile Val Phe Gly Gly Gly Thr Lys Leu Thr Val Leu
            100                 105

<210> SEQ ID NO 60
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 60

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ala Ser Thr Gln Ala
                85                  90                  95

Ile Val Phe Gly Gly Gly Thr Lys Leu Thr Val Leu
            100                 105

<210> SEQ ID NO 61
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 61

Ser Tyr Glu Leu Thr Gln Pro Leu Ser Val Ser Val Ala Leu Arg Gln
1               5                   10                  15
```

```
Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Gly Ser Thr Gln Ala
                85                  90                  95

Ile Val Phe Gly Gly Gly Thr Lys Leu Thr Val Leu
            100                 105
```

<210> SEQ ID NO 62
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 62

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

-continued

```
Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 63
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 63

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 64
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Gln Gly Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 65
<211> LENGTH: 455
<212> TYPE: PRT
<213> ORGANISM: Artificial Sequence
<220> FEATURE:
<223> OTHER INFORMATION: Synthetic Polypeptide
```

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Ala Asp Ser Thr Tyr Tyr Ala Glu Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
```

```
                    405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 66
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 66

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Gln Gly Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
```

```
                305                 310                 315                 320
Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
        450                 455

<210> SEQ ID NO 67
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 67

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
                20                  25                  30

Ser Met Ser Trp Val Arg Gln Ala Pro Gly Lys Gly Leu Glu Trp Val
            35                  40                  45

Ser Ala Ile Ser Trp Asn Ala Asp Ser Thr Tyr Tyr Ala Glu Ser Leu
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
```

```
              210                 215                 220
Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                    260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
            450                 455

<210> SEQ ID NO 68
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 68

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
                20                  25                  30

Ser Met Ser Trp Val Arg Gln Ala Pro Gly Lys Gly Leu Glu Trp Val
            35                  40                  45

Ser Ala Ile Ser Trp Asn Ala Asp Ser Thr Tyr Tyr Ala Glu Ser Leu
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
                100                 105                 110

Asp Tyr Trp Gly Gln Gly Thr Leu Val Thr Val Ser Ser Ala Ser Thr
```

```
            115                 120                 125
Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Ala Ala Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
                435                 440                 445

Leu Ser Leu Ser Pro Gly Lys
            450                 455

<210> SEQ ID NO 69
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
```

```
                20                  25                  30
Ser Met Ser Trp Val Arg Gln Ala Pro Gly Lys Gly Leu Glu Trp Val
            35                  40                  45
Ser Ala Ile Ser Trp Asn Ala Asp Ser Thr Tyr Tyr Ala Glu Ser Ala
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Ser Trp Ala Thr Pro Ile Glu Ser Leu Tyr Tyr Gly Ser
            100                 105                 110
Asp Tyr Trp Gly Gln Gly Thr Leu Val Thr Val Ser Ser Ala Ser Thr
            115                 120                 125
Lys Gly Pro Ser Val Phe Pro Leu Ala Pro Ser Ser Lys Ser Thr Ser
            130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Leu Gly Thr Gln Thr Tyr Ile Cys
            195                 200                 205
Asn Val Asn His Lys Pro Ser Asn Thr Lys Val Asp Lys Lys Val Glu
            210                 215                 220
Pro Lys Ser Cys Asp Lys Thr His Thr Cys Pro Pro Cys Pro Ala Pro
225                 230                 235                 240
Glu Ala Ala Gly Ala Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
            435                 440                 445
```

Leu Ser Leu Ser Pro Gly Lys
    450                 455

<210> SEQ ID NO 70
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 70

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ser Trp Ala Thr Pro Ile Glu Ser Leu Tyr Tyr Tyr Gly Met
            100                 105                 110

Asp Tyr Trp Gly Lys Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

```
Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 71
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 71

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 72
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 72

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 73
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Ala
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Trp Ala Thr Pro Ile Glu Ser Leu Tyr Tyr Gly Ser
            100                 105                 110         Ser

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 74
<211> LENGTH: 455
```

```
<212> TYPE: PRT
<213> ORGANISM: Artificial Sequence
<220> FEATURE:
<223> OTHER INFORMATION: Synthetic Polypeptide

<400> SEQUENCE: 74

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ser Met Ser Trp Val Arg Gln Ala Pro Gly Lys Gly Leu Glu Trp Val
        35                  40                  45

Ser Ala Ile Ser Trp Asn Gly Asp Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ser Trp Ala Thr Pro Ile Glu Ser Leu Tyr Tyr Tyr Gly Met
            100                 105                 110

Asp Tyr Trp Gly Lys Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Ser Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380
```

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met Asn Glu Ala Leu His Asn His Tyr Thr Gln Lys Ser
                435                 440                 445

Leu Ser Leu Ser Pro Gly Lys
    450                 455

<210> SEQ ID NO 75
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 75

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
                20                  25                  30

Gln Trp Tyr Gln Gln Lys Pro Gly Gln Ala Pro Val Leu Val Ile Tyr
            35                  40                  45

Ala Asn Asn Arg Arg Pro Ser Gly Ile Pro Glu Arg Phe Ser Gly Ser
        50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Glu Gly Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 76
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 76

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ala Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210

<210> SEQ ID NO 77
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 77

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Glu Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 78
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 78

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 79
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 79

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala

```
                   20                  25                  30
Gln Trp Tyr Gln Gln Lys Pro Gly Gln Ala Pro Val Leu Val Ile Tyr
            35                  40                  45
Ala Asn Asn Arg Arg Pro Ser Gly Ile Pro Glu Arg Phe Ser Gly Ser
 50                  55                  60
Lys Ser Gly Asn Thr Ala Thr Leu Thr Ile Ser Arg Ala Gln Ala Glu
 65                  70                  75                  80
Asp Glu Ala Asp Tyr Tyr Cys Gln Val Trp Glu Asp Ser Thr Gln Ala
                 85                  90                  95
Ile Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser
    210

<210> SEQ ID NO 80
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 80

Ser Tyr Glu Leu Thr Gln Pro Leu Ser Val Ser Val Ala Leu Gly Gln
 1               5                  10                  15
Thr Ala Arg Ile Thr Cys Gly Gly Asn Asn Ile Gly Ser Gln Thr Ala
            20                  25                  30
Gln Trp Tyr Gln Gln Lys Pro Gly Gln Ala Pro Val Leu Val Ile Tyr
        35                  40                  45
Ala Asn Asn Arg Arg Pro Ser Gly Ile Pro Glu Arg Phe Ser Gly Ser
 50                  55                  60
Lys Ser Gly Asn Thr Ala Thr Leu Thr Ile Ser Arg Ala Gln Ala Glu
 65                  70                  75                  80
Asp Glu Ala Asp Tyr Tyr Cys Gln Val Trp Glu Asp Ser Thr Gln Ala
                 85                  90                  95
Ile Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
```

165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 81
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 81

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
    50                  55                  60

Lys Ser Gly Asn Thr Ala Thr Leu Thr Ile Ser Arg Ala Gln Ala Glu
65                  70                  75                  80

Asp Glu Ala Asp Tyr Tyr Cys Gln Val Trp Glu Asp Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 82
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 82

Ser Tyr Glu Leu Thr Gln Pro Leu Ser Val Ser Val Ala Leu Arg Gln
1               5                   10                  15

Thr Ala Arg Ile Thr Cys Gly Gly Asn Asn Ile Gly Ser Gln Thr Ala
            20                  25                  30

```
Gln Trp Tyr Gln Gln Lys Pro Gly Gln Ala Pro Val Leu Val Ile Tyr
            35                  40                  45

Ala Asn Asn Arg Arg Pro Ser Gly Ile Pro Glu Arg Phe Ser Gly Ser
 50                  55                  60

Lys Ser Gly Asn Thr Ala Thr Leu Thr Ile Ser Arg Ala Gln Ala Glu
 65                  70                  75                  80

Asp Glu Ala Asp Tyr Tyr Cys Gln Val Trp Asp Ser Thr Gln Ala
                 85                  90                  95

Ile Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 83
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 83

Ser Tyr Glu Leu Thr Gln Ser Pro Ser Val Ser Val Ala Leu Arg Gln
 1               5                  10                  15

Thr Ala Lys Ile Thr Cys Gly Gly Asn Asn Ile Gly Ser Gln Thr Ala
             20                  25                  30

Gln Trp Tyr Gln Gln Lys Pro Gly Gln Ala Pro Val Leu Val Ile Tyr
            35                  40                  45

Ala Asn Asn Arg Arg Pro Ser Gly Ile Pro Glu Arg Phe Ser Gly Ser
 50                  55                  60

Lys Ser Gly Asn Thr Ala Thr Leu Thr Ile Ser Gly Ala Gln Ala Glu
 65                  70                  75                  80

Asp Glu Ala Asp Tyr Tyr Cys Gln Val Trp Asp Gly Ser Thr Gln Ala
                 85                  90                  95

Ile Val Phe Gly Gly Gly Thr His Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175
```

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 84
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 84

Ser Tyr Glu Leu Thr Gln Pro Leu Ser Val Ser Val Ala Leu Arg Gln
1               5                   10                  15

Ala Ala Lys Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

Ala Asn Asn Arg Arg Pro Ser Gly Ile Pro Glu Arg Phe Ser Gly Ser
50                  55                  60

Lys Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Gly Ser Thr Gln Ala
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 85
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 85

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Gln Thr Ala
            20                  25                  30

Gln Trp Tyr Gln Gln Lys Pro Gly Gln Ala Pro Val Leu Val Ile Tyr
        35                  40                  45

```
Ala Asn Asn Arg Arg Pro Ser Gly Ile Pro Glu Arg Phe Ser Gly Ser
     50                  55                  60

Lys Ser Gly Asn Thr Ala Thr Leu Thr Ile Ser Arg Ala Gln Ala Glu
 65                  70                  75                  80

Asp Glu Ala Asp Tyr Tyr Cys Gln Val Trp Glu Asp Ser Thr Gln Ala
                 85                  90                  95

Ile Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 86
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 86

Ser Tyr Glu Leu Thr Gln Pro Leu Ser Val Ser Val Ala Leu Arg Gln
 1               5                  10                  15

Thr Ala Arg Ile Thr Cys Gly Gly Asn Asn Ile Gly Ser Gln Thr Ala
                 20                  25                  30

Gln Trp Tyr Gln Gln Lys Pro Gly Gln Ala Pro Val Leu Val Ile Tyr
             35                  40                  45

Ala Asn Asn Arg Arg Pro Ser Gly Ile Pro Glu Arg Phe Ser Gly Ser
     50                  55                  60

Lys Ser Gly Asn Thr Ala Thr Leu Thr Ile Ser Arg Ala Gln Ala Glu
 65                  70                  75                  80

Asp Glu Ala Asp Tyr Tyr Cys Gln Val Trp Asp Ser Ser Thr Gln Ala
                 85                  90                  95

Ile Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
        195                 200                 205

Ala Pro Thr Glu Cys Ser
    210

<210> SEQ ID NO 87
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 88

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 89
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 89

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Ser Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met Asn Glu Ala Leu His Asn His Tyr Thr
305                 310                 315                 320

Gln Lys Ser Leu Ser Leu Ser Pro Gly Lys
                325                 330
```

<210> SEQ ID NO 90
<211> LENGTH: 1338
<212> TYPE: PRT
<213> ORGANISM: Homo sapiens

<400> SEQUENCE: 90

```
Met Val Ser Tyr Trp Asp Thr Gly Val Leu Leu Cys Ala Leu Leu Ser
1               5                   10                  15
```

```
Cys Leu Leu Leu Thr Gly Ser Ser Gly Ser Lys Leu Lys Asp Pro
             20                  25                  30

Glu Leu Ser Leu Lys Gly Thr Gln His Ile Met Gln Ala Gly Gln Thr
         35                  40                  45

Leu His Leu Gln Cys Arg Gly Glu Ala Ala His Lys Trp Ser Leu Pro
     50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
             85                  90                  95

Ala Gln Ala Asn His Thr Gly Phe Tyr Ser Cys Lys Tyr Leu Ala Val
        100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
    355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
```

```
                    435                 440                 445
Arg Gln Ile Leu Thr Cys Thr Ala Tyr Gly Ile Pro Gln Pro Thr Ile
            450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
                595                 600                 605
Met Ala Ile Thr Lys Glu His Ser Ile Thr Leu Asn Leu Thr Ile Met
610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
                660                 665                 670
Ala Ile Ser Ser Ser Thr Thr Leu Asp Cys His Ala Asn Gly Val Pro
            675                 680                 685
Glu Pro Gln Ile Thr Trp Phe Lys Asn Asn His Lys Ile Gln Gln Glu
            690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                725                 730                 735
Lys Gly Ser Val Glu Ser Ser Ala Tyr Leu Thr Val Gln Gly Thr Ser
                740                 745                 750
Asp Lys Ser Asn Leu Glu Leu Ile Thr Leu Thr Cys Thr Cys Val Ala
            755                 760                 765
Ala Thr Leu Phe Trp Leu Leu Leu Thr Leu Phe Ile Arg Lys Met Lys
            770                 775                 780
Arg Ser Ser Ser Glu Ile Lys Thr Asp Tyr Leu Ser Ile Ile Met Asp
785                 790                 795                 800
Pro Asp Glu Val Pro Leu Asp Glu Gln Cys Glu Arg Leu Pro Tyr Asp
                805                 810                 815
Ala Ser Lys Trp Glu Phe Ala Arg Glu Arg Leu Lys Leu Gly Lys Ser
            820                 825                 830
Leu Gly Arg Gly Ala Phe Gly Lys Val Val Gln Ala Ser Ala Phe Gly
            835                 840                 845
Ile Lys Lys Ser Pro Thr Cys Arg Thr Val Ala Val Lys Met Leu Lys
            850                 855                 860
```

```
Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
        885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
        930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260
```

```
Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 91
<211> LENGTH: 720
<212> TYPE: PRT
<213> ORGANISM: Homo sapiens

<400> SEQUENCE: 91

Met Val Ser Tyr Trp Asp Thr Gly Val Leu Leu Cys Ala Leu Leu
1               5                   10                  15

Cys Leu Leu Leu Thr Gly Ser Ser Gly Ser Lys Leu Lys Asp Pro
                20                  25                  30

Glu Leu Ser Leu Lys Gly Thr Gln His Ile Met Gln Ala Gly Gln
                35                  40                  45

Leu His Leu Gln Cys Arg Gly Glu Ala Ala His Lys Trp Ser Leu
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
                115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
                195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
                260                 265                 270

Asn Lys Arg Ala Ser Val Arg Arg Ile Asp Gln Ser Asn Ser His
                275                 280                 285

Ala Asn Ile Phe Tyr Ser Val Leu Thr Ile Asp Lys Met Gln Asn Lys
    290                 295                 300
```

```
Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
690                 695                 700

Pro Asp Ala Asp Pro His Ile Gln Lys Ala Asp Cys Thr Phe Phe Phe
705                 710                 715                 720
```

-continued

<210> SEQ ID NO 92
<211> LENGTH: 687
<212> TYPE: PRT
<213> ORGANISM: Homo sapiens

<400> SEQUENCE: 92

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380
```

```
Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
        420                 425                 430

Lys Ala Val Ser Ser Phe Pro Asp Pro Ala Leu Tyr Pro Leu Gly Ser
    435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
        500                 505                 510

Glu Gly Lys Asn Lys Met Ala Ser Thr Leu Val Val Ala Asp Ser Arg
    515                 520                 525

Ile Ser Gly Ile Tyr Ile Cys Ile Ala Ser Asn Lys Val Gly Thr Val
530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
        580                 585                 590

Arg Thr Val Asn Asn Arg Thr Met His Tyr Ser Ile Ser Lys Gln Lys
    595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Gly Glu His Cys Asn Lys Lys Ala Val Phe Ser Arg Ile Ser Lys Phe
        660                 665                 670

Lys Ser Thr Arg Asn Asp Cys Thr Thr Gln Ser Asn Val Lys His
    675                 680                 685

<210> SEQ ID NO 93
<211> LENGTH: 733
<212> TYPE: PRT
<213> ORGANISM: Homo sapiens

<400> SEQUENCE: 93

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
```

```
              65                  70                  75                  80
Cys Gly Arg Asn Gly Lys Gln Phe Cys Ser Thr Leu Thr Leu Asn Thr
                 85                  90                  95
Ala Gln Ala Asn His Thr Gly Phe Tyr Ser Cys Lys Tyr Leu Ala Val
                100                 105                 110
Pro Thr Ser Lys Lys Glu Thr Glu Ser Ala Ile Tyr Ile Phe Ile
                115                 120                 125
Ser Asp Thr Gly Arg Pro Phe Val Glu Met Tyr Ser Glu Ile Pro Glu
            130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
            195                 200                 205
Ala Thr Val Asn Gly His Leu Tyr Lys Thr Asn Tyr Leu Thr His Arg
        210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
        355                 360                 365
Trp Leu Lys Asp Gly Leu Pro Ala Thr Glu Lys Ser Ala Arg Tyr Leu
        370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
```

```
Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
        530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
            610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Glu Leu Tyr Thr Ser Thr Ser Pro Ser Ser Ser Ser Ser Ser Pro
705                 710                 715                 720

Leu Ser Ser Ser Ser Ser Ser Ser Ser Ser Ser
                725                 730

<210> SEQ ID NO 94
<211> LENGTH: 541
<212> TYPE: PRT
<213> ORGANISM: Homo sapiens

<400> SEQUENCE: 94

Met Val Ser Tyr Trp Asp Thr Gly Val Leu Leu Cys Ala Leu Leu Ser
1               5                   10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
```

```
            130                 135                 140
Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
                195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
                260                 265                 270

Asn Lys Arg Ala Ser Val Arg Arg Ile Asp Gln Ser Asn Ser His
                275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
                355                 360                 365

Trp Leu Lys Asp Gly Leu Pro Ala Thr Glu Lys Ser Ala Arg Tyr Leu
                370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
                435                 440                 445

Arg Gln Ile Leu Thr Cys Thr Ala Tyr Gly Ile Pro Gln Pro Thr Ile
                450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Leu Pro Pro Ala Asn Ser Ser Phe Met Leu Pro
                515                 520                 525

Pro Thr Ser Phe Ser Ser Asn Tyr Phe His Phe Leu Pro
530                 535                 540

<210> SEQ ID NO 95
```

```
<211> LENGTH: 13
<212> TYPE: PRT
<213> ORGANISM: Homo sapiens

<400> SEQUENCE: 95

Glu Ile Pro Glu Ile Ile His Met Thr Glu Gly Arg Glu
1               5                   10

<210> SEQ ID NO 96
<211> LENGTH: 14
<212> TYPE: PRT
<213> ORGANISM: Homo sapiens

<400> SEQUENCE: 96

Ile Ile Ser Asn Ala Thr Tyr Lys Glu Ile Gly Leu Leu Thr
1               5                   10

<210> SEQ ID NO 97
<211> LENGTH: 9
<212> TYPE: PRT
<213> ORGANISM: Homo sapiens

<400> SEQUENCE: 97

Asp Thr Gly Arg Pro Phe Val Glu Met
1               5

<210> SEQ ID NO 98
<211> LENGTH: 8
<212> TYPE: PRT
<213> ORGANISM: Homo sapiens

<400> SEQUENCE: 98

Glu Ile Pro Glu Ile Ile His Met
1               5

<210> SEQ ID NO 99
<211> LENGTH: 10
<212> TYPE: PRT
<213> ORGANISM: Homo sapiens

<400> SEQUENCE: 99

Tyr Ser Glu Ile Pro Glu Ile Ile His Met
1               5                   10

<210> SEQ ID NO 100
<211> LENGTH: 15
<212> TYPE: PRT
<213> ORGANISM: Homo sapiens

<400> SEQUENCE: 100

Tyr Ser Glu Ile Pro Glu Ile Ile His Met Thr Glu Gly Arg Glu
1               5                   10                  15

<210> SEQ ID NO 101
<211> LENGTH: 29
<212> TYPE: PRT
<213> ORGANISM: Homo sapiens

<400> SEQUENCE: 101

Ile Pro Asp Gly Lys Arg Ile Ile Trp Asp Ser Arg Lys Gly Phe Ile
1               5                   10                  15

Ile Ser Asn Ala Thr Tyr Lys Glu Ile Gly Leu Leu Thr
            20                  25
```

-continued

<210> SEQ ID NO 102
<211> LENGTH: 6
<212> TYPE: PRT
<213> ORGANISM: Homo sapiens

<400> SEQUENCE: 102

Tyr Lys Glu Ile Gly Leu
1               5

<210> SEQ ID NO 103
<211> LENGTH: 11
<212> TYPE: PRT
<213> ORGANISM: Homo sapiens

<400> SEQUENCE: 103

Ile Ser Asp Thr Gly Arg Pro Phe Val Glu Met
1               5                   10

<210> SEQ ID NO 104
<211> LENGTH: 238
<212> TYPE: PRT
<213> ORGANISM: Artificial Sequence
<220> FEATURE:
<223> OTHER INFORMATION: Synthetic Polypeptide

<400> SEQUENCE: 104

Thr Lys Val Asp Lys Lys Val Glu Pro Lys Ser Cys Asp Lys Thr His
1               5                   10                  15

Thr Cys Pro Pro Cys Pro Ala Pro Glu Leu Leu Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly
225                 230                 235

<210> SEQ ID NO 105
<211> LENGTH: 21

```
<212> TYPE: PRT
<213> ORGANISM: Artificial Sequence
<220> FEATURE:
<223> OTHER INFORMATION: Synthetic Oligopeptide

<400> SEQUENCE: 105

Gly Ala Pro Gly Gly Gly Gly Ala Ala Ala Ala Gly Gly Gly
1               5                   10                  15

Gly Gly Gly Ala Pro
            20

<210> SEQ ID NO 106
<211> LENGTH: 39
<212> TYPE: PRT
<213> ORGANISM: Artificial Sequence
<220> FEATURE:
<223> OTHER INFORMATION: Synthetic Oligopeptide

<400> SEQUENCE: 106

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro
        35

<210> SEQ ID NO 107
<211> LENGTH: 57
<212> TYPE: PRT
<213> ORGANISM: Artificial Sequence
<220> FEATURE:
<223> OTHER INFORMATION: Synthetic Oligopeptide

<400> SEQUENCE: 107

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro Gly Gly Gly Gly Ala Ala Ala Ala
        35                  40                  45

Ala Gly Gly Gly Gly Gly Gly Ala Pro
    50                  55

<210> SEQ ID NO 108
<211> LENGTH: 475
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (475)..(475)
<223> OTHER INFORMATION: Xaa can be any naturally occurring amino acid

<400> SEQUENCE: 108

Met Gly Trp Ser Cys Ile Ile Leu Phe Leu Val Ala Thr Ala Thr Gly
1               5                   10                  15

Val His Ser Glu Leu Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Ser Ala Ser Trp Val Arg Gln Ala Pro Gly Lys Gly Leu
    50                  55                  60
```

```
Glu Trp Val Ser Ala Ile Ser Trp Ser Gly Asp Ser Thr Tyr Tyr Ala
 65                  70                  75                  80

Glu Ser Val Lys Gly Arg Phe Thr Ile Phe Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Lys Ser Trp Ala Thr Pro Ile Glu Ser Leu Tyr Tyr
        115                 120                 125

Tyr Gly Ser Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Ala Ala Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys Xaa
465                 470                 475
```

```
<210> SEQ ID NO 109
<211> LENGTH: 455
<212> TYPE: PRT
<213> ORGANISM: Artificial Sequence
<220> FEATURE:
<223> OTHER INFORMATION: Synthetic Polypeptide

<400> SEQUENCE: 109

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Ala Ser Trp Val Arg Gln Ala Pro Gly Lys Gly Leu Glu Trp Val
        35                  40                  45

Ser Ala Ile Ser Trp Ser Gly Asp Ser Thr Tyr Tyr Ala Glu Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Ala Thr Pro Ile Glu Ser Leu Tyr Tyr Tyr Gly Ser
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365
```

```
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
            435                 440                 445
Leu Ser Leu Ser Pro Gly Lys
    450                 455

<210> SEQ ID NO 110
<211> LENGTH: 234
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (234)..(234)
<223> OTHER INFORMATION: Xaa can be any naturally occurring amino acid

<400> SEQUENCE: 110

Met Gly Trp Ser Cys Ile Ile Leu Phe Leu Val Ala Thr Ala Thr Gly
1                5                   10                  15
Val His Ser Ser Tyr Glu Leu Thr Gln Pro Leu Ser Val Ser Val Ala
                20                  25                  30
Leu Arg Gln Ala Ala Lys Ile Thr Cys Gly Gly Asn Asn Ile Gly Ser
            35                  40                  45
Gln Thr Ala Gln Trp Tyr Gln Gln Lys Pro Gly Gln Ala Pro Val Leu
        50                  55                  60
Val Ile Tyr Ala Asn Asn Arg Arg Pro Ser Gly Ile Pro Glu Arg Phe
65                  70                  75                  80
Ser Gly Ser Lys Ser Gly Asn Thr Ala Thr Leu Thr Ile Ser Arg Ala
                85                  90                  95
Gln Ala Gly Asp Glu Ala Asp Tyr Tyr Cys Gln Val Trp Asp Ala Ser
            100                 105                 110
Thr Gln Ala Ile Val Phe Gly Gly Gly Thr Lys Leu Thr Val Leu Gly
        115                 120                 125
Gln Pro Lys Ala Ala Pro Ser Val Thr Leu Phe Pro Pro Ser Ser Glu
130                 135                 140
Glu Leu Gln Ala Asn Lys Ala Thr Leu Val Cys Leu Ile Ser Asp Phe
145                 150                 155                 160
Tyr Pro Gly Ala Val Thr Val Ala Trp Lys Ala Asp Ser Ser Pro Val
                165                 170                 175
Lys Ala Gly Val Glu Thr Thr Thr Pro Ser Lys Gln Ser Asn Asn Lys
            180                 185                 190
Tyr Ala Ala Ser Ser Tyr Leu Ser Leu Thr Pro Glu Gln Trp Lys Ser
        195                 200                 205
His Arg Ser Tyr Ser Cys Gln Val Thr His Glu Gly Ser Thr Val Glu
    210                 215                 220
Lys Thr Val Ala Pro Thr Glu Cys Ser Xaa
225                 230

<210> SEQ ID NO 111
```

```
<211> LENGTH: 19
<212> TYPE: PRT
<213> ORGANISM: Artificial Sequence
<220> FEATURE:
<223> OTHER INFORMATION: Synthetic Oligopeptide

<400> SEQUENCE: 111

Met Gly Trp Ser Cys Ile Ile Leu Phe Leu Val Ala Thr Ala Thr Gly
1               5                   10                  15

Val His Ser
```

ANTI-FLT-1 ANTIBODIES FOR TREATING DUCHENNE MUSCULAR DYSTROPHY

RELATED APPLICATIONS

This application is a 35 U.S.C. § 371 National Stage Application of International Application No. PCT/US16/26352, filed Apr. 7, 2016, which claims priority to U.S. Provisional Application Ser. No. 62/144,251, filed Apr. 7, 2015 and U.S. Provisional Application Ser. No. 62/307,645, filed Mar. 14, 2016, the disclosure of each of which is hereby incorporated by reference.

INCORPORATION-BY-REFERENCE OF SEQUENCE LISTING

The content of the text file named "SHR-1189US_ST25.txt", which was created on Oct. 6, 2017 and is 168 KB in size, is hereby incorporated by reference in its entirety.

BACKGROUND

Duchenne muscular dystrophy (DMD) is an X-linked recessive disorder affecting an estimated 1:3600 male births with an estimated 50,000 affected individuals worldwide. The disorder is marked by a progressive wasting of the muscles and affected children are wheelchair dependent by the time they reach 13 years of age. Affected individuals usually present with symptoms at 3 years of age with the median survival for such individuals being between 25 and 30 years of age. Respiratory failure due to diaphragmatic weakness and cardiomyopathy are common causes of death.

DMD is caused by a mutation in the dystrophin gene. The dystrophin gene is located on the X chromosome and codes for the protein dystrophin. Dystrophin protein is responsible for connecting the contractile machinery (actin-myosin complex) of a muscle fiber to the surrounding extracellular matrix through the dystroglycan complex. Mutations in the dystrophin gene result in either alteration or absence of the dystrophin protein and abnormal sarcolemal membrane function. While both males and females can carry a mutation in the dystrophin gene, females are rarely affected with DMD.

One characteristic of DMD is ischemia of the affected tissues. Ischemia is a restriction or decrease in blood supply to tissues or organs, causing a shortage of oxygen and nutrients need for cellular metabolism. Ischemia is generally caused by constriction or obstruction of blood vessels resulting in damage to or dysfunction of the tissue or organ. Treatment of ischemia is directed toward increasing the blood flow to the affected tissue or organ.

Presently, there is no cure for DMD. Several therapeutic avenues have been investigated including gene therapy and corticosteroid administration, however the need for alternatives for DMD patients still exists.

SUMMARY OF INVENTION

The present invention provides, among other things, improved methods and compositions for treating muscular dystrophy, in particular, Duchenne muscular dystrophy (DMD) and/or Becker muscular dystrophy based on anti-Flt-1 antibody therapy. As described in the Examples below, the invention is, in part, based on the discovery that anti-Flt-1 antibodies, or antigen-binding fragments thereof, can inhibit VEGF and other ligands from binding to the Flt-1 receptor, thereby increasing the amount of VEGF and/or other ligands available to bind to VEGF receptors. Increased availability of VEGF promotes angiogenesis with increased blood flow to muscle to combat functional ischemia and leading to improvements in structural and functional characteristics of DMD. Indeed, as shown in the present Examples, the present inventors have demonstrated that administration of the anti-Flt-1 antibody improves measures of muscle pathology (e.g., improved angiogenesis, reduced fibrosis, reduced necrosis). Therefore, the present invention provides safe and effective antibody-based therapeutics for the treatment of DMD.

In one aspect, the invention provides antibodies or antigen-binding fragments thereof that specifically bind to human Flt-1 comprising one or more complementarity determining regions (CDR) selected from the group consisting of: a variable light (VL) chain CDR1 defined by an amino acid sequence having at least 80% identity to any one of SEQ ID NO: 19 to SEQ ID NO:21, a VL CDR2 defined by an amino acid sequence having at least 80% identity to any one of SEQ ID NO:22 to SEQ ID NO:24; a VL CDR3 defined by an amino acid sequence having at least 80% identity to any one of SEQ ID NO:25 to SEQ ID NO:34; a variable heavy (VH) chain CDR1 defined by an amino acid sequence having at least 80% identity to any one of SEQ ID NO: 1 to SEQ ID NO:4, a VH CDR2 defined by an amino acid sequence having at least 80% identity to any one of SEQ ID NO:5 to SEQ ID NO: 14, and a VH CDR3 defined by an amino acid sequence having at least 80% identity to any one of SEQ ID NO: 15 to SEQ ID NO:18.

In some embodiments, the one or more CDRs comprise the VL CDR3 defined by the amino acid sequence having at least 80% identity to any one of SEQ ID NO:25 to SEQ ID NO:34; and the VH CDR3 defined by the amino acid sequence having at least 80% identity to any one of SEQ ID NO:15 to SEQ ID NO:18.

In another embodiment, the one or more CDRs comprise the VL CDR1 defined by the amino acid sequence having at least 80% identity to any one of SEQ ID NO: 19 to SEQ ID NO:21, the VL CDR2 defined by the amino acid sequence having at least 80% identity to any one of SEQ ID NO:22 to SEQ ID NO:24, and the VL CDR3 defined by the amino acid sequence having at least 80% identity to any one of SEQ ID NO:25 to SEQ ID NO:34. In a particular embodiment, VL chain comprises the VL CDR1, VL CDR2, and VL CDR3 defined by the amino acid sequence of SEQ ID NO: 19, SEQ ID NO:22, and SEQ ID NO:25, respectively. In yet another embodiment, the VL chain comprises the VL CDR1, VL CDR2, and VL CDR3 defined by the amino acid sequence of SEQ ID NO:20, SEQ ID NO:23, and SEQ ID NO:25, respectively. In another embodiment, the VL chain comprises the VL CDR1 and VL CDR2 defined by the amino acid sequence of SEQ ID NO:21 and SEQ ID NO:24, respectively, and the VL CDR3 defined by the amino acid sequence of SEQ ID NO:26, SEQ ID NO:27, SEQ ID NO:28, SEQ ID NO:29, SEQ ID NO:30, SEQ ID NO:31, SEQ ID NO:32, SEQ ID NO:33, or SEQ ID NO:34. In a particular embodiment, the VL chain comprises the VL CDR1, VL CDR2, and VL CDR3 defined by the amino acid sequence of SEQ ID NO:21, SEQ ID NO:24, and SEQ ID NO:32, respectively.

In other embodiments, the one or more CDRs comprise the VH CDR1 defined by the amino acid sequence having at least 80% identity to any one of SEQ ID NO: 1 to SEQ ID NO:4, the VH CDR2 defined by the amino acid sequence having at least 80% identity to any one of SEQ ID NO:5 to SEQ ID NO: 14, and the VH CDR3 defined by the amino acid sequence having at least 80% identity to any one of SEQ ID NO: 15 to SEQ ID NO: 18. In a particular embodiment, the VH chain comprises the VH CDR1, VH CDR2, and VH CDR3 defined by the amino acid sequences of SEQ ID NO:1, SEQ ID NO:5, and SEQ ID NO: 15, respectively. In another embodiment the VH chain comprises the VH CDR1, VH CDR2, and VH CDR3 defined by the amino acid sequences of SEQ ID NO:2, SEQ ID NO:6, and SEQ ID NO: 16, respectively. In yet another embodiment, the VH chain comprises the VH CDR1, VH CDR2, and VH CDR3 defined by the amino acid sequences of SEQ ID NO:2, SEQ ID NO: 10, and SEQ ID NO: 18, respectively. In another embodiment, the VH chain comprises the VH CDR1 and the VH CDR3 defined by the amino acid sequences of SEQ ID NO:2 and SEQ ID NO: 17, respectively, and the VH CDR2 defined by the amino acid sequence of SEQ ID NO:7, SEQ ID NO:8, SEQ ID NO: 13 or SEQ ID NO: 14. In another embodiment, the VH chain comprises the VH CDR1 and the VH CDR3 defined by the amino acid sequences of SEQ ID NO:3 and SEQ ID NO: 17, respectively, and the VH CDR2 defined by the amino acid sequence of SEQ ID NO:9, SEQ ID NO: 11 or SEQ ID NO: 12. In yet another embodiment, the VH chain comprises the VH CDR1, VH CDR2, and VH CDR3 defined by the amino acid sequences of SEQ ID NO:4, SEQ ID NO:9, and SEQ ID NO:17, respectively. In a particular embodiment, the VH chain comprising the VH CDR1, VH CDR2, and VH CDR3 defined by the amino acid sequences of SEQ ID NO:3, SEQ ID NO: 12, and SEQ ID NO:17, respectively.

In another aspect, the invention provides antibodies or antigen-binding fragments thereof that specifically bind to human Flt-1, comprising: (i) a light chain variable (VL) region comprising an amino acid sequence having at least 80% identity to any one of SEQ ID NO:49 to SEQ ID NO:61, and/or (ii) a heavy chain variable (VH) region comprising an amino acid sequence having at least 80% identity to any one of SEQ ID NO:35 to SEQ ID NO:48. In a particular embodiment the VL region comprises the amino acid sequence of SEQ ID NO:60 and the VH region comprises the amino acid sequence of SEQ ID NO:45.

In some embodiments the antibody further comprises a heavy chain constant region comprising an amino acid sequence having at least 80% identity to any one of SEQ ID NO:87 to SEQ ID NO:89.

In another aspect, the invention provides antibodies or antigen-binding fragments thereof that specifically binds to human Flt-1, comprising: (i) a light chain comprising an amino acid sequence having at least 80% identity to any one of SEQ ID NO:75 to SEQ ID NO:86, and/or (ii) a heavy chain comprising an amino acid sequence having at least 80% identity to any one of SEQ ID NO:62 to SEQ ID NO:74. In a particular embodiment, the light chain comprises the amino acid sequence of SEQ ID NO:76 and the heavy chain comprises the amino acid sequence of SEQ ID NO:71.

In another embodiment, the antibody or antigen-binding fragment thereof is selected from the group consisting of IgG, F(ab')$_2$, F(ab)$_2$, Fab', Fab, ScFvs, diabodies, triabodies and tetrabodies. In one embodiment the antibody or antigen-binding fragment thereof is IgG. In another embodiment the antibody or antigen-binding fragment thereof is IgG1. In yet another embodiment, the antibody or antigen-binding fragment thereof is a monoclonal antibody. In a particular embodiment, the antibody is a humanized monoclonal antibody. In yet another embodiment, the humanized monoclonal antibody contains a human Fc region. In some embodiments, Fc region contains one or more mutations that enhance the binding affinity between the Fc region and the FcRn receptor such that the in vivo half-life of the antibody is prolonged. In another embodiment, the Fc region contains one or more mutations at positions corresponding to Leu 234, Leu 235 and/or Gly 237 of human IgG1.

In one embodiment, the antibody or antigen-binding fragment thereof does not bind to VEGF R2 and/or VEGF R3. In another embodiment, the antibody or antigen-binding fragment thereof does not bind to a mouse or monkey Flt-1.

In another aspect, the invention provides an isolated antibody or antigen-binding fragment thereof that recognizes a peptide comprising an amino acid sequence corresponding to positions 139 to 148, positions 139 to 153, positions 178 to 206, positions 199 to 204 and positions 128 to 138 of SEQ ID NO:90, or a fragment thereof. In one embodiment the peptide consists of the amino acid sequence corresponding to positions 130 to 138, positions 141 to 148, positions 141 to 153 and positions 193 to 206 of SEQ ID NO:90.

In another aspect, the invention provides an isolated antibody or antigen-binding fragment thereof that competes with any anti-Flt-1 antibody or antigen-binding fragment thereof.

In another aspect, the invention provides pharmaceutical compositions comprising anti-Flt-1 antibodies or antigen-binding fragments thereof and a pharmaceutically acceptable carrier.

In yet another aspect, the invention provides polynucleotides encoding a CDR, a VL region, a VH region, a light chain, and/or a heavy chain of the antibody or antigen-binding fragment thereof of the invention. In one embodiment, the invention provides expression vectors comprising the polynucleotides. In yet another embodiment, the invention provides a host cell comprising the polynucleotide or the expression vector. In a particular embodiment, the invention provides methods of making an antibody or antigen-binding fragment thereof that specifically binds to human Flt-1 comprising culturing the host cell. In another embodiment, a hybridoma cell produces the antibody or antigen-binding fragment thereof.

In another aspect, the invention provides methods for treating a Flt-1-mediated disease, disorder or condition comprising administering to a subject in need of treatment an anti-Flt-1 antibody or antigen-binding fragment thereof. In a particular embodiment, the Flt-1-mediated disease, disorder or condition is Duchenne muscular dystrophy, Becker muscular dystrophy, bronchopulmonary dysplasia, preeclampsia or chronic kidney disease.

In another aspect, the method provides methods of treating Duchenne Muscular Dystrophy (DMD), the method comprising administering to a subject who is suffering from or susceptible to DMD an effective amount of an anti-Flt-1 antibody or antigen-binding fragment thereof, such that at least one symptom or feature of DMD is reduced in intensity, severity, or frequency, or has delayed onset. In one embodiment the method further comprises administering to the subject one or more additional therapeutic agents. In a particular embodiment the additional therapeutic agents are selected from the group consisting of prednisone, deflazacort, follistatin, RNA modulating therapeutics, exon-skipping therapeutics and gene therapy.

In one embodiment, the antibody or antigen-binding fragment thereof is administered parenterally. In some embodiments, the parenteral administration is selected from intravenous, intradermal, intrathecal, inhalation, transdermal (topical), intraocular, intramuscular, subcutaneous, and/or transmucosal administration. In a particular embodiment, the parenteral administration is intravenous administration. In yet another embodiment, the parenteral administration is subcutaneous administration.

In some embodiments, the antibody or antigen-binding fragment thereof is administered daily, twice weekly, weekly or monthly. In a particular embodiment antibody or antigen-binding fragment thereof is administered twice weekly.

In another embodiment, the effective amount of the antibody or antigen-binding fragment thereof is a dose amount of approximately 1 mg/kg to 50 mg/kg. In a particular embodiment the dose amount is approximately 1 mg/kg, 3 mg/kg or 10 mg/kg.

In one embodiment, the administration of the antibody or antigen-binding fragment thereof results in reduced fibrosis and/or necrosis relative to a control. In another embodiment, the administration of the antibody or antigen-binding fragment thereof results in improved angiogenesis in muscle of the subject relative to a control. In another embodiment the improved angiogenesis is reflected by increased blood flow on muscle pathology, increased VEGF levels in serum, decreased creatine kinase (CK) levels in serum, increased CD31 score by IHC, and/or reduced sFlt-1 levels in serum. In yet another embodiment, the administration of the antibody or antigen-binding fragment thereof results in improved muscle function relative to a control. In yet another embodiment, the improved muscle function is reflected by improved muscle force and/or resistance to fatigue.

In another aspect, the invention provides for a method of treating tissue fibrosis comprising administering to a subject in need of treatment an effective amount of an anti-Flt-1 antibody or antigen-binding fragment thereof.

BRIEF DESCRIPTION OF FIGURES

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 6B shows exemplary results of quantification of the CD31 positive area as a percentage of the total stained area in tissue sections obtained from the tibialis anterior (TA) muscle of mdx mice administered an anti-Flt-1 antibody.

FIGS. 30A-30C show exemplary results of quantification of the percent positivity of CD31 staining in tissue sections obtained from the diaphragm, gastrocnemius and tibialis muscle of mdx mice administered anti-Flt-1 antibody 21B3 or vehicle control antibody for 6 or 12 weeks.

FIGS. 38A-3E show exemplary results depicting MS/MS spectra for identified peptides containing amino acid residues from epitope regions.

DEFINITIONS

Figure 1A:
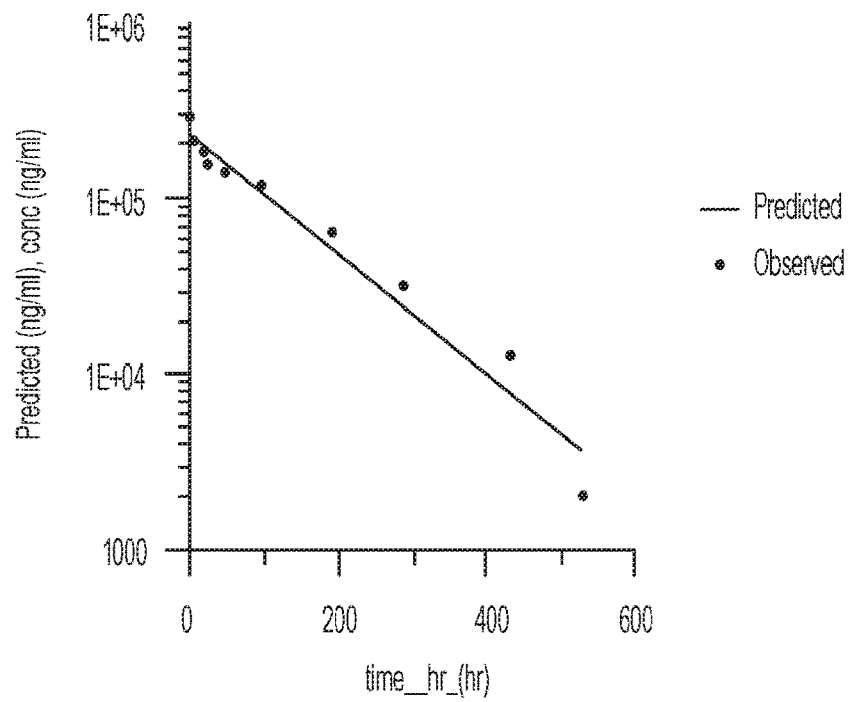
FIG. 1A shows exemplary results depicting clearance of anti-Flt-1 antibody 13B4 after mice were administered the antibody at a dose of 10 mg/kg intravenously.

In order for the present invention to be more readily understood, certain terms are first defined below. Additional definitions for the following terms and other terms are set forth throughout the specification.

Affinity: As is known in the art, "affinity" is a measure of the tightness with a particular ligand binds to its partner. In some embodiments, the ligand or partner is Flt-1. In some embodiments, the ligand or partner is soluble Flt-1. In some embodiments, the ligand or partner is a recombinant Flt-1. In a particular embodiment the ligand or partner is human sFlt-1. In a particular embodiment, the ligand or partner is a recombinant sFlt-1. In other embodiments, the ligand or partner is an anti-Flt-1 antibody. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Affinity matured (or affinity matured antibody): As used herein, the term "affinity matured" or "affinity matured antibody", refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al., BioTechnology 10:779-783 (1992) describes affinity maturation by $V_H$ and $V_L$ domain shuffling. Random mutagenesis of CDR and/or framework residues is described by: Barbas et al. Proc. Nat. Acad. Sci. U.S.A. 91:3809-3813 (1994); Schier et al., Gene 169: 147-155 (1995); Yelton et al., J. Immunol. 155: 1994-2004 (1995); Jackson et al., J. Immunol. 154(7):3310-9 (1995); and Hawkins et al., J. Mol. Biol. 226:889-896 (1992).

Amelioration: As used herein, the term "amelioration" is meant the prevention, reduction or palliation of a state, or improvement of the state of a subject. Amelioration includes, but does not require complete recovery or complete prevention of a disease condition.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin-binding domain. Such proteins may be derived from natural sources, or partly or wholly synthetically produced. An antibody may be monoclonal or polyclonal. An antibody may be a member of any immunoglobulin isotype, including any of the human isotypes: IgG, IgM, IgA, IgD, and IgE. In certain embodiments, an antibody may be a member of the IgG immunoglobulin class (e.g., IgG1, IgG2, IgG3, etc). In some embodiments, an antibody may be a human antibody. In some embodiments, an antibody may be a humanized antibody.

As is known by those of ordinary skill in the art, antibodies produced in nature are typically comprised of four polypeptide chains, two heavy (H) chains and two light (L) chains interconnected by disulfide bonds. Each heavy and light chain is comprised of a variable region (abbreviated herein as HCVR, VH or $V_H$ and LCVR, VL or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, $C_L$. The $V_H$ and $V_L$ regions further contain regions of hypervariability, termed complementarity determining regions (CDRs), interspersed with regions that are more conserved, which are termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The binding regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antigen-binding portion: As used herein, the term "antigen-binding portion" or "antigen-binding fragment" refers to one or more fragments or portions of an antibody that retain the ability to specifically bind to an antigen (e.g., Flt-1). Examples of antigen-binding portions include (i) a Fab fragment, a monovalent fragment consisting of the $V_H$, $V_L$, $C_H1$ and $C_L$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al., (1989) Nature 341:544-546), which comprises a single variable domain; (vi) an isolated complementarity determining region (CDR); (vii) a Fab' fragment, which is essentially a Fab with part of the hinge region; (viii) a nanobody, a heavy chain variable region containing a single variable domain and two constant domains. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). An antigen-binding fragment of an antibody may optionally comprise a single chain antibody fragment. Alternatively or additionally, an antigen-binding fragment of an antibody may comprise multiple chains which are linked together, for example, by disulfide linkages. An antigen-binding fragment of an antibody may optionally comprise a multimolecular complex. A functional antibody fragment typically comprises at least about 50 amino acids and more typically comprises at least about 200 amino acids.

In some embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen.

Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, and recombinant production. The fragments are screened for utility in the same manner as are intact antibodies.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Carrier or diluent: As used herein, the terms "carrier" and "diluent" refer to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

CDR: As used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Chimeric antibody: as used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody."

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Dysfunction: As used herein, the term "dysfunction" refers to an abnormal function. Dysfunction of a molecule (e.g., a protein) can be caused by an increase or decrease of an activity associated with such molecule. Dysfunction of a molecule can be caused by defects associated with the molecule itself or other molecules that directly or indirectly interact with or regulate the molecule.

Epitope: as used herein, includes any moiety that is specifically recognized by an immunoglobulin (e.g., antibody, antibody fragment thereof, receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, Va.). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

Framework or framework region: As used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Half-Life: As used herein, the term "half-life" is the time required for a quantity such as protein concentration or activity to fall to half of its value as measured at the beginning of a time period.

High affinity: As used herein, the term "high affinity", when referring an IgG type antibody, refers to an antibody having a $K_D$ of $10^{-8}$ M or less, more preferably $10^{-9}$ M or less and even more preferably $10^{-10}$ M or less for a domain of Flt-1. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

Human antibody: As used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

Human monoclonal antibody: As used herein, is intended to refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heave chain transgene and a light chain transgene fused to an immortalized cell.

Humanized: As is known in the art, the term "humanized" is commonly used to refer to antibodies (or antibody components) whose amino acid sequence includes $V_H$ and $V_L$ region sequences from a reference antibody raised in a non-human species (e.g., a mouse, a llama), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody (e.g., a mouse, a llama). A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

Hypertrophy: As used herein, the term "hypertrophy" refers to the increase in volume of an organ or tissue due to the enlargement of its component cells.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

Inhibition: As used herein, the terms "inhibition," "inhibit" and "inhibiting" refer to processes or methods of decreasing or reducing activity and/or expression of a protein or a gene of interest. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated Antibody: As used herein, the term "isolated antibody" is intended to refer to an antibody that is substantially free of other antibodies having different antigenic specificities (e.g., an isolated antibody that specifically binds to Flt-1). Moreover, an isolated antibody may be substantially free of other cellular material and/or chemicals.

$K_a$: As used herein, refers to the association rate of a particular antibody-antigen interaction, whereas the term "$K_d$," as used herein, is intended to refer to the dissociation rate of a particular antibody-antigen interaction. The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art. A preferred method for determining the $K_D$ of an antibody is by using surface plasmon resonance, preferably using a biosensor system such as a BIAcore® system.

Light-chain reshuffling: As used herein, the term "light-chain reshuffling" is intended to refer to an affinity maturation step where the heavy chain sequence is kept constant and a library of light chain sequences is generated. The light chain library is screened against the heavy chain to identify antibodies with improved binding affinity. The improved binding affinity may be in the nanomolar or picomolar ranges.

Monoclonal antibody: As used herein, the term "monoclonal antibody" is intended to refer to a preparation of antibody molecules of a single molecular composition. A monoclonal antibody composition displays a single binding specificity and affinity for a particular epitope.

Pharmaceutically acceptable: As used herein, the term "pharmaceutically acceptable" refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, the term "polypeptide" refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: As used herein, the term "protein" refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., DMD). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., DMD). In some embodiments a reference sample or group of reference samples are from individuals comparable to a particular individual. In some embodiments, relative risk is 0, 1, 2, 3, 4, 5, 6, 7, 8, 9, 10, or more.

Selective binding: As used herein, "selective binding", "selectively binds" "specific binding", or "specifically binds" refers, with respect to a binding moiety and a target, preferential association of a binding moiety to a target and not to an entity that is not the target. A certain degree of non-specific binding may occur between a binding moiety and a non-target. In some embodiments, a binding moiety selectively binds a target if binding between the binding moiety and the target is greater than 2-fold, greater than 5-fold, greater than 10-fold, or greater than 100-fold as compared with binding of the binding moiety and a non-target. In some embodiments, a binding moiety selectively binds a target if the binding affinity is less than about $10^{-5}$ M, less than about $10^{-6}$ M, less than about $10^{-7}$ M, less than about $10^{-8}$ M, or less than about $10^{-9}$ M.

Striated muscle: As used herein, the term "striated muscle" refers to multinucleated muscle tissue with regular arrangement of their intracellular contractile units, sarcomeres, leading to the appearance of striations using microscopy and under voluntary control. Typically, striated muscle can be cardiac muscle, skeletal muscle, and Branchiomeric muscles.

Smooth muscle: As used herein, the term "smooth muscle" refers to involuntarily controlled, non-striated muscle, including unitary and multi-unit muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols (Methods in Molecular Biology*, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols (Methods in Molecular Biology*, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Surface plasmon resonance: as used herein, refers to an optical phenomenon that allows for the analysis of specific binding interactions in real-time, for example through detection of alterations in protein concentrations within a biosensor matrix, such as by using a Biacore system (Pharmacia Biosensor AB, Uppsala, Sweden and Piscataway, N.J.). For further descriptions, see Jonsson, U., et al. (1993) Ann. Biol. Clin. 51: 19-26; Jonsson, U., et al. (1991) Biotechniques 11:620-627; Johnsson, B., et al. (1995) J. Mol. Recognit. 8: 125-131; and Johnnson, B., et al. (1991) Anal. Biochem. 198:268-277.

Suffering from: An individual who is "suffering from" a disease, disorder, and/or condition has been diagnosed with or displays one or more symptoms of the disease, disorder, and/or condition such as, for example DMD.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, DMD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target tissues: As used herein, the term "target tissues" refers to any tissue that is affected by a disease to be treated such as DMD. In some embodiments, target tissues include those tissues that display disease-associated pathology, symptom, or feature, including but not limited to muscle wasting, skeletal deformation, cardiomyopathy, muscle ischemia, cognitive impairment, and impaired respiratory function. In some embodiment the target tissue is smooth muscle, striated muscle or cardiac muscle.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition, such as for example, DMD. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for treating muscular dystrophy, including Duchenne muscular dystrophy (DMD) and/or Becker Muscular Dystrophy, based on the use of anti-Flt-1 antibodies, or antigen-binding fragments thereof, as therapeutics for treating muscular dystrophy. In some embodiments, the present invention provides methods of treating DMD including administering to an individual who is suffering from or susceptible to DMD a therapeutically effective amount of an anti-Flt-1 antibody, or antigen-binding fragment thereof, such that at least one symptom or feature of DMD is reduced in intensity, severity, or frequency, or has delayed onset.

Various aspects of the invention are described in detail in the following sections. The use of sections is not meant to limit the invention. Each section can apply to any aspect of the invention. In this application, the use of "or" means "and/or" unless stated otherwise.

Duchenne Muscular Dystrophy (DMD)

DMD is a disease characterized by progressive deterioration of muscles and loss of muscle related functions throughout the body. It is contemplated that the present invention provides methods and compositions for slowing, delaying or preventing deterioration of muscles, regenerating muscle and reversing, eliminating, delaying, preventing, or minimizing fibrosis, inflammation and other symptoms or features associated with DMD and other muscular dystrophies in various muscle tissues.

Muscle Tissues

There are two major types of muscle tissue in an animal, striated muscle and smooth muscle. As used herein, the term "striated muscle" refers to muscle tissues containing repeating sarcomeres. Striated muscle tends to be under voluntary control and attached to the skeleton. Striated muscle allows for voluntary movement of the body and includes the major muscle groups including the quadriceps, gastrocnemius, biceps, triceps, trapezius, deltoids, and many others. Striated muscle tends to be very long and, many striated muscles are able to function independently. Some striated muscle, however, is not attached to the skeleton, including those in the mouth, anus, heart, and upper portion of the esophagus.

Smooth muscle, on the other hand, has very different structure. Rather than a series of long muscles with separate skeletal attachments, smooth muscle tends to be organized into continuous sheets with mechanical linkages between smooth muscle cells. Smooth muscle is often located in the walls of hollow organs and is usually not under voluntary control. Smooth muscles lining a particular organ must bear the same load and contract concurrently. Smooth muscle functions, at least in part, to handle changes in load on hollow organs caused by movement and/or changes in posture or pressure. This dual role means that smooth muscle must not only be able to contract like striated muscle, but also that it must be able to contract tonically to maintain organ dimensions against sustained loads. Examples of smooth muscles are those lining blood vessels, bronchioles, bladder, and gastrointestinal tract such as rectum.

The strength of a muscle depends on the number and sizes of the muscle's cells and on their anatomic arrangement. Increasing the diameter of a muscle fiber either by synthesis of new myofibrils (hypertrophy) and/or the formation of more muscle cells (hyperplasia) will increase the force-generating capacity of the muscle.

Muscles may also be grouped by location or function. In some embodiments, an Flt-1 antibody or antigen-binding fragment thereof is targeted to one or more muscles of the face, one or more muscles for mastication, one or more muscles of the tongue and neck, one or more muscles of the thorax, one or more muscles of the pectoral girdle and arms, one or more muscles of the arm and shoulder, one or more ventral and dorsal forearm muscles, one or more muscles of the hand, one or more muscles of the erector spinae, one or more muscles of the pelvic girdle and legs, and/or one or more muscles of the foreleg and foot.

In some embodiments, muscles of the face include, but are not limited to, intraocular muscles such as ciliary, iris dilator, iris sphincter; muscles of the ear such as auriculares, temporoparietalis, stapedius, tensor tympani; muscles of the nose such as procerus, nasalis, dilator naris, depressor septi nasi, levator labii superioris alaeque nasi; muscles of the mouth such as levator anguli oris, depressor anguli oris, orbicularis oris, Buccinator, Zygomaticus Major and Minor, Platysma, Levator Labii Superioris, Depressor Labii Inferioris, Risorius, Mentalis, and/or Corrugator Supercilii.

In some embodiments, muscles of mastication include, but are not limited to, Masseter, Temporalis, Medial Pterygoid, Lateral Pterygoid. In some embodiments, muscles of the tongue and neck include, but are not limited to, Genioglossus, Styloglossus, Palatoglossus, Hyoglossus, Digastric, Stylohyoid, Mylohyoid, Geniohyoid, Omohyoid, Sternohyoid, Sternothyroid, Thyrohyoid, Sternocleidomastoid, Anterior Scalene, Middle Scalene, and/or Posterior Scalene.

In some embodiments, muscles of the thorax, pectoral girdle, and arms include, but are not limited to, Subclavius Pectoralis major, Pectoralis minor, Rectus abdominis, External abdominal oblique, Internal abdominal oblique, Transversus Abdominis, Diaphragm, External Intercostals, Internal Intercostals, Serratus Anterior, Trapezius, Levator Scapulae, Rhomboideus Major, Rhomboideus Minor, Latissimus dorsi, Deltoid, subscapularis, supraspinatus, infraspinatus, Teres major, Teres minor, and/or Coracobrachialis.

In some embodiments, muscles of the arm and shoulder include, but are not limited to, Biceps brachii-Long Head, Biceps brachii-Short Head, Triceps brachii-Long Head, Triceps brachii Lateral Head, Triceps brachii-Medial Head, Anconeus, Pronator teres, Supinator, and/or Brachialis.

In some embodiments, muscles of the ventral and dorsal forearm include, but are not limited to, Brachioradialis, Flexor carpi radialis, Flexor carpi ulnaris, Palmaris longus, Extensor carpi ulnaris, Extensor carpi radialis longus, Extensor carpi radialis brevis, Extensor digitorum, Extensor digiti minimi.

In some embodiments, muscles of the hand include, but are not limited to intrinsic muscles of the hand such as thenar, abductor pollicis brevis, flexor pollicis brevis, opponens pollicis, hypothenar, abductor digiti minimi, the flexor digiti minimi brevis, opponens digiti minimi, palmar interossei, dorsal interossei and/or lumbricals.

In some embodiments, muscles of the erector spinae include, but are not limited to, cervicalis, spinalis, longissimus, and/or iliocostalis.

In some embodiments, muscles of the pelvic girdle and the legs include, but are not limited to, Psoas Major, Iliacus, quadratus femoris, Adductor longus, Adductor brevis, Adductor magnus, Gracilis, Sartorius, Quadriceps femoris such as, rectus femoris, vastus lateralis, vastus medialis, vastus intermedius, Gastrocnemius, Fibularis (Peroneus) Longus, Soleus, Gluteus maximus, Gluteus medius, Gluteus minimus, Hamstrings: Biceps Femoris: Long Head, Hamstrings: Biceps Femoris: Short Head, Hamstrings: Semitendinosus, Hamstrings: Semimembranosus, Tensor fasciae latae, Pectineus, and/or Tibialis anterior.

In some embodiments, muscles of the foreleg and foot include, but are not limited to, Extensor digitorum longus, Extensor hallucis longus, peroneus brevis, plantaris, Tibialis posterior, Flexor hallucis longus, extensor digitorum brevis, extensor hallucis brevis, Abductor hallucis, flexor hallucis brevis, Abductor digiti minimi, flexor digiti minimi, opponens digiti minimi, extensor digitorum brevis, lumbricales of the foot, Quadratus plantae or flexor accessorius, flexor digitorum brevis, dorsal interossei, and/or plantar interossei.

Exemplary muscle targets are summarized in Table 1.

TABLE 1

| ORBICULARIS OCULI | | | |
|---|---|---|---|
| Intraocular: ciliary, iris dilator, iris sphincter | | | |
| Ear: auriculares, temporoparietalis, stapedius, tensor tympani | | | |
| Nose: procerus, nasalis, dilator naris, depressor septi nasi, levator labii superioris alaeque nasi | | | |
| Mouth: levator anguli oris, depressor anguli oris, orbicularis oris | | | |
| Buccinator | Zygomaticus Major and Minor | Platysma | Levator Labii Superioris |
| Depressor Labii Inferioris | Risorius | Mentalis | Corrugator Supercilii |
| Anconeus | Pronator teres | Supinator | Brachialis |
| MUSCLES OF MASTICATON | | | |
| Masseter | Temporalis | Medial Pterygoid | Lateral Pterygoid |
| MUSCLES OF THE TONGUE AND NECK | | | |
| Genioglossus | Styloglossus | Palatoglossus | Hyoglossus |
| Digastric | Stylohyoid | Mylohyoid | Geniohyoid |
| Omohyoid | Sternohyoid | Sternothyroid | Thyrohyoid |
| Sternocleidomastoid | Anterior Scalene | Middle Scalene | Posterior Scalene |
| MUSCLES OF THE THORAX, PECTORAL GIRDLE AND ARMS | | | |
| Subclavius | Pectoralis major | Pectoralis minor | Rectus abdominis |
| External abdominal oblique | Internal abdominal oblique | Transversus Abdominis | Diaphragm |
| External Intercostals | Internal Intercostals | Serratus Anterior | Trapezius |
| Levator Scapulae | Rhomboideus Major | Rhomboideus Minor | Latissimus dorsi |
| Deltoid | subscapularis | supraspinatus | infraspinatus |
| Teres major | Teres minor | Coracobrachialis | |

TABLE 1-continued

| ARM AND SHOULDER | | | |
|---|---|---|---|
| Biceps brachii-Long Head | Biceps brachii-Short Head | Triceps brachii-Long Head | Triceps brachii-Lateral Head |
| Triceps brachii-Medial Head | Anconeus | Pronator teres | Supinator |
| Brachialis | | | |

| FOREARM MUSCLES: Ventral and Dorsal | | | |
|---|---|---|---|
| Brachioradialis | Flexor carpi radialis | Flexor carpi ulnaris | Palmaris longus |
| Extensor carpi ulnaris | Extensor carpi radialis longus | Extensor carpi radialis brevis | Extensor digitorum |
| Extensor digiti minimi | erector spinae: cervicalis | erector spinae: spinalis | erector spinae: longissimus |
| erector spinae: iliocostalis | | | |
| Intrinsic Muscles of the Hand: thenar, abductor pollicis brevis, flexor pollicis brevis, and the opponens pollicis | | | |
| Intrinsic Muscles of the Hand: hypothenar, abductor digiti minimi, the flexor digiti minimi brevis, and the opponens digiti minimi | | | |
| Intrinsic Muscles of the Hand: palmar interossei, dorsal interossei and lumbricals | | | |

| MUSCLES OF THE PELVIC GIRDLE AND THE LEGS | | | |
|---|---|---|---|
| Iliopsoas: Psoas Major | Iliopsoas: Iliacus | quadratus femoris | Adductor longus |
| Adductor brevis | Adductor magnus | Gracilis | Sartorius |
| Quadriceps femoris: rectus femoris | Quadriceps femoris: vastus lateralis | Quadriceps femoris: vastus medialis | Quadriceps femoris: vastus intermedius |
| Gastrocnemius | Fibularis (Peroneus) Longus | Soleus | Gluteus maximus |
| Gluteus medius | Gluteus minimus | Hamstrings: Biceps Femoris: Long Head | Hamstrings: Biceps Femoris: Short Head |
| Hamstrings: Semitendinosus | Hamstrings: Semimembranosus | Tensor fasciae latae | Pectineus |
| Tibialis anterior | | | |

| MUSCLES OF THE FORELEG AND FOOT | | | |
|---|---|---|---|
| Extensor digitorum longus | Extensor hallucis longus | peroneus brevis | plantaris |
| Tibialis posterior | Flexor hallucis longus | extensor digitorum brevis | extensor hallucis brevis |
| Abductor hallucis opponens digiti minimi | flexor hallucis brevis extensor digitorum brevis | Abductor digiti minimi lumbricales of the foot | flexor digiti minimi Quadratus plantae or flexor accessorius |
| Flexor digitorum brevis | dorsal interossei | plantar interossei | |

Muscular Dystrophy

Muscular dystrophies are a group of inherited disorders that cause degeneration of muscle, leading to weak and impaired movements. A central feature of all muscular dystrophies is that they are progressive in nature. Muscular dystrophies include, but are not limited to: Duchenne muscular dystrophy (DMD), Becker muscular dystrophy, Emery-Dreifuss muscular dystrophy, facioscapulohumeral muscular dystrophy, limb-girdle muscular dystrophies, and myotonic dystrophy Types 1 and 2, including the congenital form of Myotonic dystrophy Type 1. Symptoms may vary by type of muscular dystrophy with some or all muscles being affected. Exemplary symptoms of muscular dystrophies include delayed development of muscle motor skills, difficulty using one or more muscle groups, difficulty swallowing, speaking or eating, drooling, eyelid drooping, frequent falling, loss of strength in a muscle or group of muscles as an adult, loss in muscle size, problems walking due to weakness or altered biomechanics of the body, and/or cognitive or behavioral impairment/mental retardation.

While there are no known cures for muscular dystrophies, several supportive treatments are used which include both symptomatic and disease modifying therapies. Corticosteroids, ACE inhibitors, Angiotensin receptor blockers, physical therapy, orthotic devices, wheelchairs, or other assistive medical devices for ADLs and pulmonary function are commonly used in muscular dystrophies. Cardiac pacemakers are used to prevent sudden death from cardiac arrythmias in Myotonic dystrophy. Anti-myotonic agents which improve the symptoms of myotonia (inability to relax) include mexilitine, and in some cases phenytoin, procainamide and quinine.

Duchenne Muscular Dystrophy

Duchenne muscular dystrophy (DMD) is a recessive X-linked form of muscular dystrophy which results in muscle degeneration and eventual death. DMD is characterized by weakness in the proximal muscles, abnormal gait, hypertrophy in the gastrocnemius (calf) muscles, and elevated creatine kinase. Many DMD patients are diagnosed around the age of 5, when symptoms/signs typically become more obvious. Affected individuals typically stop walking around age 10-13 and die in or before their mid to late 20's due to respiratory complications and cardiomyopathy.

In individuals affected with DMD, serum creatine kinase levels may be increased by greater than 10-fold as compared to unaffected individuals. In some embodiments, administering the provided composition to an affected individual results in a reduced serum creatine kinase level as compared to the baseline level before treatment. Typically, the baseline level is measured immediately before treatment. In some embodiments, administering the provided composition results in a reduced serum creatine kinase level by at least about 10%, 20%, 30%, 40%, 50%, 60%, 70%, 80%, 90%, or 95% as compared to the baseline serum creatine kinase level immediately before treatment. In some embodiments, administering the provided composition results in a reduced serum creatine kinase level to less than about 3500 IU/L, 3000 IU/L, 2500 IU/L, 2000 IU/L, 1500 IU/L, 1000 IU/L, 750 IU/L, 500 IU/L, 250 IU/L, 100 IU/L, 90 IU/L, 80 IU/L, 70 IU/L or 60 IU/L. In some embodiments, administering the provided composition results in a reduced serum creatine kinase level as compared to the serum creatine kinase level in subjects who are not treated.

The disorder DMD is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemmal membrane tearing and necrosis of muscle fibers. While both sexes can carry the mutation, females rarely exhibit severe signs of the disease.

A main symptom of DMD is muscle weakness associated with muscle wasting with the voluntary muscles being first affected typically, especially affecting the muscles of the hips, pelvic area, thighs, shoulders, and calf muscles. Muscle weakness also occurs in the arms, neck, and other areas. Calves are often enlarged. Signs and symptoms usually appear before age 6 and may appear as early as infancy. Cardiomyopathy occurs in individuals with DMD usually after the age of 18. Other physical symptoms include, but are not limited to, delayed ability to walk independently, progressive difficulty in walking, stepping, or running, and eventual loss of ability to walk (usually by the age of 12); frequent falls; fatigue; difficulty with motor skills (running, hopping, jumping); increased lumbar lordosis, leading to shortening of the hip-flexor muscles; impaired functionality of achilles tendon and hamstrings, fibrosis in connective tissue; muscle fiber deformities; pseudohypertrophy (enlarging) of tongue and calf muscles caused by replacement of muscle tissue by fat and connective tissue; higher risk of neurobehavioral disorders (e.g., ADHD), learning disorders (dyslexia), and non-progressive weaknesses in specific cognitive skills (in particular short-term verbal memory); skeletal deformities (including scoliosis in some cases).

The changes in muscle seen in DMD are accompanied by an increase in connective tissue, i.e., the development of fibrosis, and result from either reactive or reparative processes involving mechanical, humoral and or cellular factors. Lack of functional dystrophin leads to instability of muscle fiber membranes, and as a result, the cells are less resistant to mechanical shear and prone to excess influx of electrolytes resulting in tissue damage. As muscle tissue in DMD is damaged, recovery is limited by the ability of satellite cells to proliferate. This leads to necrosis, inflammation, fibrosis and fatty cell replacement. The increase in connective tissue occurs early in the disease process as areolar connective tissue that ensheaths each myocyte and overlays the sarcolemma (i.e., the endomysium) increases prior to observable muscle damage. The increase in collagenous connective tissue is a factor in muscle pathology in DMD, adversely affecting the supply of nutrients to the affected myocyte, and secondarily affecting muscle strength and age of loss of ambulation.

In some embodiments, administration of an anti-Flt-1 antibody, or antigen-binding fragment thereof, in vivo results in decreased fibrosis of muscle tissue. In some embodiments the muscle is skeletal muscle. In particular embodiments, the muscle is the cardiac muscle, diaphragm muscle, gastrocnemius muscle and/or tibialis anterior (TA) muscle. In some embodiments, the decreased fibrosis is demonstrated by decreased collagen staining. In some embodiments, the collagen in Type I collagen. In some embodiments, the decreased fibrosis may be measured, for example, by measuring the percent collagen positive area in muscle of mice administered the anti-Flt-1 antibody, or antigen-binding fragment thereof. For example, the percent collagen positive area in the diaphragm muscle of mice administered the anti-Flt-1 antibody, or antigen-binding fragment thereof, may be at least about 3.0%, about 3.5%, about 4.0%, about 4.5%, about 5.0%, about 5.5%, about 6.0%, about 6.5%, about 7.0%, about 7.5%, about 8.0%, about 8.5% or about 9.0% of the total tissue area. In a particular embodiment, the percent collagen positive area in the diaphragm muscle of mice administered the anti-Flt-1 antibody may be significantly lower than the percent collagen positive area in the diaphragm muscle of mice administered an isotype control antibody.

In some embodiments, administration of an anti-Flt-1 antibody, or antigen-binding fragment thereof, in vivo results in decreased necrosis of muscle tissue. In some embodiments the muscle is skeletal muscle. In particular embodiments, the muscle is the cardiac muscle, diaphragm muscle, gastrocnemius muscle and/or tibialis anterior (TA) muscle. In some embodiments, the decreased necrosis may be measured, for example, by measuring the percent necrosis positive area in muscle of mice administered the anti-Flt-1 antibody, or antigen-binding fragment thereof. For example, the percent necrosis positive area in the gastrocnemius muscle of mice administered the anti-Flt-1 antibody, or antigen-binding fragment thereof may be at least about 0.5%, about 0.45%, about 0.4%, about 0.35%, about 0.3%, about 0.25%, about 0.2%, about 0.15%, about 0.1%, about 0.05%, or about 0.025% of the total tissue area. In a particular embodiment, the percent necrosis positive area in the gastrocnemius muscle of mice administered the anti-Flt-1 antibody may be significantly lower than the percent necrosis positive area in the gastrocnemius muscle of mice administered an isotype control antibody.

In some embodiments, administration of an anti-Flt-1 antibody, or antigen-binding fragment thereof, in vivo results in increased muscle force and/or resistance to fatigue.

Flt-1 Receptor

Flt-1 receptor, also known as vascular endothelial growth factor receptor 1 (VEGFR-1) or Flt-1, is a receptor that is encoded by the FLT1 gene and expressed on endothelia cell and monocyte cell membranes. The vascular endothelial growth factor (VEGF) family of signal glycoproteins act as potent promoters of angiogenesis during embryogenesis and postnatal growth. Specifically, the binding of the VEGF-A ligand with the VEGF receptors has been shown to promote vascular permeability and also trigger endothelial cell migration, proliferation, and survival, and the newly formed endothelial cells provide the basic structure of new vasculatures. The dominant VEGF signal molecule for angiogenesis, VEGF-A, mediates its signal through VEGF receptor-1 (VEGFR-1, also known as Flt-1) and VEGF receptor-2 (VEGFR-2, also known as Flk-1). A soluble form of Flt-1 (sFlt-1) also exists, but lacks an intracellular signaling domain and thus is believed to only serve in a regulatory capacity by sequestering VEGF-A or other ligands that bind to it. sFlt-1 and other molecules containing Flt-1 binding sites that are not linked to an intracellular signal transduction pathway are referred to as "decoy receptors". Flt-1 and Flk-1 receptors contain an extracellular VEGF-A-binding domain and an intracellular tyrosine kinase domain, and both show expression during the developmental stage and tissue regeneration in hemangioblasts and endothelial cell lineages. Flt-1 has about 10 times greater binding affinity for VEGF-A ($K_d$~$2^{-10}$ pM) compared to Flk-1, but weaker tyrosine kinase activity indicates that angiogenic signal transduction following VEGF-A binding to Flt-1 is comparably weaker than that resulting from VEGF-A binding to Flk-1. As such, homozygous Flt-1 gene knockout mice die in the embryonic stage from endothelial cell overproduction and blood vessel disorganization. Inversely, homozygous Flk-1 gene knockout mice die from defects in the development of organized blood vessels due to lack of yolk-sac blood island formation during embryogenesis. Both the Flt-1 and Flk-1 receptors are needed for normal development, but selective augmentation in VEGF-A concentration may allow for greater binding to the Flk-1 receptor and induce a pro-angiogenic effect that increases capillary density and facilitates regeneration of muscle, reduction of fibrosis and inflammation, and mitigation of symptoms and features associated with DMD and other muscular dystrophies in various muscle tissues.

As used herein, the term "Flt-1 receptor" refers to both soluble and membrane associate Flt-1 receptors, or functional fragments thereof.

Anti-Flt-1 Antibodies

As used herein, the term "anti-Flt-1 antibodies" refers to any antibodies, or antigen-binding fragments thereof, that bind to a Flt-1 receptor (e.g., soluble or membrane associated Flt-1 receptor). In some embodiments, anti-Flt-1 antibodies are produced that bind with high affinity to Flt-1 receptors. Without wishing to be bound by theory, it is believed that anti-Flt-1 antibody binding to Flt-1 receptors inhibits one or more endogenous ligands from binding to Flt-1 and thereby allowing a greater amount of available ligand to associate with other VEGF receptors, such as the Flk-1 receptor. Increased availability of VEGF promotes angiogenesis with increased blood flow to muscle to combat functional ischemia and leading to improvements in structural and functional characteristics of DMD. In some embodiments, antibody binding to Flt-1 receptors increases the amount of VEGF available to bind to other VEGF receptors.

In some embodiments the anti-Flt-1 antibody or antigen-binding fragment thereof comprises the sequences provided in Table 2.

TABLE 2

| Heavy Chain Variable Region | CDR1 | CDR2 | CDR3 |
|---|---|---|---|
| IGHV3-23*01 | SYAMS (SEQ ID NO: 1) | AISGSGGSTYYADSVKG (SEQ ID NO: 5) | --------------DY (SEQ ID NO: 15) |
| IGHV3-23*04 | SYAMS (SEQ ID NO: 1) | AISGSGGSTYYADSVKG (SEQ ID NO: 5) | --------------DY (SEQ ID NO: 15) |
| 13B4_VH | DYSMS (SEQ ID NO: 2) | AISWNGDSTYYAESMKG (SEQ ID NO: 6) | SWATPIESLYYYGMDY (SEQ ID NO: 16) |
| 27H4_VH (97.6_1.0 | DYSMS (SEQ ID NO: 2) | AISWNGDSTYYAESLKG (SEQ ID NO: 7) | SWATPIESLYYYGSDY (SEQ ID NO: 17) |
| 27H9_VH (97.5_1.1 | DYSMS (SEQ ID NO: 2) | AISWNGDSTYYAESAKG (SEQ ID NO: 8) | SWATPIESLYYYGSDY (SEQ ID NO: 17) |
| 25D4_VH (97.0_0.9 | DYSAS (SEQ ID NO: 3) | AISWNGDSTYYAESVKG (SEQ ID NO: 9) | SWATPIESLYYYGSDY (SEQ ID NO: 17) |
| 25G9_VH (97.0_0.9 | DYSMS SEQ ID NO: 2) | AITWSGDSTYYAESVKG (SEQ ID NO: 10) | SWATPIESLYYYGTDY (SEQ ID NO: 18) |
| 25F11_VH (97.5_1. | DYSMS (SEQ ID NO: 2) | AISWNGDSTYYAESAKG (SEQ ID NO: 8) | SWATPIESLYYYGSDY (SEQ ID NO: 17) |
| 29E2_VH (96.3_1.1 | DYSLS (SEQ ID NO: 4) | AISWNGDSTYYAESVKG (SEQ ID NO: 9) | SWATPIESLYYYGSDY (SEQ ID NO: 17) |
| 27G9_VH (96.3_1.3 | DYSAS (SEQ ID NO: 3) | AISWSGDSTYYAESLKG (SEQ ID NO: 11) | SWATPIESLYYYGSDY (SEQ ID NO: 17) |
| 27H6_VH (97.5 | DYSAS (SEQ ID NO: 3) | AISWSGDSTYYAESVKG (SEQ ID NO: 12) | SWATPIESLYYYGSDY (SEQ ID NO: 17) |
| 27H9_NG/QG | DYSMS (SEQ ID NO: 2) | AISWQGDSTYYAESAKG (SEQ ID NO: 13) | SWATPIESLYYYGSDY (SEQ ID NO: 17) |
| 27H9_NG/NA | DYSMS (SEQ ID NO: 2) | AISWNADSTYYAESAKG (SEQ ID NO: 14) | SWATPIESLYYYGSDY (SEQ ID NO: 17) |
| 27H9_NA_+_AAA | DYSMS (SEQ ID NO: 2) | AISWNADSTYYAESAKG (SEQ ID NO: 14) | SWATPIESLYYYGSDY (SEQ ID NO: 17) |

TABLE 2-continued

| Light Chain Region Variable | CDR1 | CDR2 | CDR3 |
|---|---|---|---|
| IGLV3-9*01 | GGNNIGSKNVH (SEQ ID NO: 19) | RDSNRPS (SEQ ID NO: 22) | QV-------VV (SEQ ID NO: 25) |
| IGLV3-9*02 | GGNNLGYKSVH (SEQ ID NO: 20) | RDNNRPS (SEQ ID NO: 23) | QV-------VV (SEQ ID NO: 25) |
| LC_21B3 | GGNNIGSQTAQ (SEQ ID NO: 21) | ANNRRPS (SEQ ID NO: 24) | QVWDGSTQAIV (SEQ ID NO: 26) |
| VL_27H4 | GGNNIGSQTAQ (SEQ ID NO: 21) | ANNRRPS (SEQ ID NO: 24) | QVWEDSTQAIV (SEQ ID NO: 27) |
| VL_27H9 | GGNNIGSQTAQ (SEQ ID NO: 21) | ANNRRPS (SEQ ID NO: 24) | QVWDESTQAIV (SEQ ID NO: 28) |
| VL_25D4 | GGNNIGSQTAQ (SEQ ID NO: 21) | ANNRRPS (SEQ ID NO: 24) | QVWAASTQAIV (SEQ ID NO: 29) |
| VL_25G9 | GGNNIGSQTAQ (SEQ ID NO: 21) | ANNRRPS (SEQ ID NO: 24) | QVWDDSTQAIV (SEQ ID NO: 30) |
| VL_25F11 | GGNNIGSQTAQ (SEQ ID NO: 21) | ANNRRPS (SEQ ID NO: 24) | QVWEASTQAIV (SEQ ID NO: 31) |
| VL_29E2 | GGNNIGSQTAQ (SEQ ID NO: 21) | ANNRRPS (SEQ ID NO: 24) | QVWDASTQAIV (SEQ ID NO: 32) |
| VL_27G9 | GGNNIGSQTAQ (SEQ ID NO: 21) | ANNRRPS (SEQ ID NO: 24) | QVWEESTQAIV (SEQ ID NO: 33) |
| VL_27H6 | GGNNIGSQTAQ (SEQ ID NO: 21) | ANNRRPS (SEQ ID NO: 24) | QVWDGSTQAIV (SEQ ID NO: 26) |
| VL_27H6(DA) | GGNNIGSQTAQ (SEQ ID NO: 21) | ANNRRPS (SEQ ID NO: 24) | QVWDASTQAIV (SEQ ID NO: 32) |
| VL_27H6(EG) | GGNNIGSQTAQ (SEQ ID NO: 21) | ANNRRPS (SEQ ID NO: 24) | QVWEGSTQAIV (SEQ ID NO: 34) |

| Heavy Chain Variable Region | VH |
|---|---|
| IGHV3-23*01 | EVQLLESGGGLVQPGGSLRLSCAASGFTFS SYAMS WVRQAPGKGLEW VSAISGSGGSTYYADSVKG RFTISRDNSKNTLYLQMNSLRAEDTAVYY CAK --------------DY WGQGTLVTVSS (SEQ ID NO: 35) |
| IGHV3-23*04 | EVQLVESGGGLVQPGGSLRLSCAASGFTFS SYAMS WVRQAPGKGLEW VSAISGSGGSTYYADSVKG RFTISRDNSKNTLYLQMNSLRAEDTAVYY CAK --------------DY WGQGTLVTVSS (SEQ ID NO: 36) |
| 13B4_VH | ELQLVESGGGLVQPGGSLRLSCAASGFTFR DYSMS WVRQAPGKGLEW VSAISWNGDSTYYAESMKG RFTISRDNAKNTLYLQMNSLKSEDTAVYY CAK SWATPIESLYYYGMDY WGKGTLVTVSS (SEQ ID NO: 37) |
| 27H4_VH (97.6_1.0 | ELQLVESGGGLVQPGGSLRLSCAASGFTFR DYSMS WVRQAPGKGLEW VSAISWNGDSTYYAESLKG RFTISRDNAKNTLYLQMNSLRAEDTAVYY CAK SWATPIESLYYYGSDY WGQGTLVTVSS (SEQ ID NO: 38) |
| 27H9_VH (97.5_1.1 | EVQLLESGGGLVQPGGSLRLSCAASGFTFR DYSMS WVRQAPGKGLEW VSAISWNGDSTYYAESAKG RFTISRDNSKNTLYLQMNSLRAEDTAVYY CAK SWATPIESLYYYGSDY WGQGTLVTVSS (SEQ ID NO: 39) |
| 25D4_VH (97.0_0.9 | EVQLLESGGGLVQPGGSLRLSCAASGFTFR DYSAS WVRQAPGKGLEW VSAISWNGDSTYYAESVKG RFTISRDNAKNTLYLQMNSLRAEDTAVYY CAK SWATPIESLYYYGSDY WGQGTLVTVSS (SEQ ID NO: 40) |
| 25G9_VH (97.0_0.9 | EVQLLESGGGLVQPGGSLRLSCAASGFTFR DYSMS WVRQAPGKGLEW VSAITWSGDSTYYAESVKG RFTISRDNSKNTLYLQMNSLRAEDTAVYY CAK SWATPIESLYYYGTDY WGKGTLVTVSS (SEQ ID NO: 41) |

TABLE 2-continued

| | |
|---|---|
| 25F11_VH (97.5_1. | EVQLLESGGGLVQPGGSLRLSCAASGFTFR DYSMS WVRQAPGKGLEW VSAISWNGDSTYYAESAKG RFTISRDNSKNTLYLQMNSLRAEDTAVYY CAK SWATPIESLYYYGSDY WGQGTLVTVSS (SEQ ID NO: 42) |
| 29E2_VH (96.3_1.1 | EVQLVESGGGLVQPGGSLRLSCAASGFTFR DYSLS WVRQAPGKGLEW VSAISWNGDSTYYAESVKG RFTISRDNSKNTLYLQMNSLRAEDTAVYY CAK SWATPIESLYYYGSDY WGKGTLVTVSS (SEQ ID NO: 43) |
| 27G9_VH (96.3_1.3 | EVQLLESGGGLVQPGGSLRLSCAASGFTFR DYSAS WVRQAPGKGLEW VSAISWSGDSTYYAESLKG RFTISRDNSKNTLYLQMNSLRAEDTAVYY CAK SWATPIESLYYYGSDY WGKGTLVTVSS (SEQ ID NO: 44) |
| 27H6_VH (97.5 | ELQLVESGGGLVQPGGSLRLSCAASGFTFS DYSAS WVRQAPGKGLEW VSAISWSGDSTYYAESVKG RFTIFRDNSKNTLYLQMNSLRAEDTAVYY CAK SWATPIESLYYYGSDY WGQGTLVTVSS (SEQ ID NO: 45) |
| 27H9_NG/QG | EVQLLESGGGLVQPGGSLRLSCAASGFTFR DYSMS WVRQAPGKGLEW VSAISWQGDSTYYAESAKG RFTISRDNSKNTLYLQMNSLRAEDTAVYY CAK SWATPIESLYYYGSDY WGQGTLVTVSS (SEQ ID NO: 46) |
| 27H9_NG/NA | EVQLLESGGGLVQPGGSLRLSCAASGFTFR DYSMS WVRQAPGKGLEW VSAISWNADSTYYAESAKG RFTISRDNSKNTLYLQMNSLRAEDTAVYY CAK SWATPIESLYYYGSDY WGQGTLVTVSS (SEQ ID NO: 47) |
| 27H9_NA_+_AAA | EVQLLESGGGLVQPGGSLRLSCAASGFTFR DYSMS WVRQAPGKGLEW VSAISWNADSTYYAESAKG RFTISRDNSKNTLYLQMNSLRAEDTAVYY CAK SWATPIESLYYYGSDY WGQGTLVTVSS (SEQ ID NO: 48) |
| Light Chain Variable Region VL | |
| IGLV3-9*01 | SYELTQPLSVSVALGQTARITC GGNNIGSKNVH WYQQKPGQAPVLVIY RDSNRPS GIPERFSGSNSGNTATLTISRAQAGDEADYYC QV-------VV FGGGTKLTVL (SEQ ID NO: 49) |
| IGLV3-9*02 | SYELTQPLSVSVALGQAARITC GGNNLGYKSVH WYQQKPGQAPVLVIY RDNNRPS GIPERFSGSNSGNTATLTISRAQAGDEADYYC QV-------VV FGGGTKLTVL (SEQ ID NO: 50) |
| LC_21B3 | SYELTQSPSVSVALRQTAKITC GGNNIGSQTAQ WYQQKPGQAPVLVIY ANNRRPS GIPERFSGSKSGNTATLTISGAQAEDEADYYC QVWDGSTQAIV FGGGTHLTVL (SEQ ID NO: 51) |
| VL_27H4 | SYELTQPLSVSVALGQTARITC GGNNIGSQTAQ WYQQKPGQAPVLVIY ANNRRPS GIPERFSGSKSGNTATLTISRAQAEDEADYYC QVWEDSTQAIV FGGGTKLTVL (SEQ ID NO: 52) |
| VL_27H9 | SYELTQPLSVSVALRQTARITC GGNNIGSQTAQ WYQQKPGQAPVLVIY ANNRRPS GIPERFSGSKSGNTATLTISRAQAEDEADYYC QVWDESTQAIV FGGGTKLTVL (SEQ ID NO: 53) |
| VL_25D4 | SYELTQPLSVSVALGQTARITC GGNNIGSQTAQ WYQQKPGQAPVLVIY ANNRRPS GIPERFSGSKSGNTATLTISGAQAEDEADYYC QVWAASTQAIV FGGGTKLTVL (SEQ ID NO: 54) |
| VL_25G9 | SYELTQPLSVSVALRQAARITC GGNNIGSQTAQ WYQQKPGQAPVLVIY ANNRRPS GIPERFSGSKSGNTATLTISRAQAEDEADYYC QVWDDSTQAIV FGGGTKLTVL (SEQ ID NO: 55) |
| VL_25F11 | SYELTQPLSVSVALRQAARITC GGNNIGSQTAQ WYQQKPGQAPVLVIY ANNRRPS GIPERFSGSKSGNTATLTISRAQAEDEADYYC QVWEASTQAIV FGGGTKLTVL (SEQ ID NO: 56) |
| VL_29E2 | SYELTQSPSVSVALRQTAKITC GGNNIGSQTAQ WYQQKPGQAPVLVIY ANNRRPS GIPERFSGSKSGNTATLTISGAQAGDEADYYC QVWDASTQAIV FGGGTKLTVL (SEQ ID NO: 57) |
| VL_27G9 | SYELTQPLSVSVALGQTAKITC GGNNIGSQTAQ WYQQKPGQAPVLVIY ANNRRPS GIPERFSGSKSGNTATLTISRAQAEDEADYYC QVWEESTQAIV FGGGTHLTVL (SEQ ID NO: 58) |

TABLE 2-continued

| | |
|---|---|
| VL_27H6 | SYELTQPLSVSVALRQAAKITC GGNNIGSQTAQ WYQQKPGQAPVLVIY ANNRRPS GIPERFSGSKSGNTATLTISRAQAGDEADYYC QVWDGSTQAIV FGGGTKLTVL<br>(SEQ ID NO: 59) |
| VL_27H6(DA) | SYELTQPLSVSVALRQAAKITC GGNNIGSQTAQ WYQQKPGQAPVLVIY ANNRRPS GIPERFSGSKSGNTATLTISRAQAGDEADYYC QVWDASTQAIV FGGGTKLTVL<br>(SEQ ID NO: 60) |
| VL_27H6(EG) | SYELTQPLSVSVALRQAAKITC GGNNIGSQTAQ WYQQKPGQAPVLVIY ANNRRPS GIPERFSGSKSGNTATLTISRAQAGDEADYYC QVWEGSTQAIV FGGGTKLTVL<br>(SEQ ID NO: 61) |
| Heavy Chain | Heavy Chain Sequence (VH + CH1/2/3) |
| VH_27H6_DG/EG | ELQLVESGGGLVQPGGSLRLSCAASGFTFSDYSASWVRQAPGKGLEWVSAISWSGDSTY YAESVKGRFTIFRDNSKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK<br>(SEQ ID NO: 62) |
| VH_27H6_DG/DA | ELQLVESGGGLVQPGGSLRLSCAASGFTFSDYSASWVRQAPGKGLEWVSAISWSGDSTY YAESVKGRFTIFRDNSKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK<br>(SEQ ID NO: 63) |
| VH_27H9_NG/QG | EVQLLESGGGLVQPGGSLRLSCAASGFTFRDYSMSWVRQAPGKGLEWVSAISWQGDSTY YAESAKGRFTISRDNSKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK<br>(SEQ ID NO: 64) |
| VH_27H9_NG/NA | EVQLLESGGGLVQPGGSLRLSCAASGFTFRDYSMSWVRQAPGKGLEWVSAISWNADSTY YAESAKGRFTISRDNSKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK<br>(SEQ ID NO: 65) |
| VH_27H4_NG/QG | ELQLVESGGGLVQPGGSLRLSCAASGFTFRDYSMSWVRQAPGKGLEWVSAISWQGDSTY YAESLKGRFTISRDNAKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK<br>(SEQ ID NO: 66) |
| VH_27H4_NG/NA | ELQLVESGGGLVQPGGSLRLSCAASGFTFRDYSMSWVRQAPGKGLEWVSAISWNADSTY YAESLKGRFTISRDNAKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK<br>(SEQ ID NO: 67) |
| VH_27H4_NA_+_AAA | ELQLVESGGGLVQPGGSLRLSCAASGFTFRDYSMSWVRQAPGKGLEWVSAISWNADSTY YAESLKGRFTISRDNAKNTLYLQMNSLRAEDTAVYYCAKSWATPIESLYYYGSDYWGQG TLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPP CPAPEAAGAPSVFLFPPKPKDTLMISRTPEVTCVVVDVSHEDPEVKFNWYVDGVEVHNA |

TABLE 2-continued

|  |  |
|---|---|
| | KTKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK<br>(SEQ ID NO: 68) |
| VH_27H9_NA_+_<br>AAA | EVQLLESGGGLVQPGGSLRLSCAASGFTFRDYSMSWVRQAPGKGLEWVSAISWNADSTY<br>YAESAKGRFTISRDNSKNTLYLQMNSLRAEDTAVYYCAKSWATPIESLYYYGSDYWGQG<br>TLVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHTCPP<br>CPAPEAAGAPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK<br>(SEQ ID NO: 69) |
| VH_21B3_AAA | ELQLVESGGGLVQPGGSLRLSCAASGFTFRDYSMSWVRQAPGKGLEWVSAISWNGDSTY<br>YAESMKGRFTISRDNAKNTLYLQMNSLKSEDTAVYYCAKSWATPIESLYYYGMDYWKGG<br>TLVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHTCPP<br>CPAPEAAGAPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK<br>(SEQ ID NO: 70) |
| VH_27H6 | ELQLVESGGGLVQPGGSLRLSCAASGFTFSDYSASWVRQAPGKGLEWVSAISWSGDSTY<br>YAESVKGRFTIFRDNSKNTLYLQMNSLRAEDTAVYYCAKSWATPIESLYYYGSDYWGQG<br>TLVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK<br>(SEQ ID NO: 71) |
| VH_27H4 | ELQLVESGGGLVQPGGSLRLSCAASGFTFRDYSMSWVRQAPGKGLEWVSAISWNGDSTY<br>YAESLKGRFTISRDNAKNTLYLQMNSLRAEDTAVYYCAKSWATPIESLYYYGSDYWGQG<br>TLVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK<br>(SEQ ID NO: 72) |
| VH_27H9 | EVQLLESGGGLVQPGGSLRLSCAASGFTFRDYSMSWVRQAPGKGLEWVSAISWNGDSTY<br>YAESAKGRFTISRDNSKNTLYLQMNSLRAEDTAVYYCAKSWATPIESLYYYGSDYWGQG<br>TLVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTIPPVLDSDGSFF<br>LYSKLIVDKSRWQQGNVESCSVMHEALHNHYTQKSLSLSPGK<br>(SEQ ID NO: 73) |
| HC_13B4 | ELQLVESGGGLVQPGGSLRLSCAASGFTFRDYSMSWVRQAPGKGLEWVSAISWNGDSTY<br>YAESMKGRFTISRDNAKNTLYLQMNSLKSEDTAVYYCAKSWATPIESLYYYGMDYWGKG<br>TLVTVSSASTKGPSVFPLAPSSKSTSGGTAALGCLVKSYFPEPVTVSWNSGALTSGVHT<br>FPAVLQSSGLYSLSSVVTVPSSSLGTQTYICNVNHKPSNTKVDKKVEPKSCDKTHTCPP<br>CPAPELLGGPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREP<br>QVYTLPPSRDELTKNQVSLICLVKGFYPSDIAVEWESNGQPENNYKTIPPVLDSDGSFF<br>LYSKLIVDKSRWQQGNVESCSVMNEALHNHYTQKSLSLSPGK<br>(SEQ ID NO: 74) |
| Light Chain | Light Chain Sequence (VL + CL) |
| LC_27H6_DG/EG | SYELTQPLSVSVALRQAAKITCGGNNIGSQTAQWYQQKPGQAPVLVIYANNRRPSGIPE<br>RFSGSKSGNTATLTISRAQAGDEADYYCQVWEGSTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 75) |
| LC_27H6_DG/DA | SYELTQPLSVSVALRQAAKITCGGNNIGSQTAQWYQQKPGQAPVLVIYANNRRPSGIPE<br>RFSGSKSGNTATLTISRAQAGDEADYYCQVWDASTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 76) |

TABLE 2-continued

| | |
|---|---|
| LC_27H9_NG/QG | SYELTQPLSVSVALRQTARITCGGNNIGSQTAQWYQQKPGQAPVLVIYANNRRPSGIPE<br>RFSGSKSGNTATLTISRAQAEDEADYYCQVWDESTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 77) |
| LC_27H9_NG/NA | SYELTQPLSVSVALRQTARITCGGNNIGSQTAQWYQQKPGQAPVLVIYANNRRPSGIPE<br>RFSGSKSGNTATLTISRAQAEDEADYYCQVWDESTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 78) |
| LC_27H4_NG/QG | SYELTQPLSVSVALGQTARITCGGNNIGSQTAQWYQQKPGQAPVLVIYANNRRPSGIPE<br>RFSGSKSGNTATLTISRAQAEDEADYYCQVWEDSTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 79) |
| LC_27H4_NG/NA | SYELTQPLSVSVALGQTARITCGGNNIGSQTAQWYQQKPGQAPVLVIYANNRRPSGIPE<br>RFSGSKSGNTATLTISRAQAEDEADYYCQVWEDSTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 80) |
| LC_27H4_NA_+_<br>AAA | SYELTQPLSVSVALGQTARITCGGNNIGSQTAQWYQQKPGQAPVLVIYANNRRPSGIPE<br>RFSGSKSGNTATLTISRAQAEDEADYYCQVWEDSTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 81) |
| LC_27H9_NA_+_<br>AAA | SYELTQPLSVSVALRQTARITCGGNNIGSQTAQWYQQKPGQAPVLVIYANNRRPSGIPE<br>RFSGSKSGNTATLTISRAQAEDEADYYCQVWDESTQAIVEGGGTKLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 82) |
| LC_21B3_AAA | SYELTQSPSVSVALRQTAKITCGGNNIGSQTAQWYQQKPGQAPVLVIYANNRRPSGIPE<br>RFSGSKSGNTATLTISGAQAEDEADYYCQVWDGSTQAIVEGGGTHLTVLGQPKAAPSVT<br>LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS<br>(SEQ ID NO: 83) |
| LC_27H6 | SYELTQPLSVSVALRQAAKITCGGNNIGSQTAQWYQQKPGQAPVLVIYANNRRPSGIPE<br>RFSGSKSGNTATLTISRAQAGDEADYYCQVWDGSTQAIVEGGGTKLTVLGQPKAAPSVT<br>LEPPSSEELQANKATLVCLISDFYPGAVIVAWKADSSPVKAGVETTIPSKQSNNKYAAS<br>SYLSLTPEQWKSHRSYSCQVTHEGSTVEKTVAPTECS<br>(SEQ ID NO: 84) |
| LC_27H4 | SYELTQPLSVSVALGQTARITCGGNNIGSQTAQWYQQKPGQAPVLVIYANNRRPSGIPE<br>RFSGSKSGNTATLTISRAQAEDEADYYCQVWEDSTQAIVEGGGTKLTVLGQPKAAPSVT<br>LEPPSSEELQANKATLVCLISDFYPGAVIVAWKADSSPVKAGVETTIPSKQSNNKYAAS<br>SYLSLTPEQWKSHRSYSCQVTHEGSTVEKTVAPTECS<br>(SEQ ID NO: 85) |
| LC_27H9 | SYELTQPLSVSVALRQTARITCGGNNIGSQTAQWYQQKPGQAPVLVIYANNRRPSGIPE<br>RFSGSKSGNTATLTISRAQAEDEADYYCQVWDESTQAIVEGGGTKLTVLGQPKAAPSVT<br>LEPPSSEELQANKATLVCLISDFYPGAVIVAWKADSSPVKAGVETTIPSKQSNNKYAAS<br>SYLSLTPEQWKSHRSYSCQVTHEGSTVEKTVAPTECS<br>(SEQ ID NO: 86) |
| Constant Region | CH1-CH2-CH3 |
| 27H6_DG/EG | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H6_DG/DA | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H9_NG/QG | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE |

TABLE 2-continued

| | |
|---|---|
| | QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H9_NG/NA | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H4_NG/QG | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H4_NG/NA | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H4_NA_+_AAA | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEAA<br>GAPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 88) |
| 27H9_NA_+_AAA | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEAA<br>GAPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 88) |
| 21B3_AAA | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEAA<br>GAPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 88) |
| 27H6 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H4 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 27H9 | ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 87) |
| 13B4 | ASTKGPSVFPLAPSSKSTSGGTAALGCLVKSYFPEPVTVSWNSGALTSGVHTFPAVLQS<br>SGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLIVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMNEALHNHYTQKSLSLSPGK (SEQ ID NO: 89) |

In some embodiments, the anti-Flt-1 antibody, or antigen-binding fragment thereof, comprises one or more complementarity determining regions (CDR) selected from the group consisting of a VL CDR1 defined by an amino acid sequence having at least 60%, 70%, 80%, 90%, 95% or 98% identity to any one of SEQ ID NO: 19 to SEQ ID NO:21, a VL CDR2 defined by an amino acid sequence having at least 60%, 70%, 80%, 90%, 95% or 98% identity to any one of SEQ ID NO:22 to SEQ ID NO:24, a VL CDR3 defined by an amino acid sequence having at least 60%, 70%, 80%, 90%, 95% or 98% identity to any one of SEQ ID NO:25 to SEQ ID NO:34, a VH chain CDR1 defined by an amino acid sequence having at least 60%, 70%, 80%, 90%, 95% or 98% identity to any one of SEQ ID NO: 1 to SEQ ID NO:4, a VH CDR2 defined by an amino acid sequence having at least 60%, 70%, 80%, 90%, 95% or 98% identity to any one of SEQ ID NO:5 to SEQ ID NO: 14, and a VH CDR3 defined by an amino acid sequence having at least 60%, 70%, 80%, 90%, 95% or 98% identity to any one of SEQ ID NO:15 to SEQ ID NO:18. In some embodiments, the VL CDR3 is not SEQ ID NO:25. In some embodiments, the VH CDR3 is not SEQ ID NO:15.

In some embodiments, the one or more CDRs comprise the VL CDR3 defined by the amino acid sequence having at least 60%, 70%, 80%, 90%, 95% or 98% identity to any one of SEQ ID NO:25 to SEQ ID NO:34; and the VH CDR3 defined by the amino acid sequence having at least 60%, 70%, 80%, 90%, 95% or 98% identity to any one of SEQ ID NO: 15 to SEQ ID NO:18. In some embodiments, the VL CDR3 is not SEQ ID NO:25. In some embodiments, the VH CDR3 is not SEQ ID NO:15.

In some embodiments, the one or more CDRs comprise the VL CDR1 defined by the amino acid sequence having at least 60%, 70%, 80%, 90%, 95% or 98% identity to any one of SEQ ID NO: 19 to SEQ ID NO:21, the VL CDR2 defined by the amino acid sequence having at least 60%, 70%, 80%, 90%, 95% or 98% identity to any one of SEQ ID NO:22 to SEQ ID NO:24, and the VL CDR3 defined by amino acid sequence having at least 60%, 70%, 80%, 90%, 95% or 98% identity to any one of SEQ ID NO:25 to SEQ ID NO:34. In some embodiments, the VL CDR3 is not SEQ ID NO:25.

In some embodiments, the one or more CDRs comprise the VH CDR1 defined by the amino acid sequence having at least 60%, 70%, 80%, 90%, 95% or 98% identity to any one of SEQ ID NO: 1 to SEQ ID NO:4, the VH CDR2 defined by the amino acid sequence having at least 60%, 70%, 80%, 90%, 95% or 98% identity to any one of SEQ ID NO:5 to SEQ ID NO: 14, and the VH CDR3 defined by the amino acid sequence having at least 60%, 70%, 80%, 90%, 95% or 98% identity to any one of SEQ ID NO:15 to SEQ ID NO: 18. In some embodiments, the VH CDR3 is not SEQ ID NO:15.

In some embodiments, the anti-Flt-1 antibody, or antigen-binding fragment thereof, comprises a VL chain comprising the VL CDR1, VL CDR2, and VL CDR3 defined by the amino acid sequence of SEQ ID NO: 19, SEQ ID NO:22, and SEQ ID NO:25, respectively. In another embodiment, the anti-Flt-1 antibody, or antigen-binding fragment thereof, comprises a VL chain comprising the VL CDR1, VL CDR2, and VL CDR3 defined by the amino acid sequence of SEQ ID NO:20, SEQ ID NO:23, and SEQ ID NO:25, respectively. In yet another embodiment the anti-Flt-1 antibody, or antigen-binding fragment thereof, comprises a VL chain comprising the VL CDR1 and VL CDR2 defined by the amino acid sequence of SEQ ID NO:21, SEQ ID NO:24, respectively, and the VL CDR3 defined by the amino acid sequence of SEQ ID NO:26, SEQ ID NO:27, SEQ ID NO:28, SEQ ID NO:29, SEQ ID NO:30, SEQ ID NO:31, SEQ ID NO:32, SEQ ID NO:33 or SEQ ID NO:34. In a particular embodiment, the anti-Flt-1 antibody, or antigen-binding fragment thereof, comprises a VL chain comprising the VL CDR1 defined by the amino acid sequence of SEQ ID NO:21, the VL CDR2 defined by the amino acid sequence of SEQ ID NO:24, and the VL CDR3 defined by the amino acid sequence of SEQ ID NO:32. In some embodiments, the VL CDR3 is not SEQ ID NO:25.

In another embodiment, the anti-Flt-1 antibody, or antigen-binding fragment thereof, comprises a VH chain comprising the VH CDR1, VH CDR2, and VH CDR3 defined by the amino acid sequences of SEQ ID NO: 1, SEQ ID NO:5, and SEQ ID NO: 15, respectively. In another embodiment, the anti-Flt-1 antibody, or antigen-binding fragment thereof, comprises a VH chain comprising a VH CDR1, VH CDR2, and VH CDR3 defined by the amino acid sequences of SEQ ID NO:2, SEQ ID NO:6, and SEQ ID NO: 16, respectively. In another embodiment, the anti-Flt-1 antibody or antigen-binding fragment thereof, comprises a VH chain comprising a VH CDR1, VH CDR2, and VH CDR3 defined by the amino acid sequences of SEQ ID NO:2, SEQ ID NO:10, and SEQ ID NO:18, respectively. In another embodiment, the anti-Flt-1 antibody, or antigen-binding fragment thereof, comprises a VH chain comprising the VH CDR1 and the VH CDR3 defined by the amino acid sequences of SEQ ID NO:2 and SEQ ID NO: 17, respectively, and the VH CDR2 defined by the amino acid sequence of SEQ ID NO:7, SEQ ID NO:8, SEQ ID NO:13 or SEQ ID NO:14. In another embodiment, the anti-Flt-1 antibody, or antigen-binding fragment thereof, comprises a VH chain comprising the VH CDR1 and the VH CDR3 defined by the amino acid sequences of SEQ ID NO:3 and SEQ ID NO: 17, respectively, and a VH CDR2 defined by the amino acid sequence of SEQ ID NO:9, SEQ ID NO: 11 or SEQ ID NO: 12. In another embodiment, the anti-Flt-1 antibody, or antigen-binding fragment thereof, comprises a VH chain comprising the VH CDR1, VH CDR2, and VH CDR3 defined by the amino acid sequences of SEQ ID NO:4, SEQ ID NO:9, and SEQ ID NO: 17, respectively. In a particular embodiment, the anti-Flt-1 antibody, or antigen-binding fragment thereof, comprises a VH chain comprising the VH CDR1 defined by the amino acid sequence of SEQ ID NO:3, the VH CDR2 defined by the amino acid sequence of SEQ ID NO: 12 and the VH CDR3 defined by the amino acid sequence of SEQ ID NO: 17. In some embodiments, the VH CDR3 is not SEQ ID NO:15.

In another embodiment, the anti-Flt-1 antibody, or antigen-binding fragment thereof, comprises a light chain VL region comprising an amino acid sequence having at least 60%, 70%, 80%, 90%, 95% or 98% identity to any one of SEQ ID NO:49 to SEQ ID NO:61, and/or a heavy chain VH region comprising an amino acid sequence having at least 60%, 70%, 80%, 90%, 95% or 98% identity to any one of SEQ ID NO:35 to SEQ ID NO:48. In a particular embodiment, the VL region comprises the amino acid sequence of SEQ ID NO:60 and the VH region comprises the amino acid sequence of SEQ ID NO:45. In another embodiment, the antibody further comprises a heavy chain constant region comprising an amino acid sequence having at least 60%, 70%, 80%, 90%, 95% or 98% identity to any one of SEQ ID NO:87 to SEQ ID NO:89. In some embodiments, the VL region is not SEQ ID NO:49 or SEQ ID NO:50. In some embodiment, the VH region is not SEQ ID NO:35 or SEQ ID NO:36.

In another embodiment, the anti-Flt-1 antibody, or antigen-binding fragment thereof, comprises a light chain comprising an amino acid sequence having at least 60%, 70%, 80%, 90%, 95% or 98% identity to any one of SEQ ID NO:75 to SEQ ID NO:86, and/or a heavy chain comprising an amino acid sequence having at least 60%, 70%, 80%, 90%, 95% or 98% identity to any one of SEQ ID NO:62 to SEQ ID NO:74. In a particular embodiment, the light chain comprises the amino acid sequence of SEQ ID NO:76 and the heavy chain region comprises the amino acid sequence of SEQ ID NO:71.

In some embodiments, the heavy chain of the anti-Flt-1 antibody, or antigen-binding fragment thereof, comprises the amino acid sequence (SEQ ID NO: 108)
MGWSCIILFLVATATGVHSELQLVESGGGLVQPGGSLRLSCAASGETFS

DYSASWVRQAPGKGLEWVSAISWSGDSTYYAESVKGRFTIFRDNSKNTL

YLQMNSLRAEDTAVYYCAKSWATPIESLYYYGSDYWGQGTLVTVSSAST

KGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPK

SCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGKX.

In some embodiments, the heavy chain of the anti-Flt-1 antibody, or antigen-binding fragment thereof, comprises the amino acid sequence (SEQ ID NO: 109)
ELQLVESGGGLVQPGGSLRLSCAASGFTFSDYSASWVRQAPGKGLEWVS

AISWSGDSTYYAESVKGRFTIFRDNSKNTLYLQMNSLRAEDTAVYYCAK

SWATPIESLYYYGSDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPGK.

In some embodiments, the light chain of the anti-Flt-1 antibody, or antigen-binding fragment thereof, comprises the amino acid sequence (SEQ ID NO: 110)
MGWSCIILFLVATATGVHSSYELTQPLSVSVALRQAAKITCGGNNIGSQ

TAQWYQQKPGQAPVLVIYANNRRPSGIPERFSGSKSGNTATLTISRAQA

GDEADYYCQVWDASTQAIVFGGGTKLTVLGQPKAAPSVTLFPPSSEELQ

ANKATLVCLISDFYPGAVTVAWKADSSPVKAGVETTTPSKQSNNKYAAS

SYLSLTPEQWKSHRSYSCQVTHEGSTVEKTVAPTECSX.

In some embodiments, the anti-Flt-1 antibody, or antigen-binding fragment thereof, comprises a heavy chain of SEQ ID NO: 108 or SEQ ID NO: 109 and a light chain of SEQ ID NO: 110 or SEQ ID NO:76.

In some embodiments, an anti-Flt-1 antibody, or antigen-binding fragment thereof, binds human Flt-1 with an affinity greater than about $10^{-7}$ M, greater than about $0.5 \times 10^{-7}$, greater than about $10^{-8}$, greater than about $0.5 \times 10^{-8}$, greater than about $10^{-9}$ M, greater than about $0.5 \times 10^{-9}$, greater than about $10^{-10}$ M, greater than about $0.5 \times 10^{-10}$ M, greater than about $10^{-11}$ M, greater than about $0.5 \times 10^{-11}$ M, greater than about $10^{-12}$ M, or greater than about $0.5 \times 10^{-12}$ M. In other embodiments, an anti-Flt-1 antibody, or antigen-binding fragment thereof, binds to mouse Flt-1 with an affinity greater than about $10^{-7}$ M, greater than about $0.5 \times 10^{-7}$, greater than about $10^{-8}$, greater than about $0.5 \times 10^{-8}$, greater than about $10^{-9}$ M, greater than about $0.5 \times 10^{-9}$, greater than about $10^{-10}$ M, greater than about $0.5 \times 10^{-10}$ M, greater than about $10^{-11}$ M, greater than about $0.5 \times 10^{-11}$ M, greater than about $10^{-12}$ M, or greater than about $0.5 \times 10^{-12}$ M. The affinity of an Flt-1 antibody may be measured, for example, in a surface plasmon resonance assay, such as a BIACORE assay.

In some embodiments, an anti-Flt-1 antibody, or antigen-binding fragment thereof, is characterized by an $IC_{50}$ below about 500 pM, below about 400 pM, below about 300 pM, below about 200 pM, below about 100 pM, below about 50 pM, below about 25 pM, below about 10 pM, below about 5 pM or below about 1 pM in a competition assay with human Flt-1. In some embodiments, an anti-Flt-1 antibody, or antigen-binding fragment thereof, is characterized by an $IC_{50}$ below about 500 pM, below about 400 pM, below about 300 pM, below about 200 pM, below about 100 pM, below about 50 pM, below about 25 pM, below about 10 pM, below about 5 pM or below about 1 pM in a competition assay with mouse Flt-1.

In some embodiments, an anti-Flt-1 antibody, or antigen-binding fragment thereof inhibits the binding and/or activity of VEGF at the Flt-1 receptor. In some embodiments, an anti-Flt-1 antibody, or antigen-binding fragment thereof, is characterized by an $IC_{50}$ below about 500 pM, below about 400 pM, below about 300 pM, below about 200 pM, below about 100 pM, below about 50 pM, below about 25 pM, below about 10 pM, below about 5 pM or below about 1 pM for inhibition of binding of VEGF to human Flt-1 in a competition assay.

In some embodiments, an anti-Flt-1 antibody, or antigen-binding fragment thereof completes with, and or inhibits VEGF binding to soluble Flt-1. In other embodiments, the competition, and or inhibition, is in a dose dependent manner. In particular embodiments, the inhibition of binding of VEGF to Flt-1 results in increased phosphorylation of VEGF R2. Without intending to be bound by theory, binding of the anti-Flt-1 antibody, or antigen-binding fragment thereof to Flt-1 inhibits the binding of VEGF to Flt-1. Unbound VEGF binds VEGF R2 which may be demonstrated by measuring phosphorylation of VEGF R2. In particular embodiments, the anti-Flt-1 antibody, or antigen-binding fragment rescues VEGF R2 phosphorylation in a dose dependent manner. For example, VEGF R2 phosphorylation may be rescued by at least about 100%, about 95%, about 90%, about 85%, about 80%, about 75%, about 70%, about 65%, about 60%, about 55%, about 50%, about 45%, about 40%, about 35% about 30%, about 25%, about 20%, about 15%, about 10% or about 5%.

In some embodiments, an anti-Flt-1 antibody, or antigen-binding fragment thereof provide greater than about 95%, greater than about 90%, greater than about 85%, greater than about 80%, greater than about 75%, greater than about 70%, greater than about 65%, greater than about 60%, greater than about 55%, greater than about 50%, greater than about 45%, greater than about 40%, greater than about 35%, greater than about 30%, greater than about 25%, greater than about 20%, greater than about 15%, or greater than about 10% rescue in a bioassay. In a particular embodiment the bioassay comprises human primary vein endothelial cells (HUVECs) stimulated with VEGF in the presence of sFlt-1 and an anti-Flt-1 antibody or antigen-binding fragment thereof. VEGF induced activation of cells may be assayed by determining the phosphorylation status of the VEGF R2 receptor. Data may be expressed as a percent rescue of the phosphorylation of the VEGF R2 receptor relative to the phosphorylation of the VEGF R2 receptor in the presence of sFlt-1 alone (e.g., without anti-Flt-1 antibodies).

In some embodiments, an anti-Flt-1 antibody, or antigen-binding fragment thereof, has a half-life of greater than about 200 hours, greater than about 150 hours, greater than about 100 hours, greater than about 95 hours, greater than about 90 hours, greater than about 85 hours, greater than about 80 hours, greater than about 75 hours, greater than about 70 hours, greater than about 65 hours, greater than about 60 hours, greater than about 55 hours, greater than about 50 hours or greater than about 45 hours, and ranges therein. In some embodiments, the half-life is measured in a mouse.

In some embodiments, an anti-Flt-1 antibody, or antigen-binding fragment thereof, has a maximum serum concentration of greater than about 400 ug/mL, greater than 375 ug/mL, greater than about 350 ug/mL, greater than about 325 ug/mL, greater than about 300 ug/mL, greater than about 275 ug/mL, greater than about 250 ug/mL, greater than about 225 ug/mL, greater than about 200 ug/mL, greater than about 175 ug/mL, greater than about 150 ug/mL, greater than about 125 ug/mL, greater than about 100 ug/mL, greater than about 75 ug/mL or greater than about 50 ug/mL, and ranges therein. In some embodiments, the maximum serum concentration is measured in a mouse.

In some embodiments, an anti-Flt-1 antibody, or antigen-binding fragment thereof selectively binds Flt-1 and has minimal or no appreciable binding to other VEGF receptors. In some embodiments, an anti-Flt-1 antibody, or antigen-binding fragment thereof selectively binds Flt-1 and has minimal or no appreciable binding to VEGF R2 (Flk-1) and/or VEGF R3 (Flt-4).

In some embodiments, an anti-Flt-1 antibody, or antigen-binding fragment thereof has a ka of greater than about $1 \times 10^{-3}$ $M^{-1}$ $sec^{-1}$, greater than about $1 \times 10^{-4}$ $M^{-1}$ $sec^{-1}$, greater than about $1 \times 10^{-5}$ $M^{-1}$ $sec^{-1}$, greater than about $1 \times 10^{-6}$ $M^{-1}$ $sec^{-1}$, or greater than about $1 \times 10^{-7}$ $M^{-1}$ $sec^{-1}$ when binding to human Flt-1.

In some embodiments, an anti-Flt-1 antibody, or antigen-binding fragment thereof has a kd of greater than about $1 \times 10^{-3}$ $sec^{-1}$, greater than about $1 \times 10^{-4}$ $sec^{-1}$, greater than about $1 \times 10^{-5}$ $sec^{-1}$ or greater than about $1 \times 10^{-6}$ sec-1 when binding to human Flt-1.

In some embodiments, an anti-Flt-1 antibody, or antigen-binding fragment thereof has a $K_D$ of greater than about $1 \times 10^{-8}$ M, greater than about $1 \times 10^{-9}$ M, greater than about $1 \times 10^{-10}$ M, greater than about $1 \times 10^{-11}$ M or greater than about $1 \times 10^{-12}$ M when binding to human Flt-1.

In some embodiments an anti-Flt-1 antibody, or antigen-binding fragment thereof binds to soluble Flt-1. In particular embodiments, the binding is dose-dependent wherein higher concentrations of antibody, or antigen-binding fragment thereof, bind greater amounts of soluble Flt-1.

In some embodiments, an anti-Flt-1 antibody, or antigen-binding fragment thereof has a percent human identify of greater than about 99%, greater than about 98%, greater than about 97%, greater than about 96%, greater than about 95%, greater than about 94%, greater than about 93%, greater than about 92%, greater than about 91%, greater than about 90% or greater than about 80%.

In some embodiments, an anti-Flt-1 antibody, or antigen-binding fragment thereof has a percent human homology of greater than about 99%, greater than about 98%, greater than about 97%, greater than about 96%, greater than about 95%, greater than about 94%, greater than about 93%, greater than about 92%, greater than about 91%, greater than about 90% or greater than about 80%.

In some embodiments, an anti-Flt-1 antibody, or antigen-binding fragment thereof binds to Flt-1 protein. In some embodiment the Flt-1 protein is a recombinant protein, for example recombinant sFlt-1. In a particular embodiment, the anti-Flt-1 antibody, or antigen-binding fragment thereof binds human Flt-1 isoform 1 (NP_002010.2 GI:156104876; SEQ ID NO:90) (Table 13). In another embodiment the anti-Flt-1 antibody, or antigen-binding fragment thereof binds to human Flt-1 isoform X1 (XP_011533316.1 GI:767977511; SEQ ID NO:91). In another embodiment the anti-Flt-1 antibody, or antigen-binding fragment thereof binds to human Flt-1 isoform 2 precursor (NP_001153392.1 GI:229892220; SEQ ID NO:92). In yet another embodiment the anti-Flt-1 antibody, or antigen-binding fragment thereof binds to human Flt-1 isoform 3 precursor (NP_001153502.1 GI:229892300; SEQ ID NO:93). In another embodiment the anti-Flt-1 antibody, or antigen-binding fragment thereof binds to human Flt-1 isoform 4 precursor (NP_001153503.1 GI:229892302; SEQ ID NO:94).

In some embodiments the anti-Flt-1 antibody, or antigen-binding fragment thereof binds to a particular a epitope of the Flt-1 protein. For example, the anti-Flt-1 antibody or antigen-binding portion thereof binds to amino acids sequences as provided in Table 3.

TABLE 3

| amino acid position based on SEQ ID NO: 90 | Amino acid sequence | SEQ ID NO |
|---|---|---|
| 141-153 | EIPEIIHMTEGRE | SEQ ID NO: 95 |
| 193-206 | IISNATYKEIGLLT | SEQ ID NO: 96 |
| 130-138 | DTGRPFVEM | SEQ ID NO: 97 |
| 141-148 | EIPEIIHM | SEQ ID NO: 98 |
| 139-148 | YSEIPEIIHM | SEQ ID NO: 99 |
| 139-153 | YSEIPEIIHMTEGRE | SEQ ID NO: 100 |
| 178-206 | IPDGKRIIWDSRKGF IISNATYKEIGLLT | SEQ ID NO: 101 |
| 199-204 | YKEIGL | SEQ ID NO: 102 |
| 128-138 | ISDTGRPFVEM | SEQ ID NO: 103 |

In some embodiments, administration of an anti-Flt-1 antibody, or antigen-binding fragment thereof in vivo results in peak serum antibody levels of at least about 700 ug/mL, at least about 650 ug/mL, at least about 600 ug/mL, at least about 550 ug/mL, at least about 500 ug/mL, at least about 450 ug/mL, at least about 400 ug/mL, at least about 350 ug/mL, at least about 300 ug/mL, at least about 250 ug/mL, at least about 200 ug/mL, at least about 150 ug/mL, at least about 100 ug/mL, at least about 50 ug/mL, at least about 40 ug/mL, at least about 30 ug/mL, at least about 20 ug/mL, at least about 10 ug/mL or at least about 5 ug/mL, and ranges therein. In some embodiments, the peak serum antibody level is dose dependent.

In some embodiments, administration of an anti-Flt-1 antibody, or antigen-binding fragment thereof in vivo results in trough serum antibody levels of at least about 450 ug/mL, at least about 400 ug/mL, at least about 350 ug/mL, at least about 300 ug/mL, at least about 250 ug/mL, at least about 200 ug/mL, at least about 150 ug/mL, at least about 100 ug/mL, at least about 50 ug/mL or at least about 25 ug/mL, and ranges therein. In some embodiments, the trough serum antibody level is dose dependent.

In some embodiments, administration of an anti-Flt-1 antibody, or antigen-binding fragment thereof in vivo results in a decreased serum level of soluble Flt-1 as compared to a baseline level or as compared to a level in subjects administered vehicle alone. Typically, the baseline level is measured immediately before administration. In some embodiments, administration of the anti-Flt-1 antibody or antigen-binding fragment thereof results in a decreased serum level of soluble Flt-1 by at least about 95%, about 90%, about 80%, about 70%, about 60%, about 50%, about 40%, about 30%, about 20% or about 10% as compared to the baseline serum level of soluble Flt-1 immediately before administration. In some embodiments, administration of the anti-Flt-1 antibody, or antigen-binding fragment thereof results in a decreased serum level of soluble Flt-1 to less than about 4000 pg/mL, about 3500 pg/mL, about 3000 pg/mL, about 2500 pg/mL, about 2000 pg/mL, about 1750 pg/mL, about 1500 pg/mL, about 1250 pg/mL, about 1000 pg/mL, about 900 pg/mL, about 800 pg/mL, about 700 pg/mL, about 600 pg/mL, about 500 pg/mL, about 450 pg/mL, about 400 pg/mL, about 350 pg/mL, about 300 pg/mL, about 250 pg/mL, about 200 pg/mL, about 150 pg/mL, about, 100 pg/mL, about 50 pg/mL or about 10 pg/mL, and ranges therein. In some embodiments, administration of the anti-Flt-1 antibody, or antigen-binding fragment thereof results in a decreased serum level of soluble Flt-1 as compared to the serum level of soluble Flt-1 in a subject who is not administered the antibody or antigen-binding fragment thereof. In some embodiments, the decreased serum level of soluble Flt-1 is dose dependent.

In some embodiments, administration of an anti-Flt-1 antibody, or antigen-binding fragment thereof in vivo results in an increased serum level of VEGF as compared to a baseline level or as compared to a level in subjects treated with vehicle alone. Typically, the baseline level is measured immediately before treatment. In some embodiments, administration of the anti-Flt-1 antibody or antigen-binding fragment thereof results in an increased serum level of VEGF by at least about 95%, about 90%, about 80%, about 70%, about 60%, about 50%, about 40%, about 30%, about 20% or about 10% as compared to the baseline serum level of VEGF immediately before administration. In some embodiments, administration of the anti-Flt-1 antibody, or antigen-binding fragment thereof results in an increased serum level of VEGF to more than about 500 pg/mL, about 450 pg/mL, about 400 pg/mL, about 350 pg/mL, about 300 pg/mL, about 250 pg/mL, about 200 pg/mL, about 150 pg/mL, about 100 pg/mL about 50 pg/mL or about 25 pg/mL and ranges therein. In some embodiments, administration of the anti-Flt-1 antibody, or antigen-binding fragment thereof results in an increased serum level of VEGF as compared to the serum level of VEGF in a subject who is not treated. In some embodiments, the increased serum level of VEGF is dose dependent.

In some embodiments, administration of an anti-Flt-1 antibody, or antigen-binding fragment thereof in vivo results in increased angiogenesis in muscle tissue. In some embodiments the muscle is skeletal muscle. In particular embodiments, the muscle is the diaphragm muscle, the gastrocnemius muscle and/or the tibialis anterior (TA) muscle. In some embodiments, the increased angiogenesis is demonstrated by increased CD31 staining of an endothelial cell marker, for example, CD31. In some embodiments, the increased staining may be measured, for example, by measuring the percent CD31 positive area in muscle of mice administered the anti-Flt-1 antibody, or antigen-binding fragment thereof. For example, the percent CD31 positive area in the diaphragm muscle of mice administered the anti-Flt-1 antibody, or antigen-binding fragment thereof may be at least about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4% or about 2.5% of the total tissue area. In a further example, the percent CD31 positive area in the TA muscle of mice administered the anti-Flt-1 antibody, or antigen-binding fragment thereof may be at least about 0.5%, about 0.6%, about 0.7%, about 0.8%, about 0.9% or about 1.0% pf the total tissue area. In a particular embodiment, the percent CD31 positive area in the diaphragm muscle or TA muscle of mice administered the anti-Flt-1 antibody may be significantly higher than the percent CD31 positive area in the diaphragm muscle or TA muscle of mice administered an isotype control antibody.

In some embodiments, the increased staining of an endothelial cell marker may be measured, for example, by measuring the normalized CD31 percent positivity in the muscle of mice administered the anti-Flt-1 antibody, or antigen-binding fragment thereof. In particular embodiments the increased CD31 staining the muscle of mice administered the anti-Flt-1 antibody, or antigen-binding fragment thereof, is relative to CD31 staining measured in the muscle of mice administered an isotype control antibody. For example, the normalized CD31 percent positivity in the diaphragm muscle of mice administered the anti-Flt-1 antibody, or antigen-binding fragment thereof may be at least about 200%, about 190%, about 180%, about 170%, about 160%, about 150%, about 140%, about 130%, about 120% or about 110%. In a further example, the normalized CD31 percent positivity in the TA muscle of mice administered the anti-Flt-1 antibody, or antigen-binding fragment thereof may be at least about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120% or about 110%, and ranges therein.

In some embodiments, an anti-Flt-1 antibody, or antigen-binding fragment thereof selectively binds human Flt-1, and has minimal or no appreciable binding to other mammalian Flt-1 receptors (e.g., with a binding affinity less than 10 M or $10^{-6}$ M). In some embodiments, an anti-Flt-1 antibody, or antigen-binding fragment thereof selectively binds human Flt-1 and does not bind to monkey Flt-1. In some embodiments, an anti-Flt-1 antibody, or antigen-binding fragment thereof selectively binds human Flt-1 and does not bind to mouse Flt-1.

In some embodiments, an anti-Flt-1 antibody, or antigen-binding fragment thereof binds human Flt-1 as well as monkey Flt-1. In some embodiments, an anti-Flt-1 antibody, or antigen-binding fragment thereof binds to cynomolgus Flt-1. In some embodiments an anti-Flt-1 antibody, or antigen-binding fragment thereof binds human Flt-1 as well as mouse Flt-1.

In some embodiments, an anti-Flt-1 antibody, or antigen-binding fragment thereof, is selected from the group consisting of IgG, F(ab')$_2$, F(ab)$_2$, Fab', Fab, ScFvs, diabodies, triabodies and tetrabodies.

In some embodiments an anti-Flt-1 antibody, or antigen-binding fragment thereof, is IgG. In some embodiments an anti-Flt-1 antibody, or antigen-binding fragment thereof, is IgG1.

Engineered Constant Regions

In some embodiments, a suitable anti-Flt-1 antibody contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. Particularly suitable Fc domains include those derived from human or humanized antibodies.

It is contemplated that improved binding between Fc domain and the FcRn receptor results in prolonged serum half-life. Thus, in some embodiments, a suitable Fc domain (SEQ ID NO: 104) comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Leu 234, Leu 235, Gly 237, Thr 250, Met 252, Ser 254, Thr 256, Thr 307, Glu 380, Met 428, His 433, and/or Asn 434 of human IgG1.

Some mutations in the Fc domain lead to reduced binding of the IgG with the FcRn receptor and thereby inhibit effector function. In some embodiments, a suitable Fc domain (SEQ ID NO: 104) comprises one or more mutations at one or more positions corresponding to Leu 234, Leu 235 and Gly 237 of human IgG1. In a particular embodiment Leu 234 is mutated to Ala. In another embodiment Leu 235 is mutated to Ala. In yet another embodiment, Gly 237 is mutated to Ala.

In some embodiments, an anti-FLT-1 antibody or antigen-binding fragment contains a spacer and/or is linked to another entity. In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAP (SEQ ID NO: 105) (GAG linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGGGAP (SEQ ID NO: 106) (GAG2 linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGG GAPGGGGGAAAAAGGGGG GAP (SEQ ID NO:107) (GAG3 linker).

Production of Anti-Flt-1 Antibodies and Antigen-Binding Fragments

A recombinant anti-Flt-1 antibody or antigen-binding fragment thereof, suitable for the present invention may be produced by any available means. For example, a recombinant anti-Flt-1 antibody or antigen-binding fragment may be recombinantly produced by utilizing a host cell system engineered to express a recombinant anti-Flt-1 antibody or antigen-binding fragment-encoding nucleic acid.

Thus, the present invention further provides polynucleotide sequences encoding the various amino acid sequences described herein. In some embodiments, the present invention provides a polynucleotide sequence encoding an anti-Flt-1 antibody heavy chain or light chain amino acid sequence described herein, for example, any one of SEQ ID NOs:62-86 or SEQ ID NOs:108-110. In some embodiments, the present invention provides a polynucleotide sequence encoding a variable region of an anti-Flt-1 antibody heavy chain or light chain amino acid sequence described herein, for example, any one of SEQ NOs:35-61. In some embodiments, the present invention provides a polynucleotide sequence encoding a CDR region of an anti-Flt-1 antibody heavy chain or light chain amino acid sequence described herein, for example, any one of SEQ ID NOs: 1-34. In some embodiments, the present invention provides a polynucleotide sequence encoding an anti-Flt-1 antibody constant region amino acid sequence described herein, for example, any one of SEQ ID NO:87-89. In some embodiments, the present invention provides a polynucleotide sequence encoding an anti-Flt-1 antibody Fc region amino acid sequence described herein, for example, SEQ ID NO:104. In some embodiments, the present invention provides a polynucleotide sequence encoding an anti-Flt-1 antibody linker amino acid sequence described herein, for example, SEQ ID NOs: 105-107.

In some embodiments, a polynucleotide sequence encoding an anti-Flt-1 antibody heavy chain, light chain, variable region, CDR region, Fc region or linker region amino acid sequence further includes a sequence encoding a signal peptide. As a non-limiting example, a suitable signal peptide includes amino acid sequence MGWSCIILFLVATATGVHS (SEQ ID NO:111).

Various polynucleotide sequences described herein may be embodied in various vector systems for expression of recombinant anti-Flt-1 antibodies or antigen-binding fragment thereof.

Where antibodies are recombinantly produced, any expression system can be used. To give but a few examples, known expression systems include, for example, egg, baculovirus, plant, yeast, or mammalian cells.

In some embodiments, a recombinant anti-Flt-1 antibody or antigen-binding fragment thereof suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); and monkey kidney CV1 line transformed by SV40 (COS-7, ATCC CRL 1651).

In some embodiments, the present invention provides a recombinant anti-Flt-1 antibody or antigen-binding fragment thereof produced from human cells. In some embodiments, the present invention provides an anti-Flt-1 antibody or antigen-binding fragment thereof produced from CHO cells.

Pharmaceutical Compositions Containing the Antibodies of the Invention

The present invention further provides pharmaceutical compositions comprising therapeutically active ingredients in accordance with the invention (e.g. anti-Flt-1 antibody, or antigen-binding fragment thereof), together with one or more pharmaceutically acceptable carrier or excipient. Such pharmaceutical compositions may optionally comprise one or more additional therapeutically-active substances.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient or carrier and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or carrier, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient or carrier, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium or carrier is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient or carrier is at least 95%, at least 96%, at least 97%, at least 98%, at least 99%, or 100% pure. In some embodiments, an excipient or carrier is approved for use in humans and for veterinary use. In some embodiments, an excipient or carrier is approved by United States Food and Drug Administration. In some embodiments, an excipient or carrier is pharmaceutical grade. In some embodiments, an excipient or carrier meets the standards of the United States Pharmacopoeia (USP), the European Pharmacopoeia (EP), the British Pharmacopoeia, and/or the International Pharmacopoeia.

Pharmaceutically acceptable excipients or carriers used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients or carriers may optionally be included in pharmaceutical formulations. Excipients or carriers such as cocoa butter and suppository waxes, coloring agents, coating agents, sweetening, flavoring, and/or perfuming agents can be present in the composition, according to the judgment of the formulator.

Suitable pharmaceutically acceptable excipients or carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

General considerations in the formulation and/or manufacture of pharmaceutical agents may be found, for example, in *Remington: The Science and Practice of Pharmacy* 21st ed., Lippincott Williams & Wilkins, 2005 (incorporated herein by reference).

Routes of Administration

An anti-Flt-1 antibody or antigen-binding fragment thereof described herein (or a composition or medicament containing an anti-Flt-1 antibody or antigen-binding fragment thereof described herein) is administered by any appropriate route. In some embodiments, an anti-Flt-1 antibody or antigen-binding fragment protein or a pharmaceutical composition containing the same is administered parenterally. Parenteral administration may be intravenous, intradermal, intrathecal, inhalation, transdermal (topical), intraocular, intramuscular, subcutaneous, intramuscular, and/or transmucosal administration. In some embodiments, an anti-Flt-1 antibody or antigen-binding fragment thereof or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, an anti-Flt-1 antibody or antigen-binding fragment thereof or a pharmaceutical composition containing the same is administered intravenously. In some embodiments, an anti-Flt-1 antibody or antigen-binding fragment thereof or a pharmaceutical composition containing the same is administered orally. More than one route can be used concurrently, if desired.

In some embodiments, administration results only in a localized effect in an individual, while in other embodiments, administration results in effects throughout multiple portions of an individual, for example, systemic effects. Typically, administration results in delivery of an anti-Flt-1 antibody or antigen-binding fragment to one or more target tissues including but not limited to kidney, liver, brain, spinal cord, intestinal tract, eye, lung, spleen, heart, including cardiac muscle, striated muscle, and smooth muscle.

In some embodiments, striated muscle is selected from the group consisting of triceps, tibialis anterior, soleus, gastrocnemius, quadriceps, and diaphragm.

In some embodiments, the smooth muscle is the muscles lining blood vessels, bronchioles, bladder, and gastrointestinal tract such as rectum.

Dosage Forms and Dosing Regimen

In some embodiments, a composition is administered in a therapeutically effective amount and/or according to a dosing regimen that is correlated with a particular desired outcome (e.g., with treating or reducing risk for a muscular dystrophy, such as Duchenne muscular dystrophy).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an anti-Flt-1 antibody or antigen-binding fragment thereof is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a muscular dystrophy, such as Duchenne muscular dystrophy.

In some embodiments, a formulation comprising an anti-Flt-1 antibody or antigen-binding fragment described herein administered as a single dose. In some embodiments, a formulation comprising an anti-Flt-1 antibody or antigen-binding fragment described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an anti-Flt-1 antibody or antigen-binding fragment described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual. In a particular embodiment the anti-Flt-1 antibody, or antigen-binding fragment thereof is administered twice weekly.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an anti-Flt-1 antibody or antigen-binding fragment described herein is administered at regular intervals indefinitely. In some embodiments, a formulation comprising an anti-Flt-1 antibody or antigen-binding fragment described herein is administered at regular intervals for a defined period.

As described herein, the term "therapeutically effective amount" is largely determined based on the total amount of the therapeutic agent contained in the pharmaceutical compositions of the present invention. A therapeutically effective amount is commonly administered in a dosing regimen that may comprise multiple unit doses. For any particular composition, a therapeutically effective amount (and/or an appropriate unit dose within an effective dosing regimen) may vary, for example, depending on route of administration or on combination with other pharmaceutical agents.

In some embodiments, the anti-Flt-1 antibody, or antigen-binding fragment thereof is administered at a dose ranging from about 0.1 mg/kg to about 50 mg/kg. In other embodiments the anti-Flt-1 antibody, or antigen-binding fragment thereof is administered at a dose ranging from about 0.1 mg/kg to about 40 mg/kg, from about 0.1 mg/kg to about 30 mg/kg, from about 0.1 mg/kg to about 20 mg/kg, from about 0.1 mg/kg to about 10 mg/kg, from about 0.1 mg/kg to about 5 mg/kg, from about 0.1 mg/kg to about 3 mg/kg, from about 0.1 mg/kg to about 1 mg/kg, from about 1.0 mg/kg to about 40 mg/kg, from about 1.0 mg/kg to about 30 mg/kg, from about 1.0 mg/kg to about 20 mg/kg, from about 1.0 mg/kg to about 10 mg/kg, from about 1.0 mg/kg to about 5 mg/kg or from about 1.0 mg/kg to about 3 mg/kg. In particular embodiments, the anti-Flt-1 antibody, or antigen-binding fragment thereof is administered at a dose of about 1.0 mg/kg, about 3.0 mg/kg, about 10 mg/kg or about 20 mg/kg.

In some embodiments, administration of an anti-Flt-1 antibody, or antigen-binding fragment thereof reduces the intensity, severity, or frequency, or delays the onset of at least one DMD sign or symptom. In some embodiments administration of an anti-Flt-1 antibody, or antigen-binding fragment thereof reduces the intensity, severity, or frequency, or delays the onset of at least one DMD sign or symptom selected from the group consisting of muscle wasting, skeletal deformation, cardiomyopathy, muscle ischemia, cognitive impairment, and impaired respiratory function.

In some embodiments, administration of an anti-Flt-1 antibody, or antigen-binding fragment thereof improves clinical outcome as measured by a 6 minute walk test, quantitative muscle strength test, timed motor performance test. Brooke and Vignos limb function scales, pulmonary function test (forced vital capacity, forced expiratory volume in 1 second, peak expiratory flow rate, maximal inspiratory and expiratory pressures), health-related quality of life, knee and elbow flexors, elbow extensors, shoulder abduction, grip strength, time to rise from supine position, North Start Ambulatory Assessment, timed 10 meter walk/run, Egen-Klassification scale, Gowers score, Hammersmith motor ability, hand held myometry, range of motion, goniometry, hypercapnia, Nayley Scales of Infant and Toddler Development, and/or a caregiver burden scale.

Combination Therapy

In some embodiments, an anti-Flt-1 antibody or antigen-binding fragment thereof is administered in combination with one or more additional therapeutic agents. In one embodiment the additional therapeutic agent is a corticosteroid, e.g., prednisone. In another embodiment, the additional therapeutic agent is a glucocorticoid, e.g., deflazacort. In another embodiment, the additional therapeutic agent is follistatin or a recombinant protein thereof. In another embodiment the additional therapeutic agent is an RNA modulating therapeutic. The RNA modulating therapeutic may be an exon-skipping therapeutic or gene therapy. The RNA modulating therapeutic may be, for example, Drispersen, PR0044, PR0045, Eteplirsen (AVI-4658), SRP-4053, SRP-4045, SRP-4050, SRP-4044, SRP-4052, SRP-4055 or SRP-4008. In some embodiments the additional therapeutic agent is currently used for treatment of a muscular dystrophy. In other embodiments the additional therapeutic agent may also be used to treat other diseases or disorders. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXAMPLES

Example 1. Generation and Characterization of High Affinity Anti-Flt-1 Antibodies Generation of Antibodies Monoclonal antibodies were generated against soluble Flt-1 using llama monoclonal antibody methodology. Briefly, llamas were immunized with recombinant human soluble Flt-1 (purchased from ABCAM) and the serum was collected.

Antibody Characterization

Antibodies that bound to human and mouse Flt-1 were further characterized for 1) VH family; 2) affinity for Flt-1; 3) IC50; 4) off-rate screening by Biacore assay, 5) cross-reactivity to cynomolgus Flt-1 and 6) binding to VEGF R2 and VEGF R3. Candidate antibodies against human Flt-1 (hFl-1) and mouse Flt-1 (mFlt-1) were characterized as shown in Table 4.

TABLE 4

| Anti-body | VH family | Affinity (nM) hFlt-1 | Affinity (nM) mFlt-1 | IC50 by ELISA (pM) hFlt-1 | IC50 by ELISA (pM) mFlt-1 | Bioassay (% rescue) hFlt-1 | Bioassay (% rescue) mFlt-1 | Human identity (%) VH | Human identity (%) VL |
|---|---|---|---|---|---|---|---|---|---|
| 13B4 | 15 | 0.6 | 1.4 | 13.3 | 500 | >90 | 72.2 | 94.3 | 93.7 |
| 10G12 | 17 | 0.29 | 0.33 | 400 | 300 | 44 | 87.5 | 90.8 | 81 |
| 11A11 | 20 | 0.2 | | 33.3 | | >90 | | 90.8 | 91.1 |

Figure 1B:
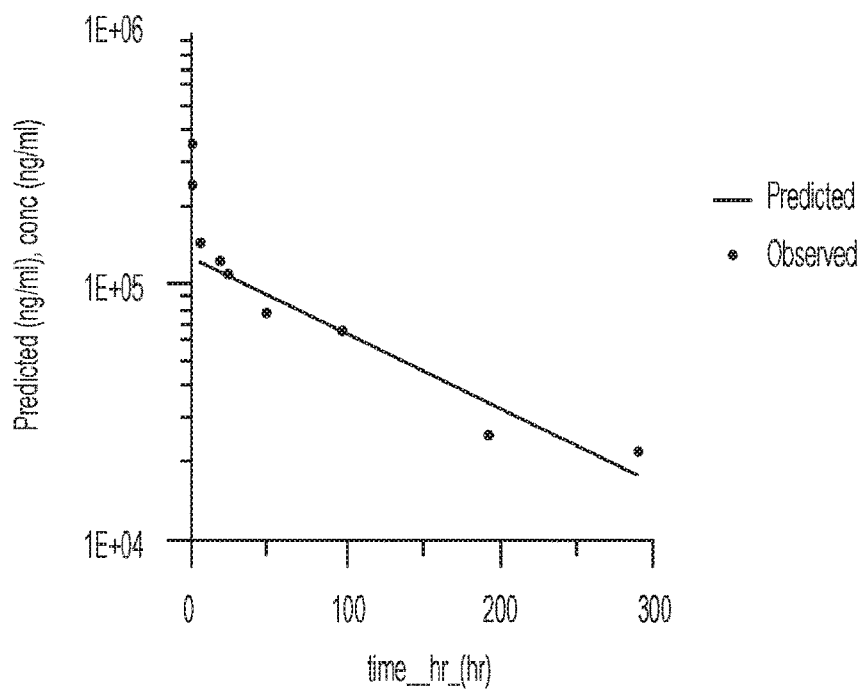
FIG. 1B shows exemplary results depicting clearance of anti-Flt-1 antibody 10G12 after mice were administered the antibody at a dose of 10 mg/kg intravenously.

Pharmacokinetic properties of antibody 13B4 and 10G12 were studied in mice by intravenous administration of 10 mg/kg of each antibody (Table 5). The data demonstrated that antibody 10G12 cannot be detected beyond 288 hours, while antibody 13B4 can be detected at 672 hours (FIGS. 1A-1B).

TABLE 5

| Anti-body | $t_{1/2}$ (h) | Cmax (ng/ml) | Tmax (hr) | AUC $_{0-last}$ (hr*ng/ml) | AUC $_{0-inf}$ (hr*ng/ml) | CL (ml/hr/kg) | $R^2$ |
|---|---|---|---|---|---|---|---|
| 13B4 | 87.7 | 293675 | 1 | 31669464 | 31926743 | 0.31 | 0.960 |
| 10G12 | 99.3 | 359268 | 0.5 | 15999900 | 19120025 | 0.52 | 0.944 |

In Vivo Efficacy of Antibodies

Figure 2A:
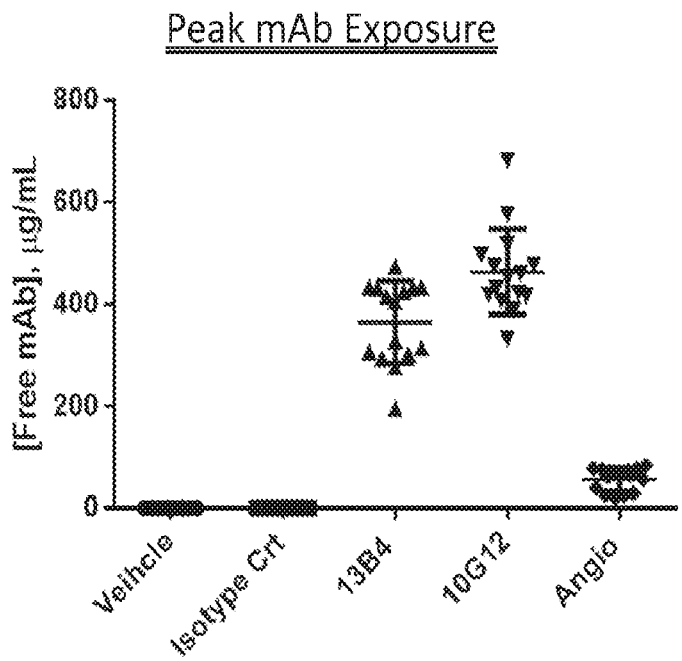
FIG. 2A shows exemplary results depicting peak serum anti-Flt-1 antibody levels.
Figure 2B:
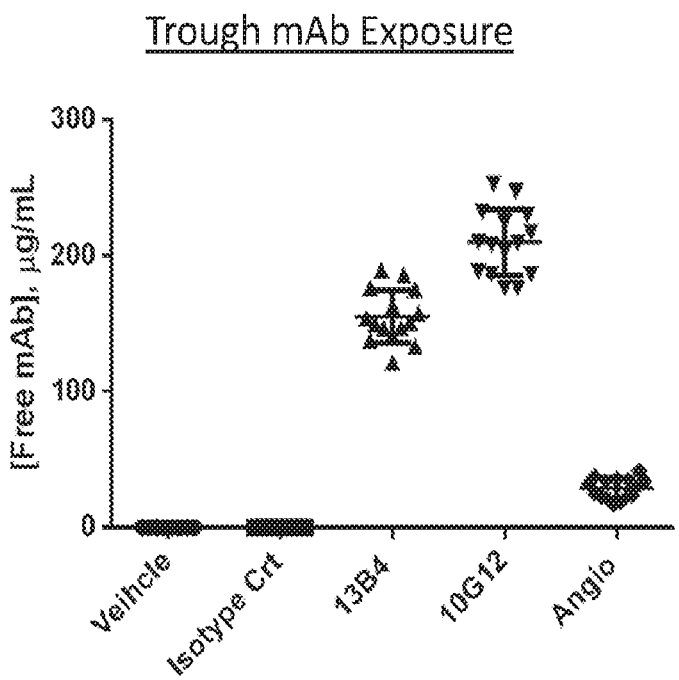
FIG. 2B shows exemplary results depicting trough serum anti-Flt-1 antibody levels.

Mdx mice (i.e., a mouse model of Duchenne muscular dystrophy) were treated with 20 mg/kg of either antibody 13B4 or antibody 10G12 by intravenous administration twice a week for one month beginning at 4 weeks of age. Control mice were treated with vehicle only, an isotype control antibody that does not bind to Flt-1 or a commercial anti-Flt-1 antibody known as Flt-1:VEGF antagonist (Angio Proteomie, catalog number AP-MAB0702). To assess serum antibody concentration at a trough exposure point, blood was collected 4 days after the fifth intravenous dose. To assess serum antibody concentration at a peak exposure point, blood was collected 24 hours after the last dose. Peak and trough concentration of antibodies 13B4 and 10G12 are shown in FIGS. 2A and 2B. The concentration of free antibody 13B4 and free antibody 10G12 in blood was higher than that of the isotype control antibody and the commercial control antibody at both the peak and trough exposure time points.

Figure 3:
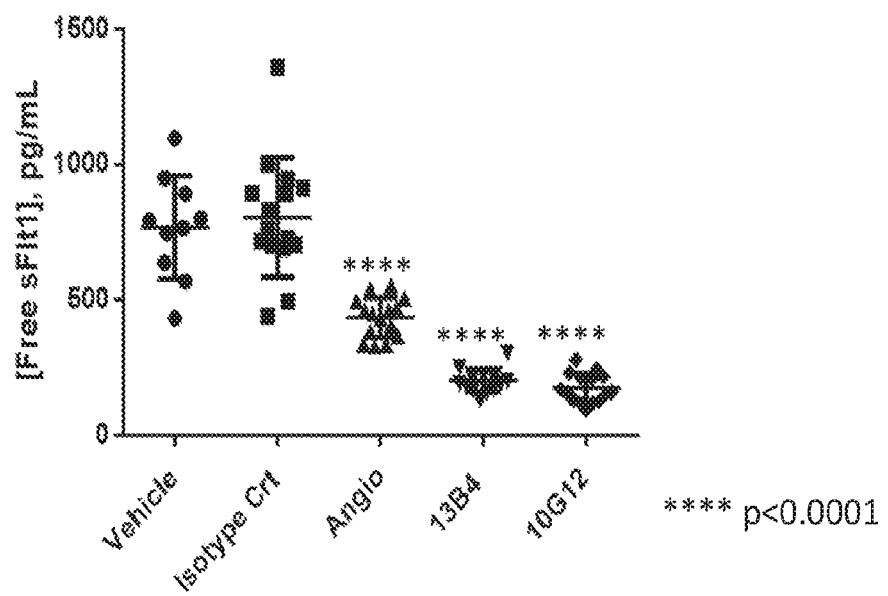
FIG. 3 shows exemplary results depicting a decrease in free soluble Flt-1 (sFlt-1) levels in serum following administration of an anti-Flt-1 antibody (13B4 or 10G12), isotype control antibody, commercial antibody (Angio) or vehicle alone to mdx mice.
Figure 4:
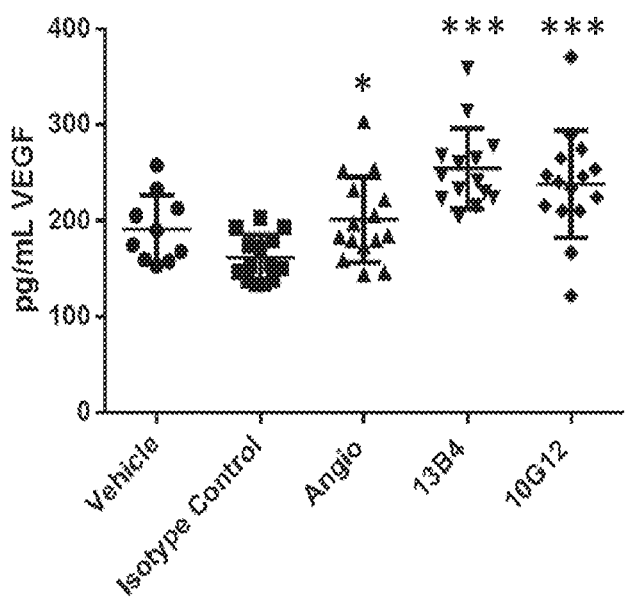
FIG. 4 shows exemplary results depicting an increase in serum VEGF levels following administration of an anti-Flt-1 antibody (13B4 or 10G12), isotype control antibody, commercial antibody (Angio) or vehicle alone to mdx mice.
Figure 5A:
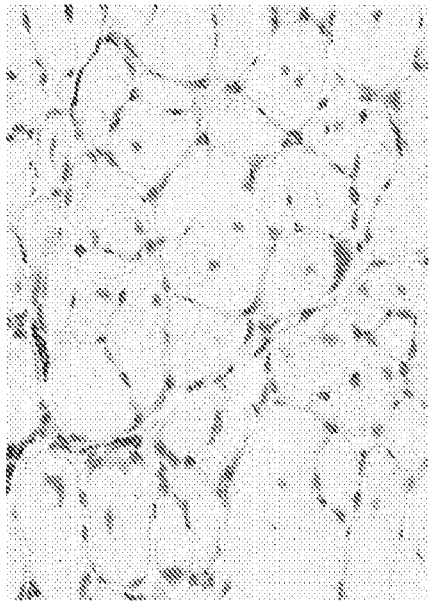
FIGS. 5A-5D show exemplary results of CD31 staining of tissue sections obtained from the diaphragm muscle of mdx mice administered an anti-Flt-1 antibody (13B4 or 10G12), isotype control antibody or commercial antibody (Angio).
Figure 5B:
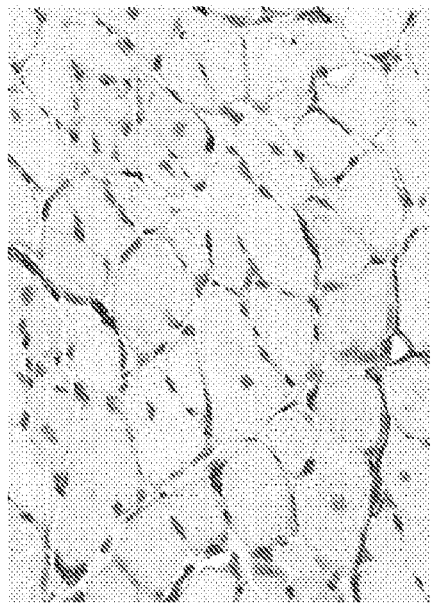
Figure 5C:
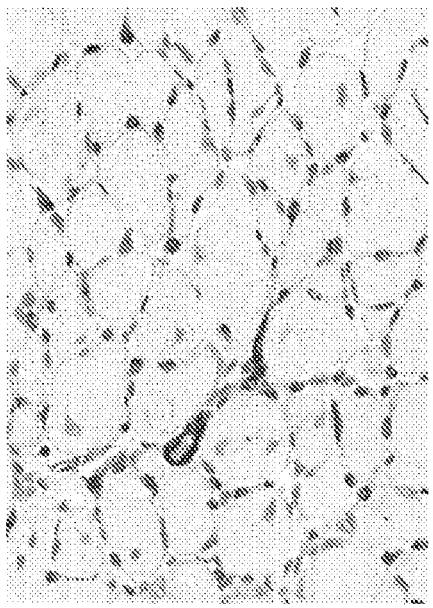
Figure 5D:
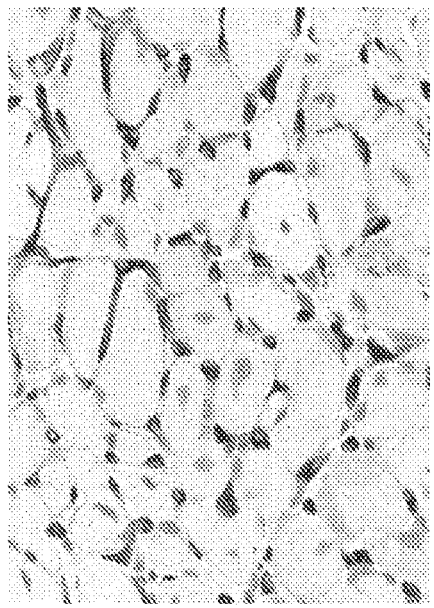

To assess serum free sFlt-1 levels and VEGF levels, blood was collected 24 hours after the fifth intravenous dose and prior to sacrifice. Administration of antibody 13B4 and antibody 10G12, as well as the commercial control antibody, significantly decreased the serum concentration on sFlt-1 ($p<0.0001$) as compared to the isotype control antibody (FIG. 3). Administration of antibody 13B4 and antibody 10G12, resulted in a significant increase in serum levels of VEGF as compared to the isotype control antibody ($p<0.001$) (FIG. 4). Administration of the commercial control antibody also resulted in a significant increase in blood levels of VEGF as compared to the isotype control antibody ($p<0.05$) (FIG. 4).

Histopathology

Figure 6A:
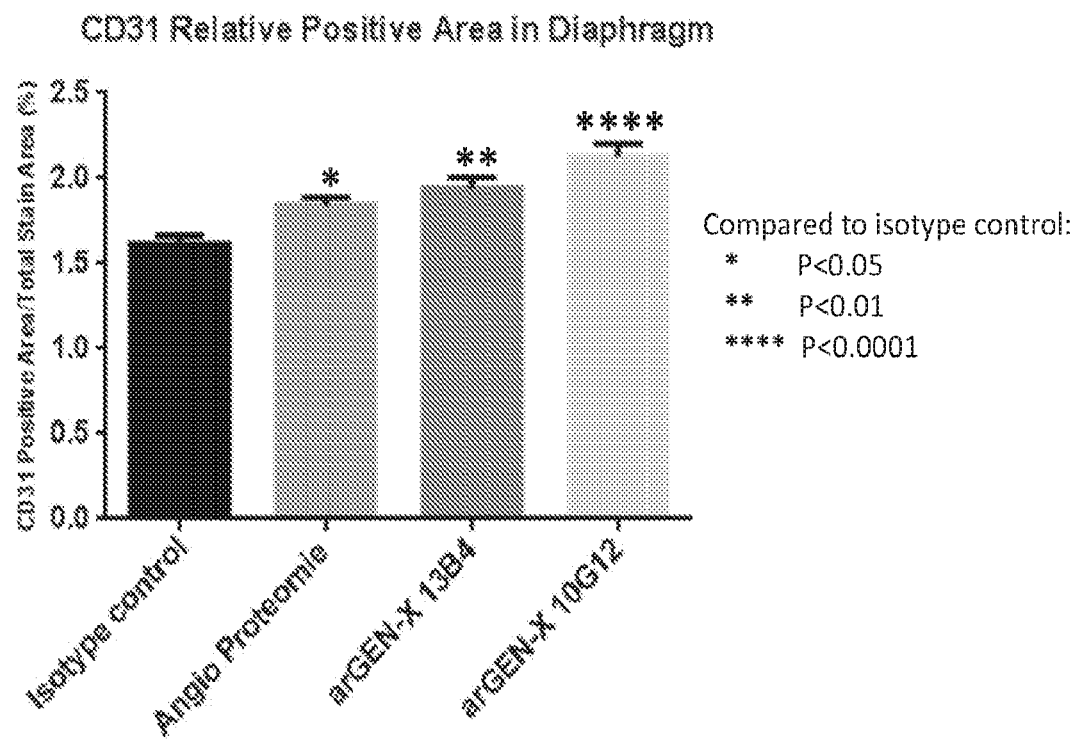
FIG. 6A shows exemplary results of quantification of the CD31 positive area as a percentage of the total stained area in tissue sections obtained from diaphragm muscle.
Figure 6B:
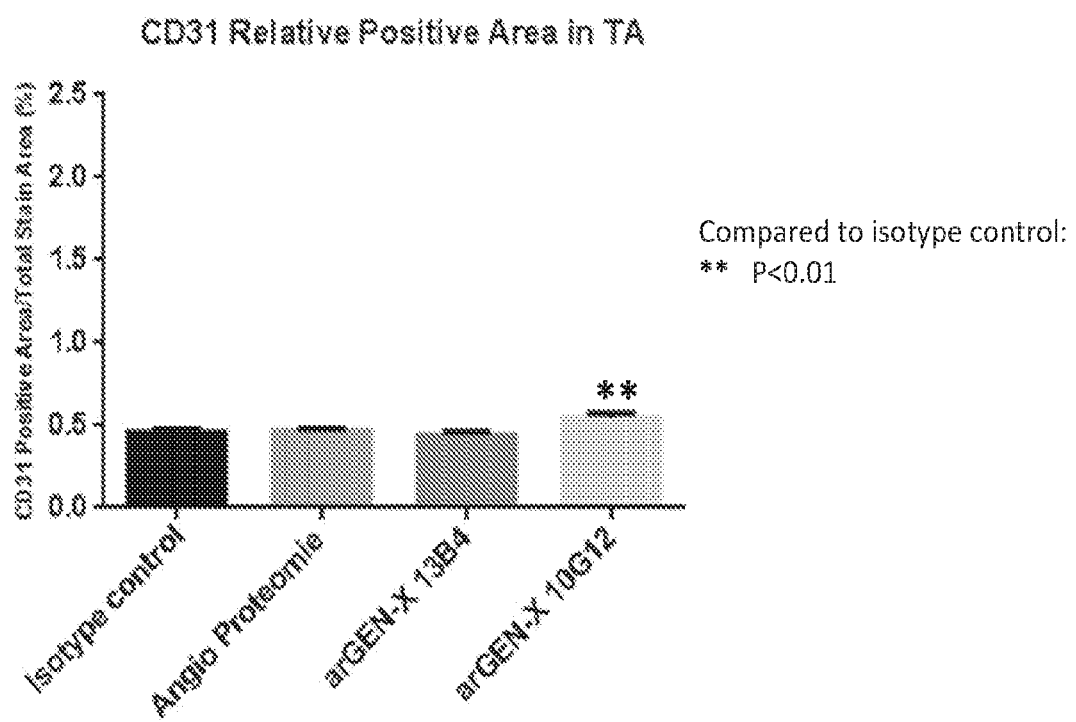
FIG. 6B shows exemplary results of quantification of the CD31 positive area as a percentage of the total stained area in tissue sections obtained from the tibialis anterior (TA) muscle.

Mice were sacrificed at the end of the 30 day treatment period and the diaphragm muscle and tibialis anterior (TA) muscle were collected and sectioned to determine if the anti-Flt-1 antibodies induced angiogenesis in skeletal muscle. Sections of muscle were stained with the endothelial cell marker CD31. A significant increase in capillary density was seen in the diaphragms of mice treated with antibody, 13B4, 10G12 or the commercial control antibody as compared to the diaphragms of mice treated with the isotype control antibody (FIGS. 5A-5D). The data were quantified using automated quantitative imaging software as shown in FIGS. 6A-6B. There was a significant increase in the CD31 positive area in diaphragms of mice treated with the commercial control antibody ($p<0.05$), antibody 13B4 ($p<0.01$) and antibody 10G12 ($p<0.0001$) as compared to the diaphragms of mice treated with the isotype control antibody. A significant increase in the CD31 positive area of the tibialis anterior (TA) muscle of mice treated with antibody 10G12 ($p<0.01$) as compared to the tibialis anterior muscle of mice treated with the isotype control antibody was also demonstrated.

This studies demonstrated that administration of an Flt-1 antibody (e.g., 10G12 and 13B4) to mdx mice resulted in a significant increase in endothelial cell proliferation as well as a decrease in soluble Flt-1 in serum and an increase in serum VEGF concentrations. These antibodies demonstrated binding affinity for the Flt-1 target in the pM range (see Table 4), IC50 for Flt-1 binding of less than 100 pM (see Table 4) and greater than 50% rescue of VEGF signaling in a bioassay.

Example 2. Generation and Characterization of High Affinity Anti-Flt-1 Antibodies Additional anti-Flt-1 monoclonal antibodies were generated as described above. These antibodies were further characterized for binding affinity to sFlt-1 antigen (by ELISA and Biacore), competition for VEGF in a sFlt-1:VEGF competition ELISA; and performance in a cell based assay.

Antibody Characterization—Binding to Target

Figure 7:
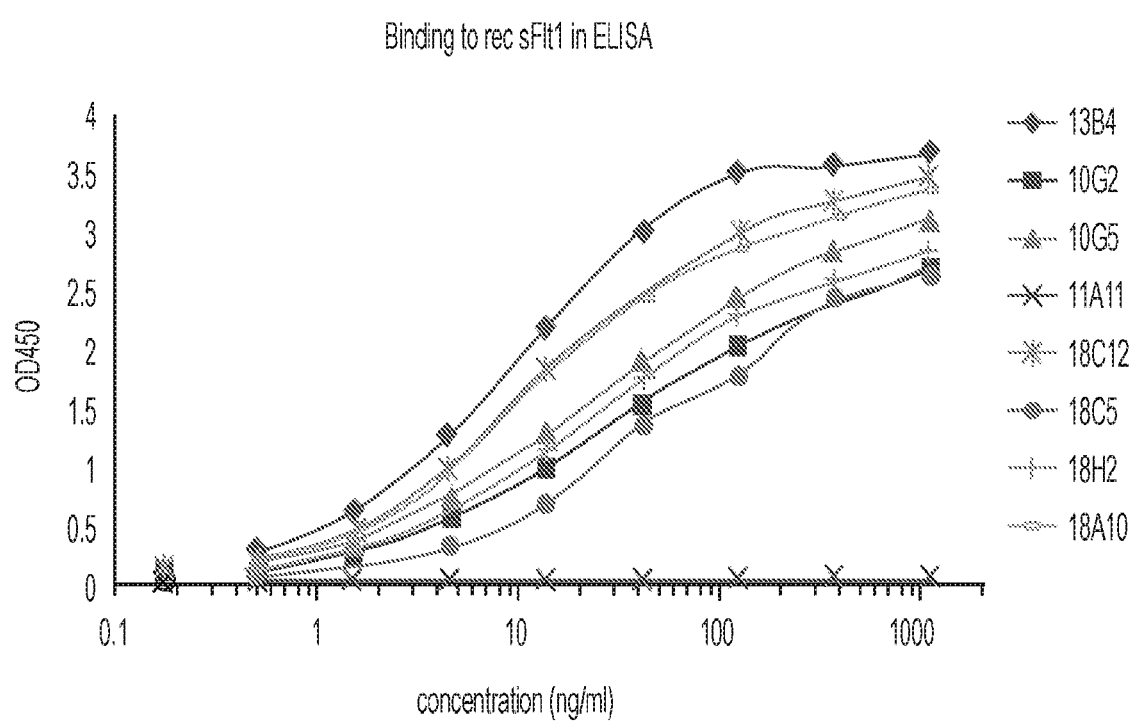
FIG. 7 shows exemplary results depicting binding of anti-Flt-1 antibodies to recombinant sFlt-1 by an ELISA assay.

The monoclonal anti-Flt-1 antibodies were assayed for binding to recombinant sFlt-1 antigen in an ELISA assay (FIG. 7). All antibodies demonstrated a dose-dependent increase in binding. Binding affinity of the anti-Flt-1 antibodies to mouse and human Flt-1 antigen was measured by surface plasmon resonance methodology (i.e., Biacore) (Table 6). The antibodies bound to human Flt-1 in the nanomolar range with antibody 11A11 demonstrating the highest binding affinity for human Flt-1. Biacore analysis also demonstrated that the antibodies did not cross-react with VEGF R2 or VEGF R3 (Table 6), however all antibodies did cross react with cynomolgus Flt-1.

TABLE 6

|  | Family | Affinity (nM) | | Binding | |
|---|---|---|---|---|---|
|  |  | Human | Mouse | VEGFR2 | VEGFR3 |
| 13B4 | 15 | 0.58 | 1.4 | — | — |
| 10G2 |  | 1.5 | 1.4 | — | — |
| 10G5 |  | 1.6 | 4.2 | — | — |
| 18H2 |  | 1.8 | 3.2 | — | — |
| 18A10 |  | 1.2 | 2 | — | — |
| 18C5 |  | 2.7 | 9.2 | — | — |
| 18C12 |  | 1.4 | 2 | — | — |
| 18B6 | 21 | 1.7 | 1.2 | — | — |
| 16B3 | 19 | 2.7 | 3 | — | — |
| 10G12 | 17 | 3.1 | 6.9 | — | — |
| 16B12 | 18 | 2.7 | 5.7 | — | — |
| Angio |  | 2.3 | 8.2 |  |  |
| 11A11 | 20 | 0.16 |  | — | — |

Antibody Characterization—Competition/Antagonism

Figure 8:
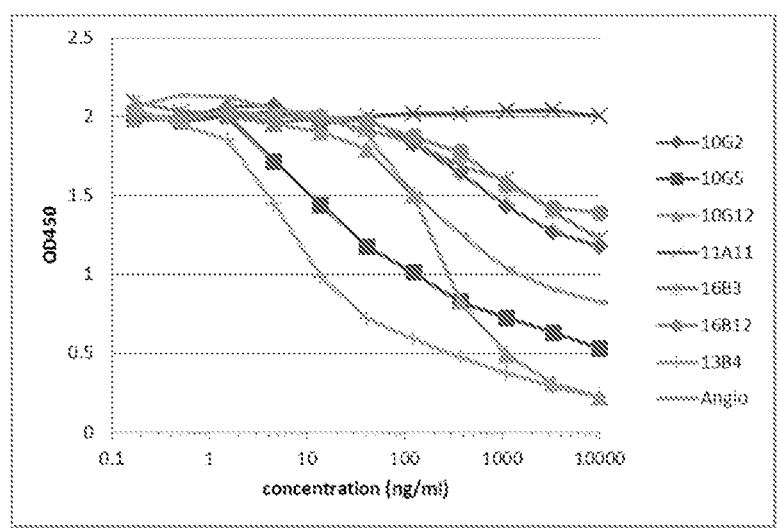
FIG. 8 shows exemplary results depicting inhibition of binding of sFlt-1 to VEGF by anti-Flt-1 antibodies in a competition ELISA assay.

To estimate the potency of the antibodies, the antibodies were assay in a competition ELISA using human sFlt-1 and VEGF. Antibody concentrations tested ranged from 0.1 mg/mL to 10,000 ng/mL. The commercial anti-Flt-1 antibody served as a control. With the exception of 11A11, all antibodies were able to prevent binding of VEGF to sFlt-1 (FIG. 8).

Antibody Characterization—Cell Based Assay

Figure 9:
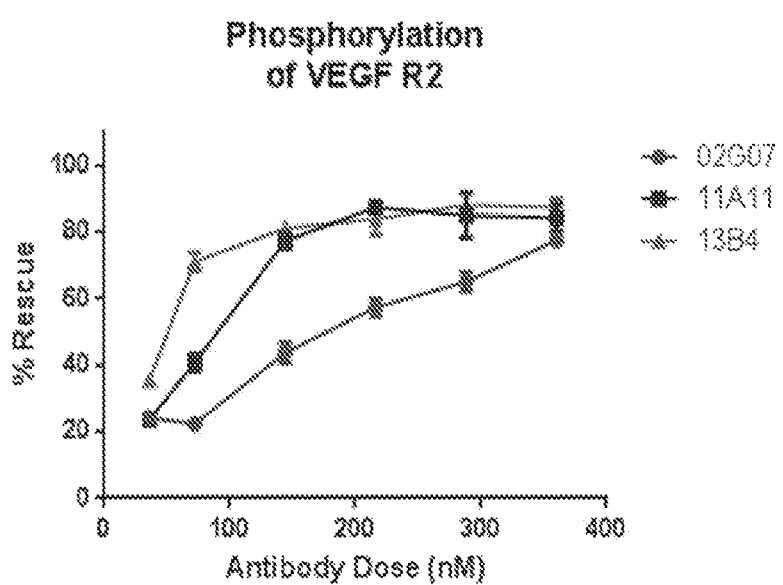
FIG. 9 shows exemplary results depicting rescue of phosphorylation of VEGF R2 by anti-Flt-1 antibodies. Human primary vein endothelial cells (HUVECs) were treated with VEGF in the presence of sFlt-1 and anti-Flt-1 antibodies and the level of VEGF R2 phosphorylation was determined. Percent rescue indicates the level of phosphorylation of VEGF R2 relative to the level of phosphorylation of VEGF R2 when HUVECs were treated with VEGF and sFlt-1 alone (i.e., no anti-Flt-1 antibody).

Human primary vein endothelial cells (HUVECs) were stimulated with VEGF in the presence of sFlt-1 and monoclonal antibodies 02G07, 11A11 and 13B4. VEGF induced activation of cells was assayed by determining the phosphorylation status of the VEGF R2 receptor. The data are expressed as a percent rescue of the phosphorylation of the VEGF R2 receptor relative to the phosphorylation of the VEGF R2 receptor in the presence of sFlt-1 alone (e.g., without anti-Flt-1 antibodies). The monoclonal antibodies rescued cell activation (i.e., phosphorylation) by antagonizing soluble Flt-1 (FIG. 9).

Example 3. Characterization of High Affinity Anti-Flt-1 Antibodies Generated by Light Chain Shuffling Light chain shuffling of antibodies 18B6, 11A11 and 13B4 described in Example 2 was performed to increase the affinity and potency of the candidate antibodies.

Antibody Characterization—Binding to Target

The resulting antibodies displayed increased affinity for the Flt-1 antigen. For instance the $K_D$ of antibody 21C6 increased approximately 10-fold over that of the parent antibody, 11A11. Similarly, the $K_D$ of antibody 21B3 increased approximately 5-fold over that of the parent antibody, 13B4 (Table 7).

TABLE 7

|  | ka (1/Ms) | kd (1/s) | KD (M) |
|---|---|---|---|
| 18B6 | 3.95E+05 | 3.25E−04 | 8.22E−10 |
| 24A8 | 2.24E+05 | 1.35E−04 | 6.05E−10 |
| 21F9 | 2.84E+05 | 2.42E−04 | 8.52E−10 |
| 11A11 | 3.17E+05 | 5.32E−05 | 1.68E−10 |
| 21C6 | 1.31E+06 | 2.62E−05 | 2.00E−11 |
| 21B6 | 7.59E+05 | 6.50E−05 | 8.57E−11 |
| 13B4 | 4.16E+05 | 1.62E−04 | 3.89E−10 |

TABLE 7-continued

|  | ka (1/Ms) | kd (1/s) | KD (M) |
|---|---|---|---|
| 21B3 | 5.58E+05 | 4.73E-05 | 8.48E-11 |
| 21A1 | 2.23E+05 | 1.15E-04 | 5.16E-10 |
| 21D1 | 8.44E+05 | 1.44E-04 | 1.71E-10 |
| 21B4 | 4.96E+05 | 1.58E-04 | 3.19E-10 |
| 19H6 | 3.32E+05 | 1.09E-04 | 3.29E-10 |

Antibody Characterization—Competition/Antagonism

Figure 10:
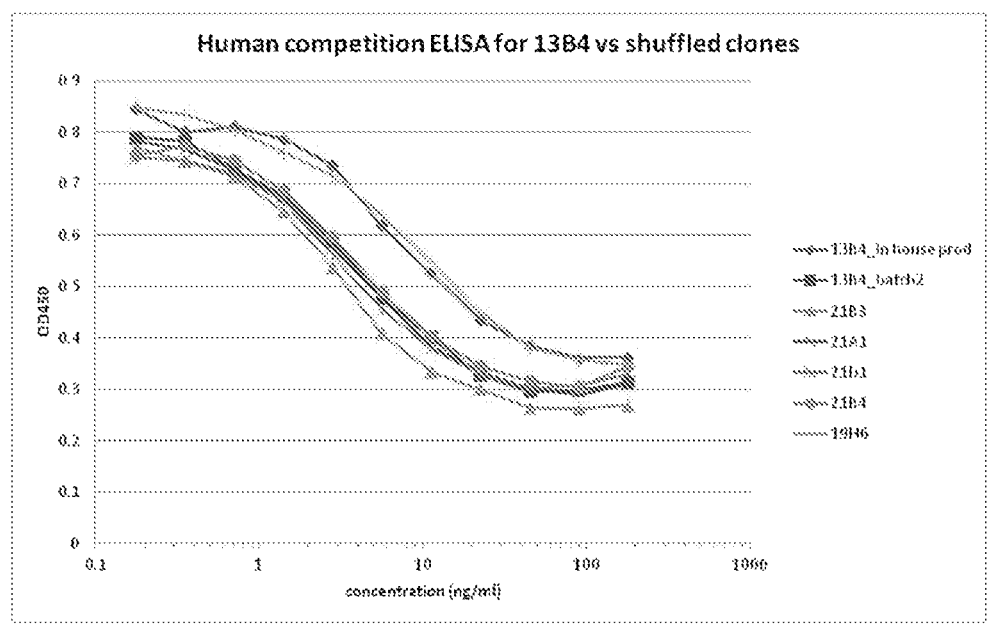
FIG. 10 shows exemplary results depicting inhibition of binding of soluble Flt-1 to VEGF by anti-Flt-1 antibodies in a competition ELISA assay.

To estimate the potency of the antibodies following the light chain shuffling, the antibodies were assay in a competition ELISA using human sFlt-1 and VEGF. Antibody concentrations tested ranged from 0.2 mg/mL to 200 ng/mL. The ability of parent antibody 13B4 to competitively bind sFlt-1 was compared to that of antibodies generated by light chain shuffling. All antibodies demonstrated a dose dependent inhibition of binding of VEGF to human sFlt-1 with clone 21B3 the most effective competitor (FIG. 10).

In Vivo Efficacy

Figure 11:
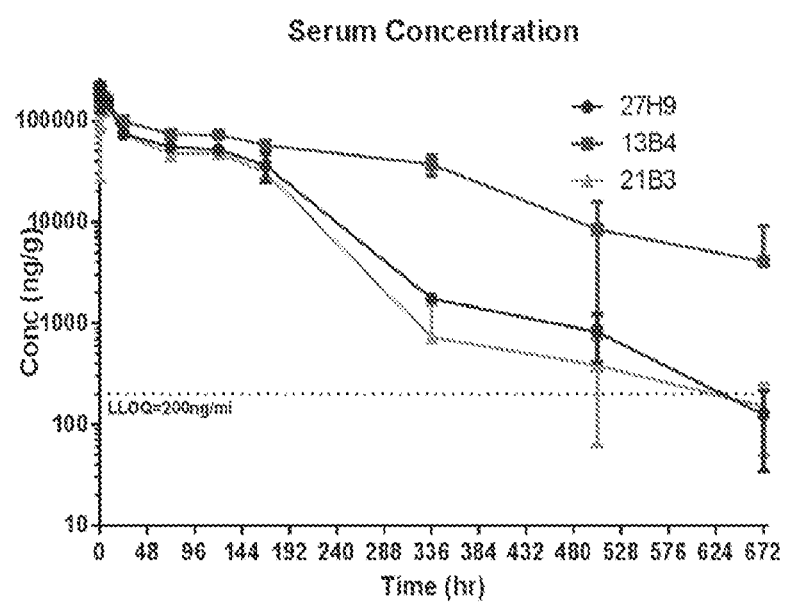
FIG. 11 shows exemplary results depicting clearance of anti-Flt-1 antibodies from the serum over 672 hours after mice were administered the anti-Flt-1 antibody at a dose of 10 mg/kg intravenously.

To determine the serum half-life and pharmacokinetic characteristics of the light chain shuffled antibodies, mice were administered a single 10 mg/kg dose of light chain shuffled antibodies 27H9 and 21B3 and parent antibody 13B4 each labeled with $I^{125}$. Serum was collected at 0.083, 0.25, 0.5, 1, 4, 8, and 24 hours and at 3, 5, 7, 14, 21 and 28 days and the serum concentration of the antibodies determined. The serum half-life was reduced in the light shuffled antibodies as compared to the parent antibody (FIG. 11). However, the light chain shuffled antibodies showed improved pharmacodynamic characteristics as compared to the parent. For instance, antibody 27H9 reached a maximum concentration of 222.4 ug/mL by 0.083 hours whereas the parent antibody 13B4 reached a maximum concentration of 217 ug/mL by 0.5 hours (Table 8).

TABLE 8

| TA | T1/2 (hr) | Cmax (ug/ml) | Tmax (hr) | AUC0-last (hr*ug/ml) | AUC 0-inf (hr*ug/ml) | Vss (ml/kg) | Cl (ml/hr/kg) | V0 (ml/kg) | R2 |
|---|---|---|---|---|---|---|---|---|---|
| 13B4 | 129.4 | 217.3 | 0.5 | 27044 | 27798 | 71 | 0.36 | 48.7 | 0.97 |
| 21B3 | 56.5 | 215.8 | 0.083 | 12590 | 12602 | 73 | 0.79 | 42.9 | 0.95 |
| 27H9 | 62.8 | 222.4 | 0.083 | 14318 | 14329 | 68 | 0.7 | 44.3 | 0.96 |

Histopathology

Figures 12A, 12B, 12C, 12D, 12E, 12F:
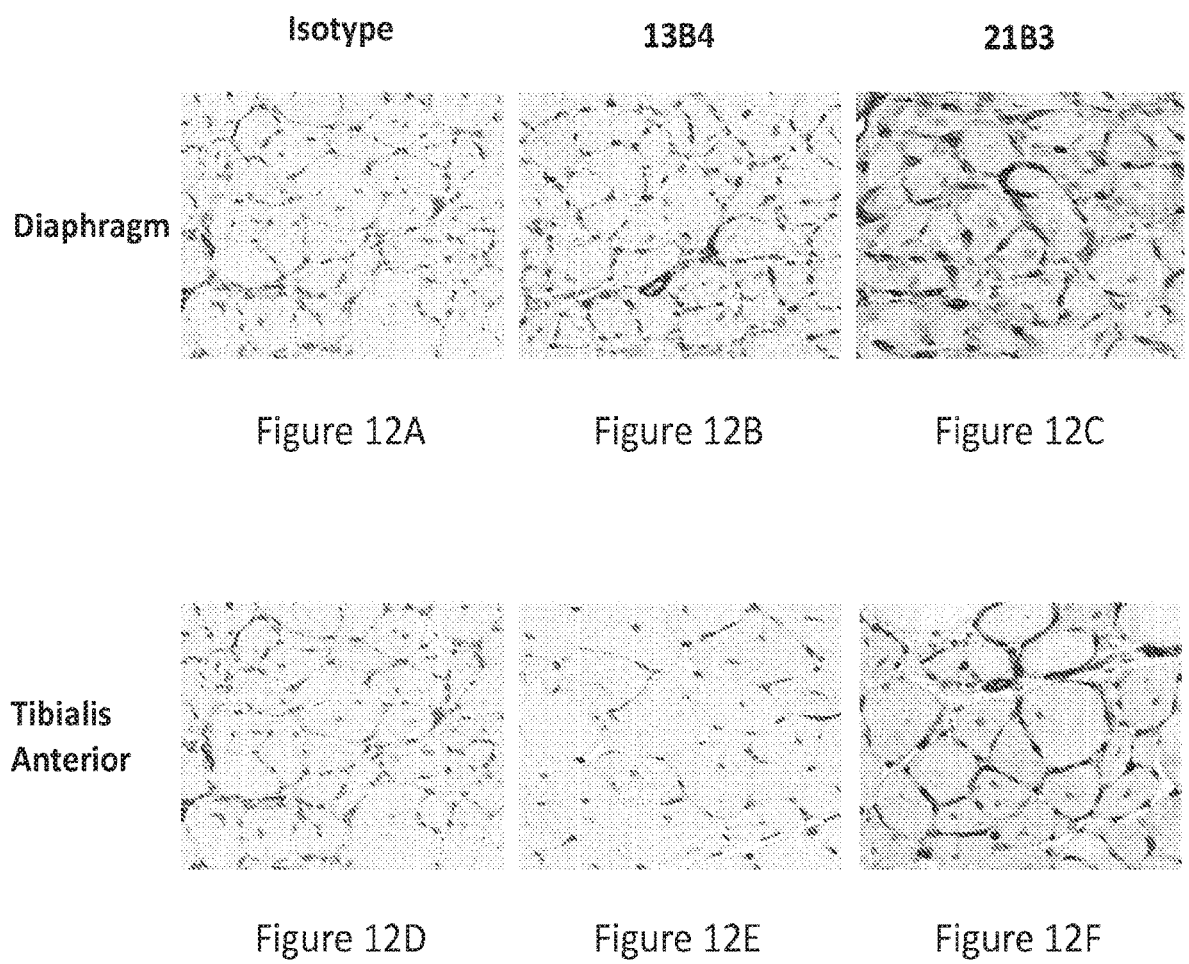
FIGS. 12A-12C show exemplary results of CD31 staining of tissue sections from diaphragm muscle.
FIGS. 12D-12F show exemplary results of CD31 staining of tissue sections obtained from tibialis anterior muscle.

To determine if the light chain shuffled and parent antibodies could induce endothelial cell proliferation, mdx mice were treated with 20 mg/kg of antibody biweekly for 4 weeks by intravenous administration. Mice were sacrificed at the end of the treatment period and the diaphragm and tibialis anterior muscles were collected and sectioned to determine if the antibodies induced angiogenesis in skeletal muscle. Sections of muscle were stained with the endothelial cell marker CD31. A significant increase in capillary density in the diaphragm was seen in the mice treated with antibody 13B4 and 21B3 as compared to the diaphragms of mice treated with the isotype control antibody (FIGS. 12A-12C). In addition, there was a significant increase in capillary density in the tibialis anterior from mice treated with the light chain shuffled antibody 21B3 as compared to the tibialis anterior muscle from mice treated with the isotype control antibody (FIGS. 12D-12F).

Figure 13A:
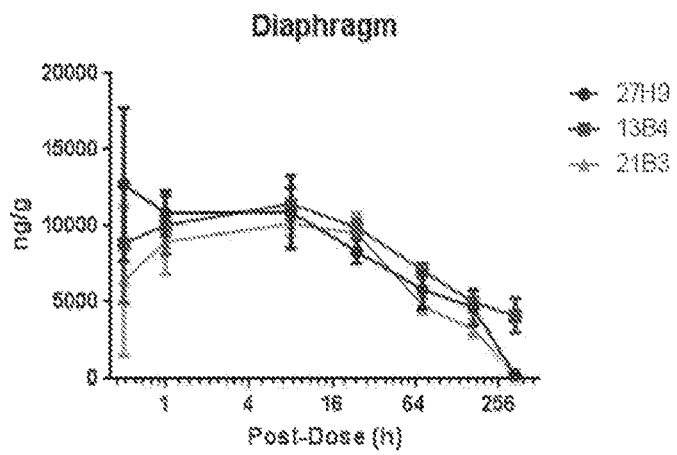
FIGS. 13A-13C show exemplary biodistribution of anti-Flt-1 antibodies 27H9, 13B4 and 21B3 in the diaphragm, tibialis and gastrocnemius muscles of mice over a 256 hour time course following administration of the antibody.
Figure 13B:
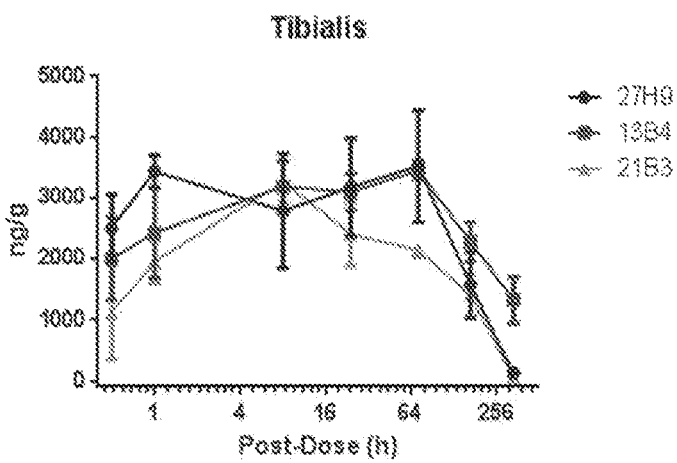
Figure 13C:
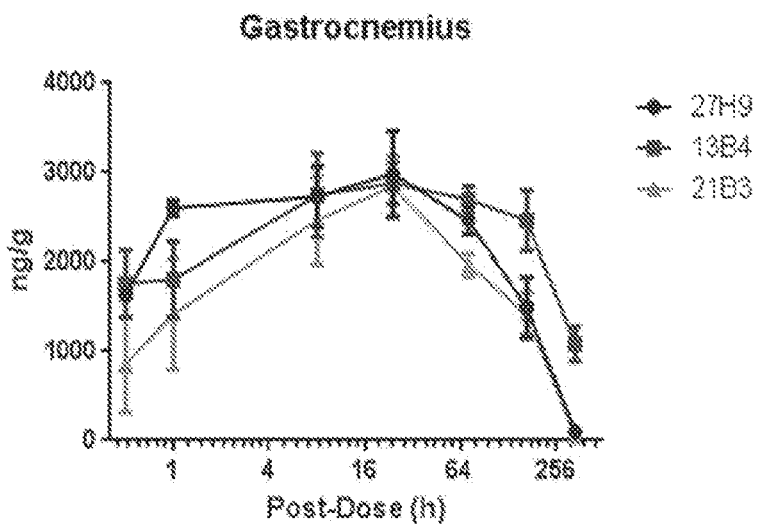

The biodistribution of antibodies 27H9, 13B4 and 21B3 in the diaphragm, tibialis and gastrocnemius muscles was determined using $^{125}I$ labeled antibodies. The diaphragm showed the highest exposure for all antibodies over the time course (FIGS. 13A-13C).

These studies demonstrated that administration of an Flt-1 antibody (i.e., 13B4 and 21B3) to mdx mice resulted in a significant increase in endothelial cell proliferation.

Example 4. In Vivo Efficacy of High Affinity Anti-Flt-1 Antibody 21B3

Figure 14A:
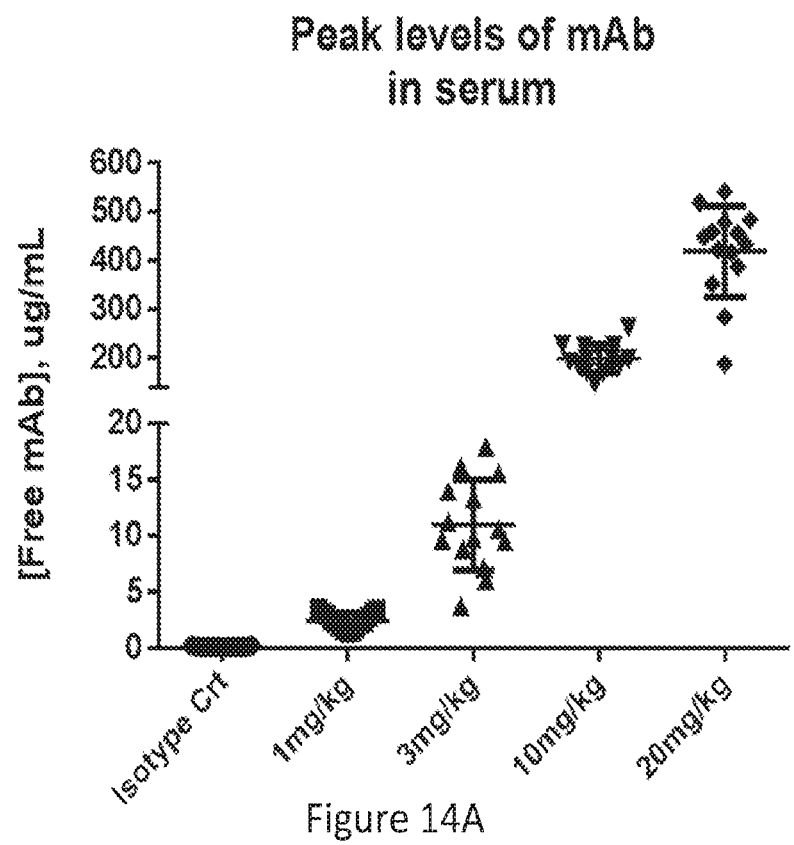
FIG. 14A shows exemplary results depicting peak anti-Flt-1 antibody 21B3 levels at peak exposure.
Figure 14B:
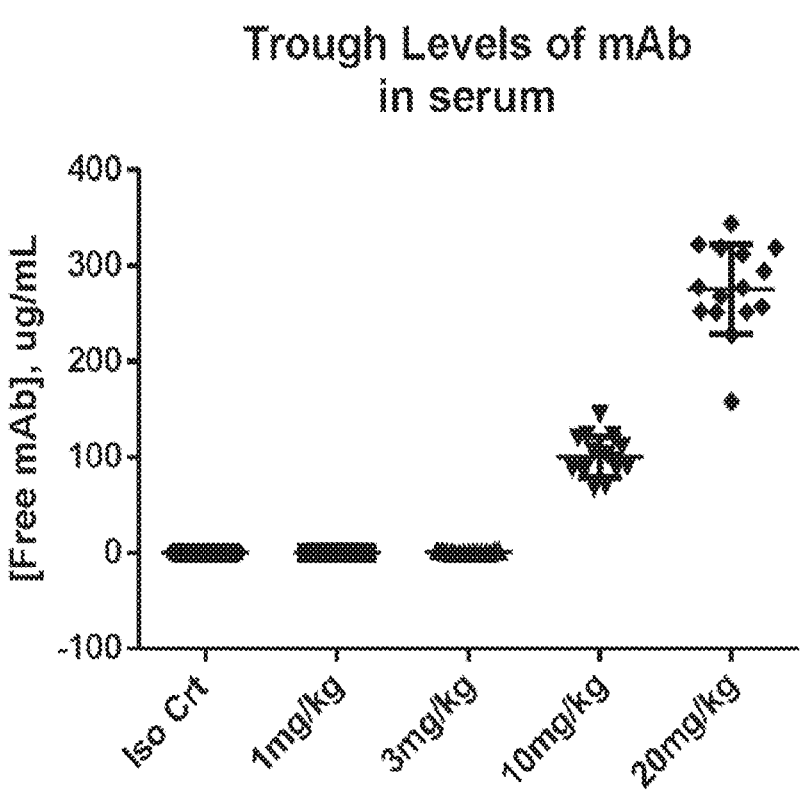
FIG. 14B shows exemplary results depicting trough anti-Flt-1 antibody 21B3 levels.

Mdx mice were treated with 1, 3, 10 or 20 mg/kg of antibody 21B3, or 20 mg/kg of an isotype control antibody, by intravenous administration twice a week for one month beginning at 4 weeks of age. To assess serum antibody concentration at a trough exposure point, blood was collected 4 days after the fifth intravenous dose. To assess blood antibody concentration at a peak exposure point, blood was collected 24 hours after the last dose. Peak and trough serum concentrations of antibody 21B3 and the isotype control antibody are shown in FIGS. 14A and 14B. The peak and trough levels of antibody 21B3 were dose dependent and higher than the isotype control antibody.

Figure 15:
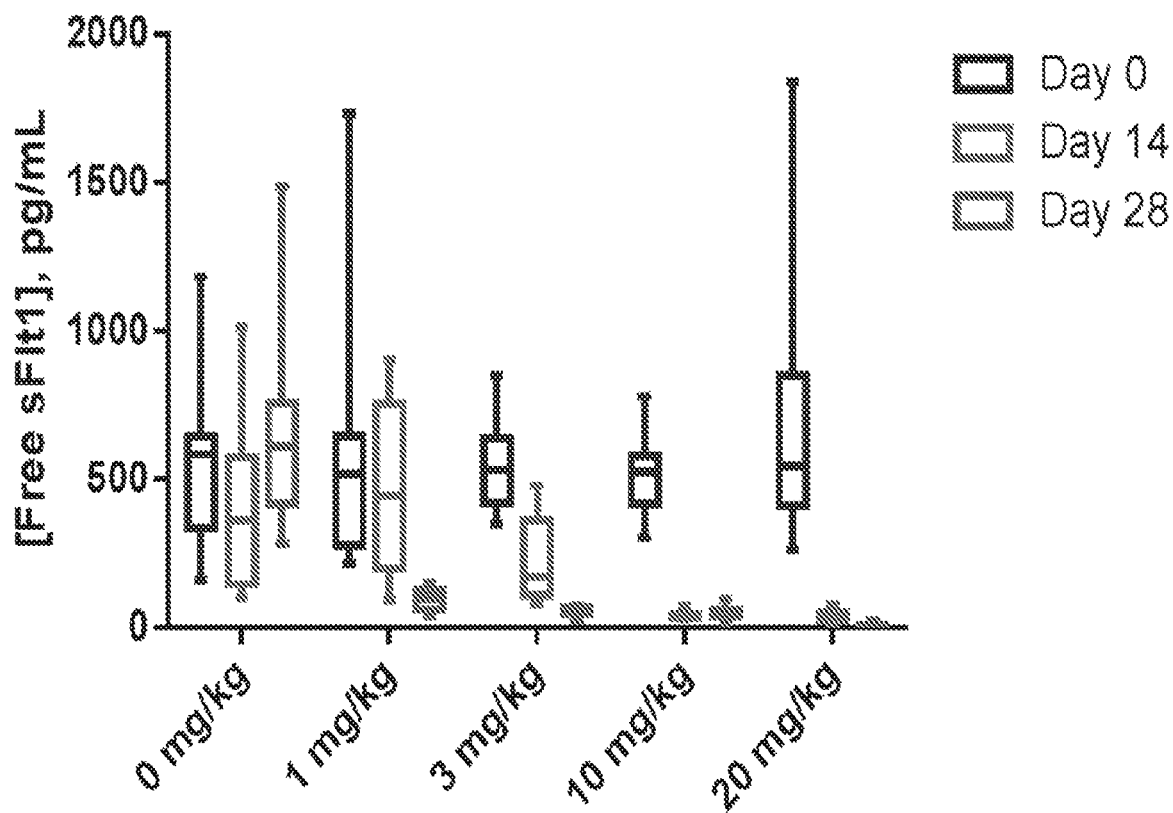
FIG. 15 shows exemplary results depicting free sFlt-1 following administration of anti-Flt-1 antibody 21B3 to mdx mice.

To assess serum levels of free sFlt-1, blood was collected on days 0, 14 and 28. Administration of antibody 21B3 induced a dose dependent decrease in serum free sFlt-1 levels. The response was more durable at the 10 and 20 mg/kg doses as seen at both day 14 and day 28. However, a statistically significant decrease was observed is free sFlt-1 levels at the 3, 10 and 20 mg/kg doses as compared to the free sFlt-1 level in mice treated with vehicle alone (FIG. 15).

Figure 16:
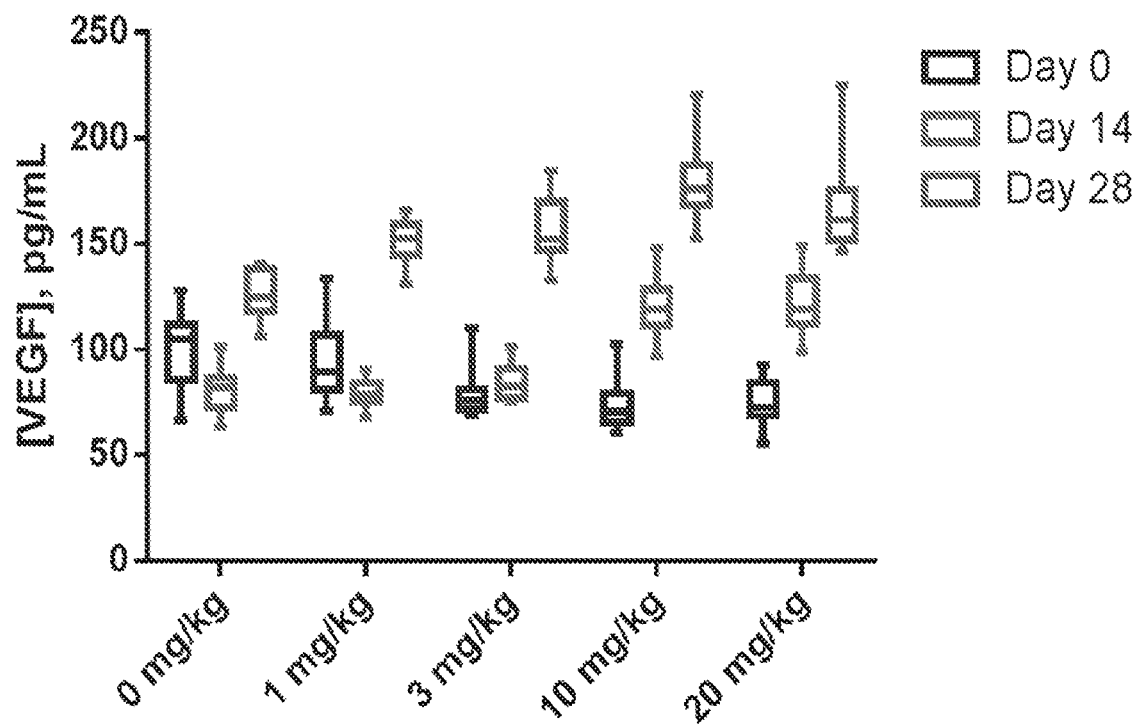
FIG. 16 shows exemplary results depicting VEGF levels following administration of anti-Flt-1 antibody 21B3 to mdx mice.
Figure 17A:
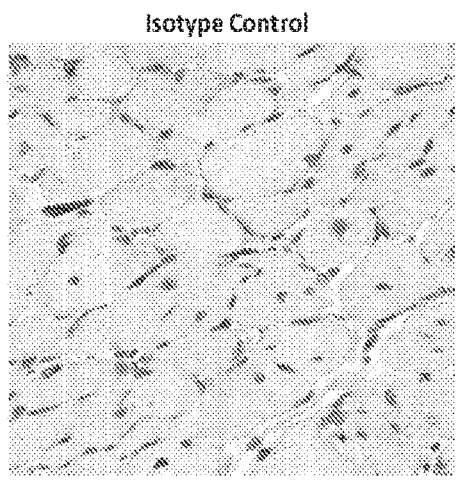
FIG. 17A-17E shows exemplary results of CD31 staining of tissue sections obtained from the diaphragm muscle of mdx mice administered anti-Flt-1 antibody 21B3 or isotype control antibody.
Figure 17B:
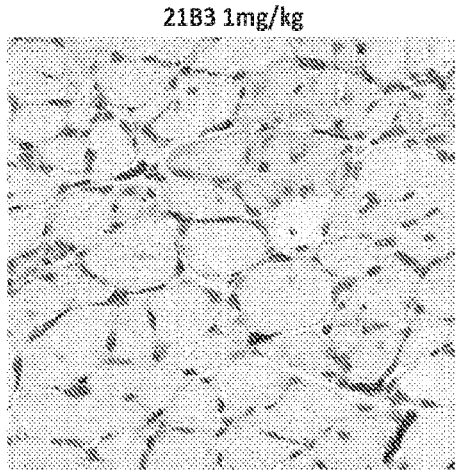
Figure 17C:
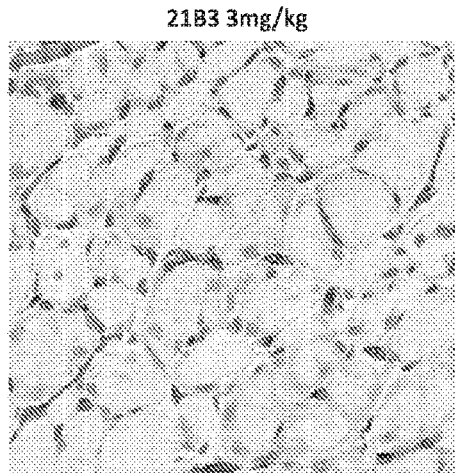
Figure 17D:
Figure 17E:
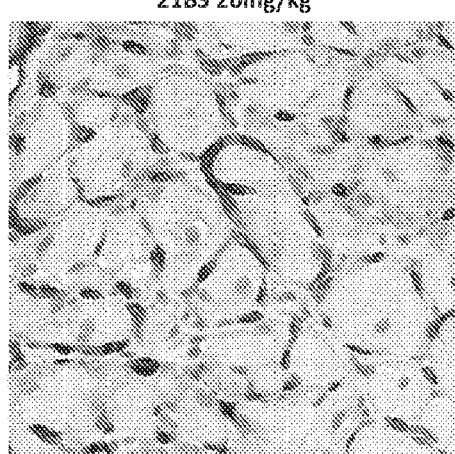

To assess serum levels of VEGF, blood was collected on days 0, 14 and 28. Administration of antibody 21B3 induced a dose dependent increase in serum VEGF levels. As observed for the free sFlt-1 levels, the response was more durable at the 10 and 20 mg/kg doses and at both day 14 and day 28. In fact, a statistically significant increase in serum VEGF was observed at the 10 and 20 mg/kg doses of antibody 21B3 as compared to serum VEGF levels in mice treated with vehicle alone (FIG. 16).

Histopathology

Figure 18:
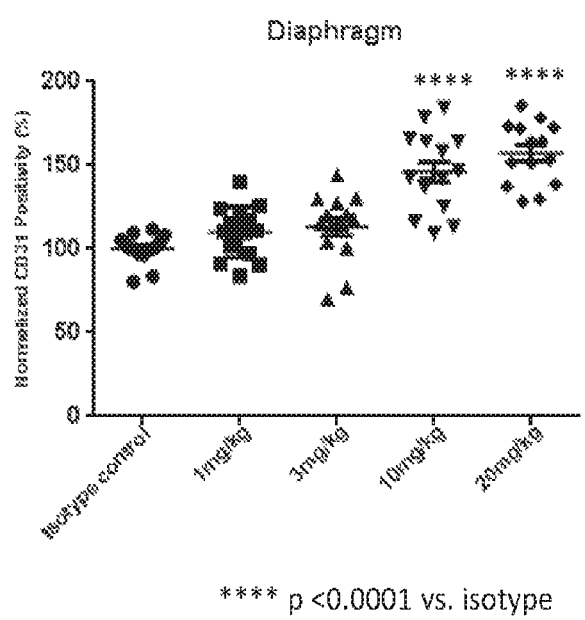
FIG. 18 shows exemplary results of quantification of the normalized CD31 positivity percentage in tissue sections obtained from the diaphragm muscle of mdx mice administered anti-Flt-1 antibody 21B3 or isotype control antibody.
Figure 19A:
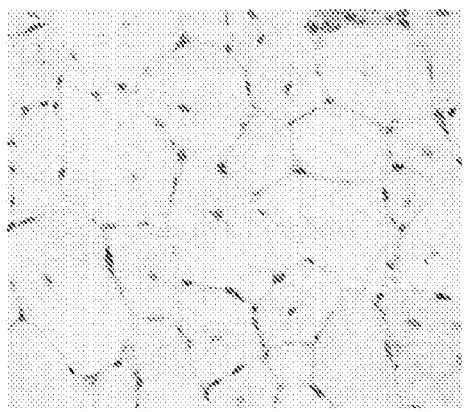
FIG. 19A-19E shows exemplary results of CD31 staining of tissue sections obtained from the tibialis anterior muscle of mdx mice administered anti-Flt-1 antibody 21B3 or isotype control antibody.
Figure 19B:
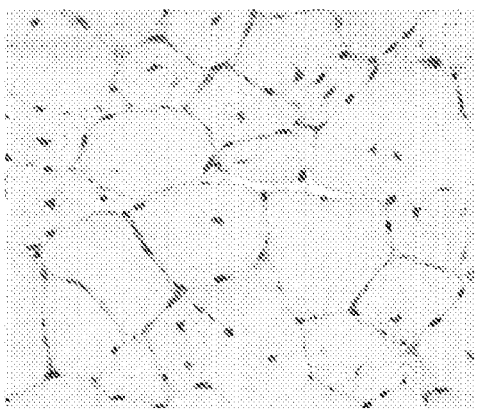
Figure 19C:
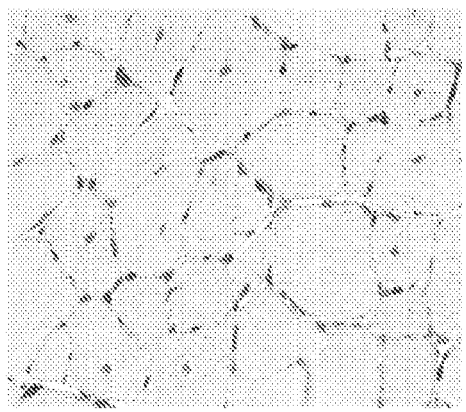
Figure 19D:
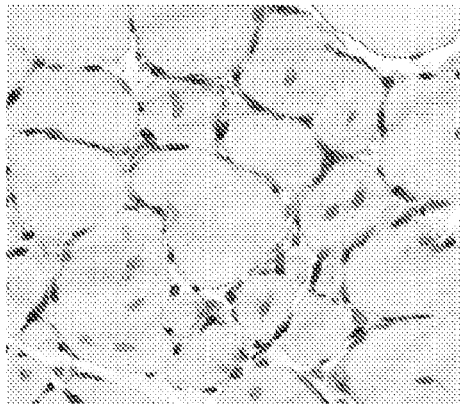
Figure 19E:
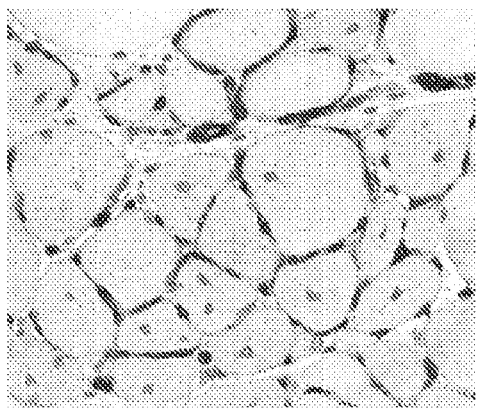

Mice were sacrificed at the end of the 30 day treatment period and the diaphragm and tibialis anterior muscles were collected and sectioned to determine if the anti-Flt-1 antibody induced angiogenesis in skeletal muscle. Sections of muscle were stained for the endothelial cell marker CD31. A significant increase in capillary density in the diaphragm muscles of mice treated with antibody 21B3 was seen as compared to the capillary density in the diaphragm muscles of mice treated with the isotype control antibody (FIGS. 17A-17E). The data were quantified using automated quantitative imaging software as shown in FIG. 18. There was a significant increase in the CD31 positive area in the diaphragm muscles of mice treated with 10 mg/kg or 20 mg/kg (p<0.0001) as compared to the CD31 positive area in the diaphragm muscles of mice treated isotype control antibody.

Figure 20:
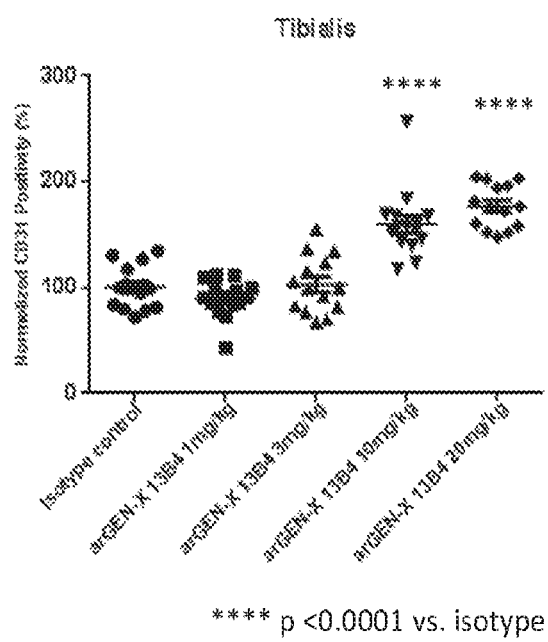
FIG. 20 shows exemplary results of quantification of the normalized CD31 positivity percentage in tissue sections obtained from the tibialis anterior muscle of mdx mice administered anti-Flt-1 antibody 21B3 or isotype control antibody.

A significant increase in the capillary density in the tibialis anterior muscle was also seen in the mice treated with antibody 21B3 as compared to the tibialis anterior muscle in mice treated with the isotype control antibody (FIGS. 19A-19E). The data were quantified using automated quantitative imaging software as shown in FIG. 20. There was a significant increase in the CD31 positive area in the tibialis anterior muscle of mice treated with 10 mg/kg or 20 mg/kg (p<0.0001) as compared to the CD31 positive area in the tibialis anterior muscle of mice treated with isotype control antibody.

RP-LC/MS Characterization

Figure 21A:
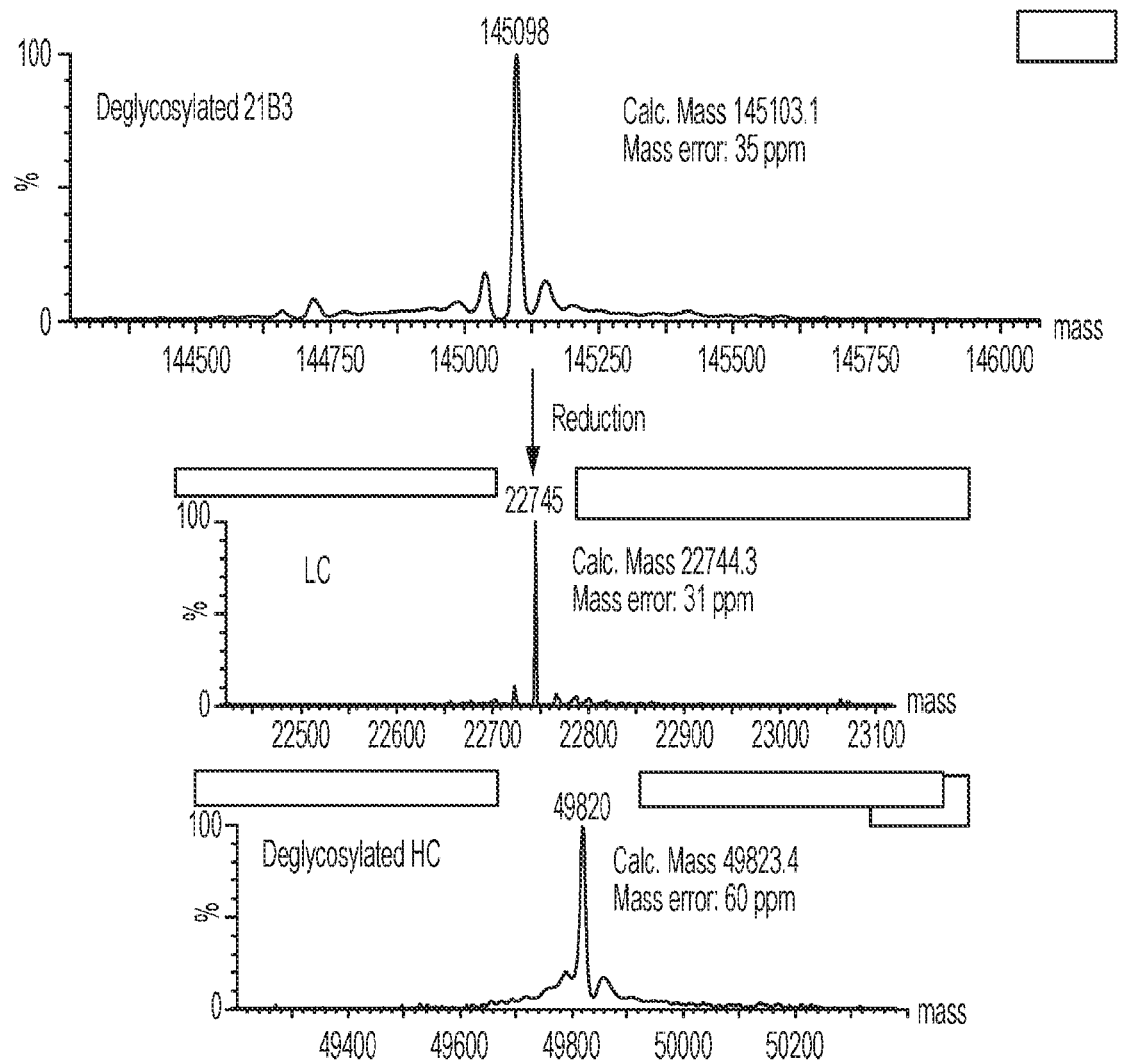
FIG. 21A shows exemplary results of reverse phase liquid chromatography/mass spectrometry (RP-LC/MS) analysis to determine the molecular weight of the deglycosylated 21B3 antibody.
Figure 21B:
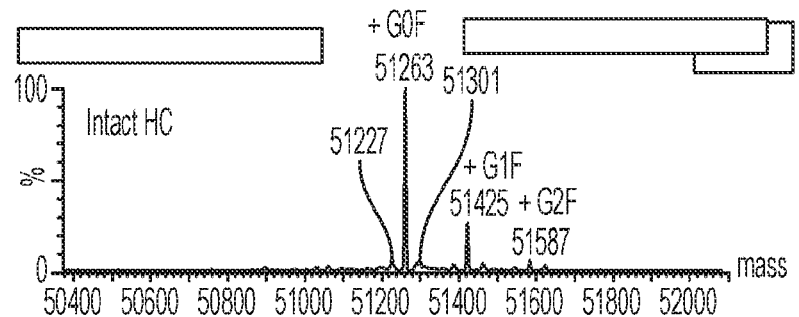
FIG. 21B shows exemplary results of analysis of the glycosylation pattern of the heavy chain.

The molecular weight of the deglycosylated 21B3 antibody was determined by reverse phase liquid chromatography/mass spectrometry (RP-LC/MS) (FIG. 21A). Following a reduction reaction, the molecular weight of the light chain and the heavy chain were determined. The glycosylation pattern of the heavy chain was also determined (FIG. 21B).

These results demonstrated that administration of an Flt-1 antibody (i.e., 21B3) to mdx mice resulted in a significant increase in endothelial cell proliferation as well as a decrease in soluble Flt-1 in serum and an increase in VEGF concentrations in serum.

Example 5. Characterization of Humanized High Affinity Anti-Flt-1 Antibodies

Light chain shuffled antibodies described in Example 3 were further modified to introduce sequence variation in the CDR regions and or Fc effector regions. These antibodies were evaluated by a surface plasmon resonance methodology (e.g., Biacore) to determine the binding characteristics (Table 9). Antibody 27H9 NG/NA AAA demonstrated an approximately 2 fold reduced binding affinity for Flt-1.

TABLE 9

|  | ka (1/Ms) | kd (1/s) | Rmax (RU) | KD (M) | Chi$^2$ | EXP |
|---|---|---|---|---|---|---|
| 21B3 WT | 5.4E+05 | 1.7E-04 | 292 | 3.2E-10 | 290 | 2 |
| 21B3 AAA | 5.2E+05 | 1.1E-04 | 305 | 2.1E-10 | 371 | 2 |
| 27H9 old 07/05 | 3.5E+05 | 7.9E-05 | 306 | 2.3E-10 | 235 | 1 |
| 27H9 WT 23/07 | 3.3E+05 | 8.4E-05 | 323 | 2.6E-10 | 236 | 1 |
| 27H9 NG/QG | 3.7E+05 | 1.3E-04 | 315 | 3.6E-10 | 280 | 1 |
| 27H9 NG/NA | 2.9E+05 | 1.1E-04 | 298 | 3.9E-10 | 158 | 1 |
| 27H9 NG/NA | 2.9E+05 | 1.5E-04 | 240 | 5.1E-10 | 96.4 | 2 |
| 27H9 NG/NA AAA | 2.9E+05 | 1.5E-04 | 236 | 5.1E-10 | 72.5 | 2 |

Figure 22A:
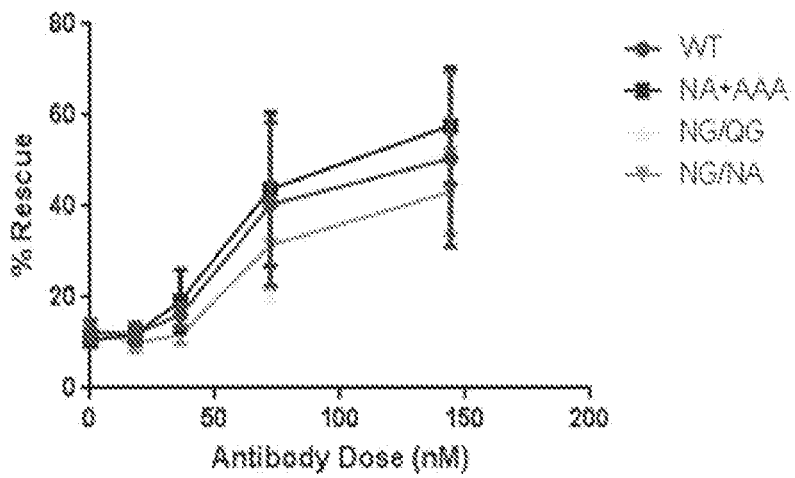
FIGS. 22A and 22B show exemplary results depicting rescue of phosphorylation of VEGF R2 by anti-Flt-1 antibodies. Human primary vein endothelial cells (HUVECs) were treated with VEGF in the presence of sFlt-1 and anti-Flt-1 antibodies and the level of VEGF R2 phosphorylation was determined. Percent rescue indicates the level of phosphorylation of VEGF R2 relative to the level of phosphorylation of VEGF R2 when HUVECs were treated with VEGF and sFlt-1 alone (i.e., no anti-Flt-1 antibody).

The antibodies were also evaluated in the cell based assay for ability to rescue cell activation by antagonizing sFlt-1. Human primary vein endothelial cells (HUVECs) were stimulated with VEGF in the presence of sFlt-1 and the monoclonal antibodies. VEGF induced activation of cells was assayed by determining the phosphorylation status of the VEGF R2 receptor. The monoclonal antibodies rescued cell activation (i.e., phosphorylation) by antagonizing soluble Flt-1 (FIG. 22A) and antibody 27H9 NG/NA AAA (NA+AAA) had similar potency as compared to the non-mutated parent antibody (wt).

Example 6. Antibody Optimization

Candidate antibodies were analyzed to identify the closest human VH and VL germline sequences and to identify differing residues within the framework regions and oxidation/isomerization sites within the CDRs. A Fab library containing human and wild-type residues was constructed and fused to human constant domains. Phage display was applied to identify Fabs with identical or better off rate (i.e., no loss of affinity) than the parent antibody, 21B3. Fabs with the desired off-rate were sequenced and compared to human germline sequence and those with the highest identity (e.g., VH+VL identity >95%) and homology (e.g., >96% homology) were selected for conversion into human monoclonal antibodies. The Fabs are also analyzed for unwanted amino acids. Table 10 provides Fabs ranked by percent human identity with some clones having up to 97.6% human identity and 98.8% homology.

TABLE 10

SORTED BY IDENTITY

| FAB IDENTITY | | | kd IMPROVE- | |
|---|---|---|---|---|
| | % Ident | % Homol | MENT | Kd |
| 27H4_VH | 97.6% | 98.8% | 1.06 | 5.1E-04 |
| 27H9_VH | 97.5% | 98.2% | 1.12 | 4.8E-04 |
| 25F11_VH | 97.5% | 98.2% | 1.00 | 5.3E-04 |
| 27H6_VH | 97.5% | 97.5% | 0.96 | 5.6E-04 |
| 25A2_VH | 97.0% | 98.8% | 0.97 | 5.5E-04 |
| 27D3_VH | 97.0% | 98.2% | 0.89 | 6.0E-04 |
| 27B4_VH | 97.0% | 98.2% | 0.84 | 6.4E-04 |
| 25D4_VH | 97.0% | 98.8% | 0.94 | 5.7E-04 |
| 25D6_VH | 97.0% | 98.2% | 1.17 | 4.6E-04 |
| 25G9_VH | 97.0% | 98.2% | 0.97 | 5.5E-04 |
| 27C5_VH | 97.0% | 98.2% | 0.96 | 5.5E-04 |
| 25D11_VH | 97.0% | 98.2% | 0.90 | 6.0E-04 |
| 25C8_VH | 97.0% | 97.5% | 0.84 | 6.3E-04 |
| 25G2_VH | 96.9% | 98.2% | 0.81 | 6.6E-04 |
| 27A1_VH | 96.4% | 98.2% | 0.97 | 5.5E-04 |
| 25H3_VH | 96.4% | 97.5% | 0.94 | 5.7E-04 |
| 27F5_VH | 96.3% | 98.2% | 1.18 | 4.5E-04 |
| 25B9_VH | 96.3% | 98.2% | 1.03 | 5.2E-04 |
| 27H1_VH | 96.3% | 98.2% | 0.91 | 5.9E-04 |
| 27G9_VH | 96.3% | 97.5% | 1.30 | 4.1E-04 |
| 27D9_VH | 96.3% | 97.5% | 0.94 | 5.7E-04 |
| 25G8_VH | 96.3% | 97.5% | 0.82 | 6.5E-04 |
| 21B3 | 96.3% | 96.3% |  | 5.3E-04 |

Example 7. Characterization of Anti-Flt-1 Monoclonal Antibodies

The thermo-tolerance of the monoclonal antibodies was analyzed using a Biacore method. At a concentration of 100 μg/mL, each monoclonal antibody was incubated for 1 hour in phosphate buffered saline at different temperatures. Following the 1 hour incubation, the antibody was slowly cooled to 25° C. over two hours then incubated overnight at 4° C. The percentage of functional antibody was then measured by determining the binding to human Flt-1 by Biocore (see Table 11). The thermo-tolerance for the wild-type antibodies was consistent with previous experiments. However, with the exception of the 27H6 DG/DA clone, mutations in the VH or VL regions reduced the melting temperature by approximately 2° C. The AAA mutation in the Fc region had no effect on the thermo-tolerance of the antibody.

TABLE 11

| | Tm (° C.) | | | | | |
|---|---|---|---|---|---|---|
| MAB | Exp 140421 | Exp 140507 | Exp 140514 | Exp 140613 | Exp 140723 | Exp 140902 |
| 21B3 WT | 70.1 | 70.4 | 70.9 | 69.1 | | 70.5 |
| 21B3 AAA | | | | | | ~70.8 |
| 27H4 WT | 67 | 67.8 | | ~66.6 | 67.5 | |
| 27H4 NG/NA (VH) | | | | | ~64.1 | |

TABLE 11-continued

| | Tm (° C.) | | | | | |
|---|---|---|---|---|---|---|
| MAB | Exp 140421 | Exp 140507 | Exp 140514 | Exp 140613 | Exp 140723 | Exp 140902 |
| 27H4 NG/QG (VH) | | | | | ~64.1 | |
| 27H4 NA + AAA | | | | | | 64.9 |
| 27H6 WT | | | | | 61.9 | |
| 27H6 DG/DA (VL) | | | | | ~63.4 | |
| 27H6 DG/EG (VL) | | | | | 58.8 | |
| 27H9 WT | | | 73.8 | 68.6 | 69.0 | |
| 27H9 NG/NA (VH) | | | | | 66.8 | |
| 27H9 NG/QG (VH) | | | | | 66.7 | |
| 27H9 NA + AAA | | | | | | 67.3 |

Figure 22B:
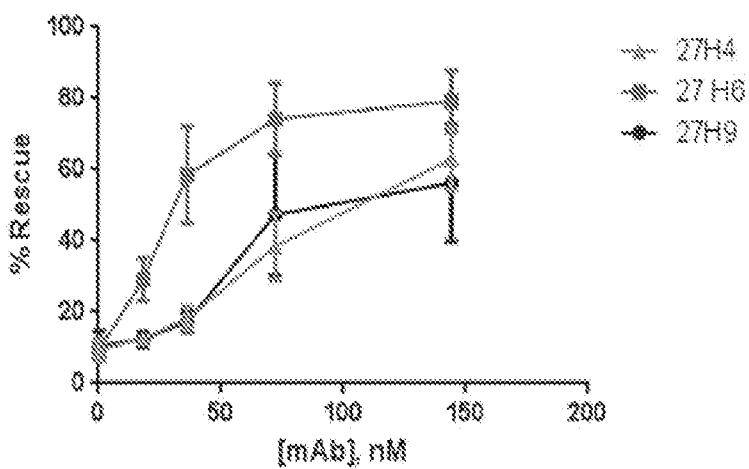
Figure 23:
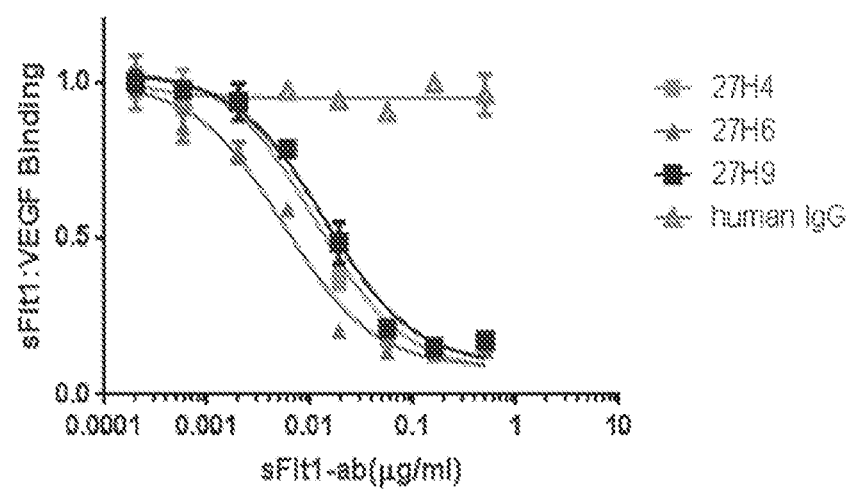
FIG. 23 shows exemplary results depicting binding of anti-Flt-1 antibodies to recombinant sFlt-1 by an ELISA assay.

The binding affinity of the humanized clones were analyzed by Biacore (Table 12). The ability to rescue VEGF signaling in a VEGF:sFlt-1 cell based assay was determined for antibodies 27H4, 27H6 and 27H9 (FIG. 22B). Briefly, human primary vein endothelial cells (HUVECs) were stimulated with VEGF in the presence of sFlt-1 and monoclonal antibodies 27H4, 27H6 and 27H9. VEGF induced activation of cells was assayed by determining the phosphorylation status of the VEGF R2 receptor. The data are expressed as a percent rescue of the phosphorylation of the VEGF R2 receptor relative to the phosphorylation of the VEGF R2 receptor in the presence of sFlt-1 alone (e.g., without anti-Flt-1 antibodies). The ability to antagonize binding of VEGF and sFlt-1 (FIG. 23) was also determined for antibodies 27H4, 27H6 and 27H9 by ELISA.

TABLE 12

| | ka (1/Ms) | kd (1/s) | Rmax (RU) | KD (M) |
|---|---|---|---|---|
| 21B3 | 5.4E+05 | 1.7E-04 | 292 | 3.2E-10 |
| 27H4 | 3.4E+05 | 8.2E-05 | 305 | 2.5E-10 |
| 27H9 | 3.3E+05 | 8.4E-05 | 323 | 2.6E-10 |
| 27H6 | 9.1E+05 | 1.4E-04 | 436 | 1.6E-10 |

Example 8. In Vitro Study of Anti-Flt-1 Antibodies on Muscle Pathology

Mdx mice were treated with 1, 3 or 10 mg/kg of anti-Flt-1 antibody 21B3 or 10 mg/kg of IgG1 isotype control antibody by intravenous administration twice a week for 6 or 12 weeks beginning at 3 weeks of age.

Figure 24:
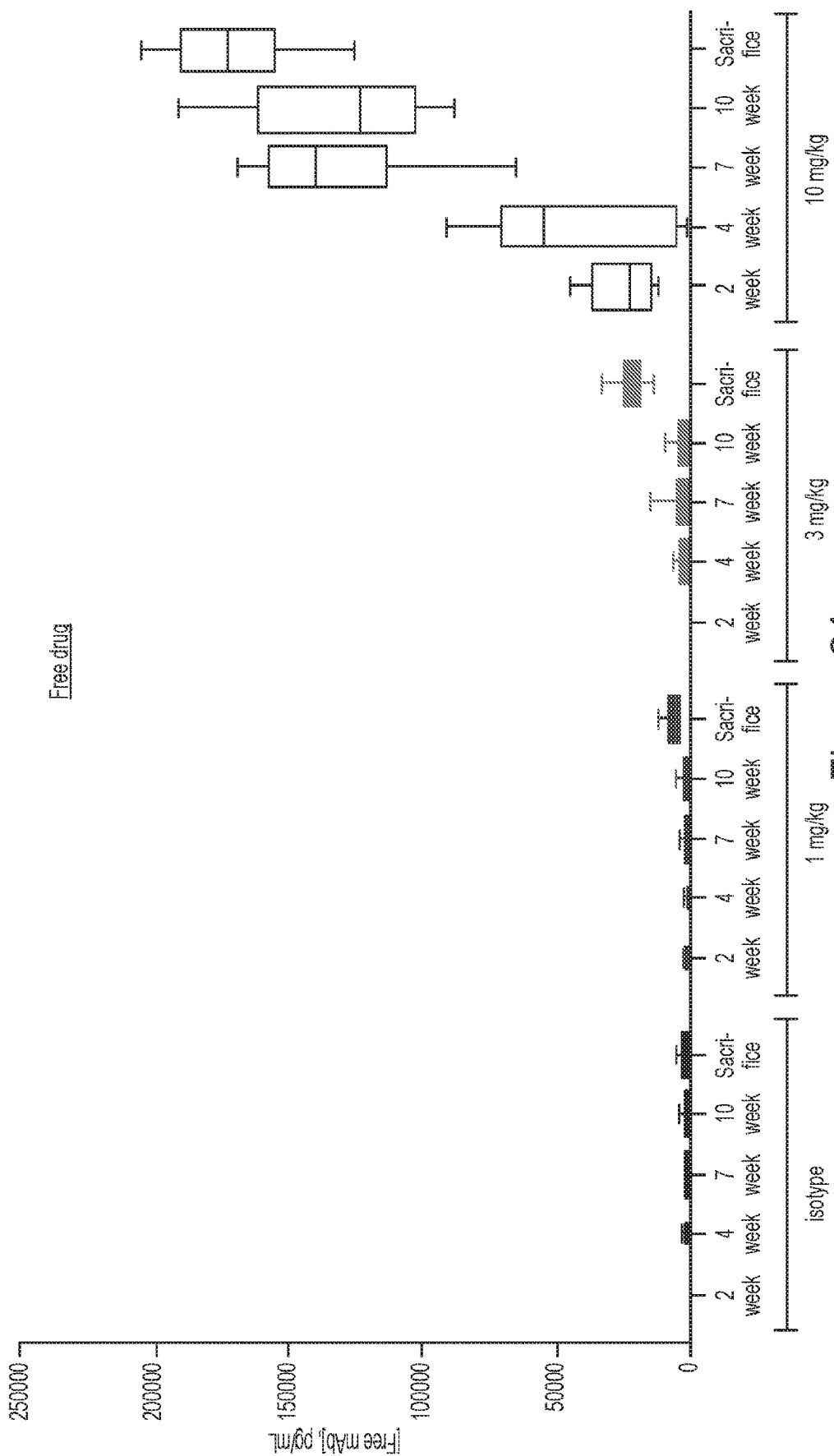
FIG. 24 shows exemplary results depicting serum levels of free anti-Flt-1 antibody 21B3 and isotype control antibody in mdx mice.

To assess serum levels of free antibody concentration, blood was collected from the mice 4 days after the intravenous dose administered at 2, 4, 7 and 10 weeks. The sacrifice sample was collected 24 hours after the last dose (FIG. 24). At the 10 mg/kg dose, there was a statistically significant difference in serum levels of free antibody at all time points relative to the serum levels of free antibody in mice receiving the isotype control antibody. At the 3 mg/kg dose, there was a statistically significant difference in serum levels of free antibody at weeks 4, 7 and 10 and at sacrifice relative to the serum levels of free antibody in mice receiving the isotype control antibody. At the 1 mg/kg dose, there was a statistically significant difference in serum levels of free antibody at sacrifice relative to the serum levels of free antibody in mice receiving the isotype control antibody.

Figure 25:
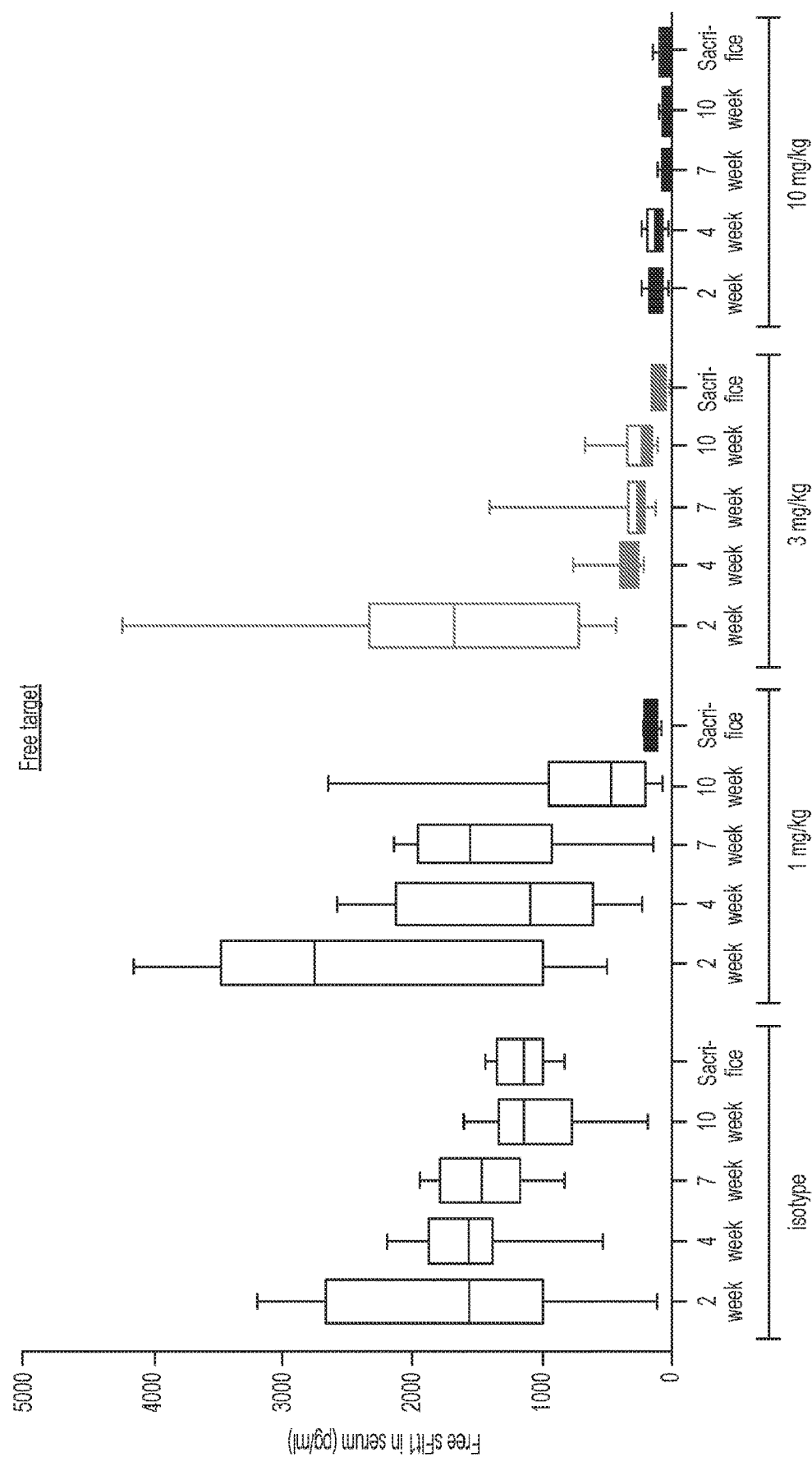
FIG. 25 shows exemplary results depicting serum levels of free sFlt-1 in mdx mice treated with either anti-Flt-1 antibody 21B3 or isotype control antibody.

To assess serum levels of free sFlt-1, blood was collected from the mice 4 days after the intravenous dose administered at 2, 4, 7 and 10 weeks. The sacrifice sample was collected 24 hours after the last dose (FIG. 25). At the 10 mg/kg dose, there was a statistically significant difference in serum levels of free sFlt-1 at all time points relative to the serum levels of free sFlt-1 in mice receiving the isotype control antibody. At the 3 mg/kg dose, there was a statistically significant difference in serum levels of free sFlt-1 at weeks 4, 7 and 10 and at sacrifice relative to the serum levels of free sFlt-1 in mice receiving the isotype control antibody. At the 1 mg/kg dose, there was a statistically significant difference in serum levels of free sFlt-1 at sacrifice relative to the serum levels of free sFlt-1 in mice receiving the isotype control antibody.

Figure 26:
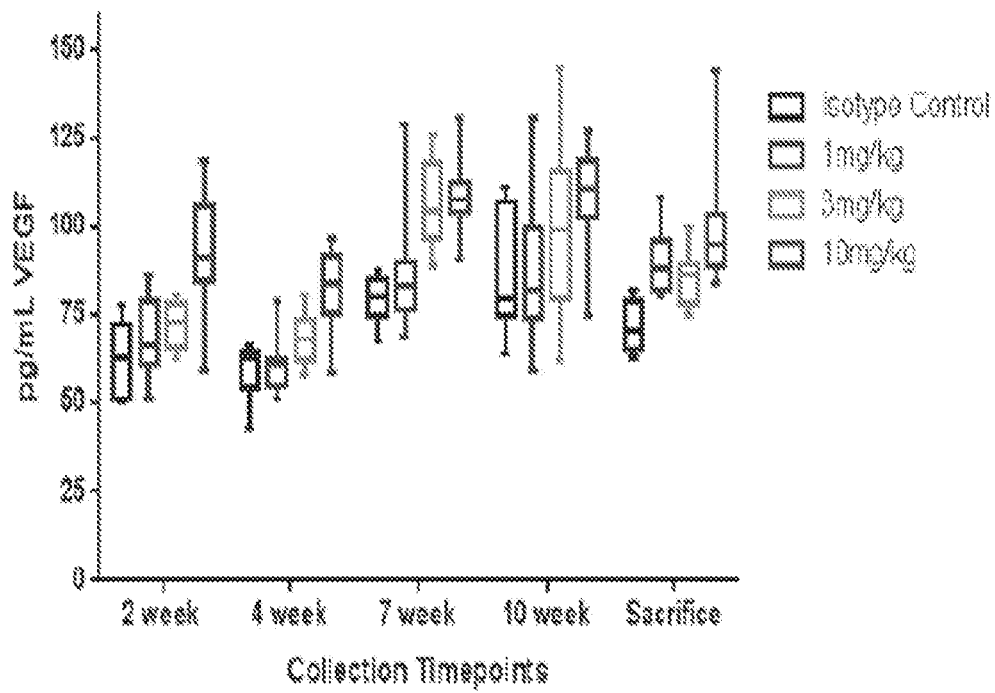
FIG. 26 shows exemplary results depicting serum levels of VEGF in mdx mice treated with either anti-Flt-1 antibody 21B3 or isotype control antibody.
Figures 27A, 27B, 27C, 27D:
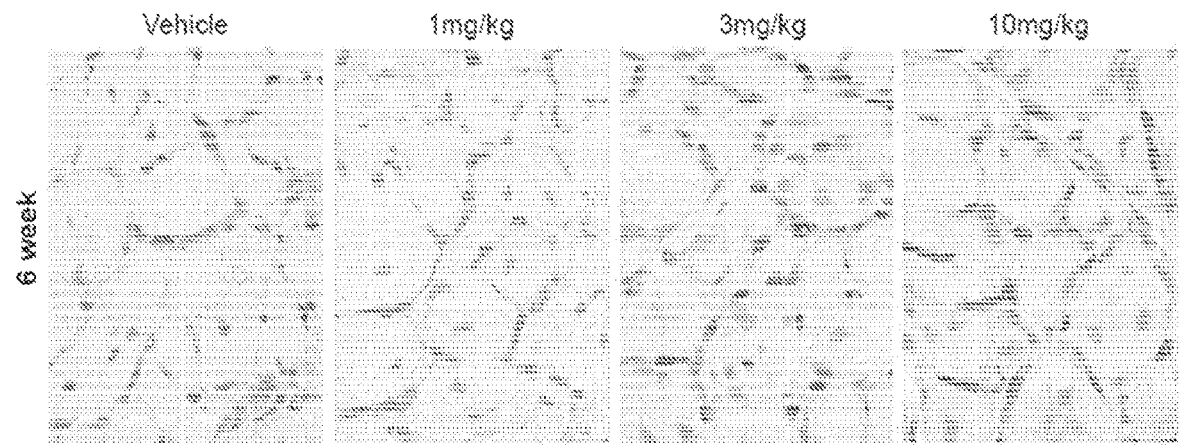
FIGS. 27A-27H show exemplary results of CD31 staining of tissue sections obtained from the diaphragm muscle of mdx mice anti-Flt-1 antibody 21B3 or vehicle control for 6 (27A-27D) or 12 (27E-27H) weeks.
Figures 27E, 27F, 27G, 27H:
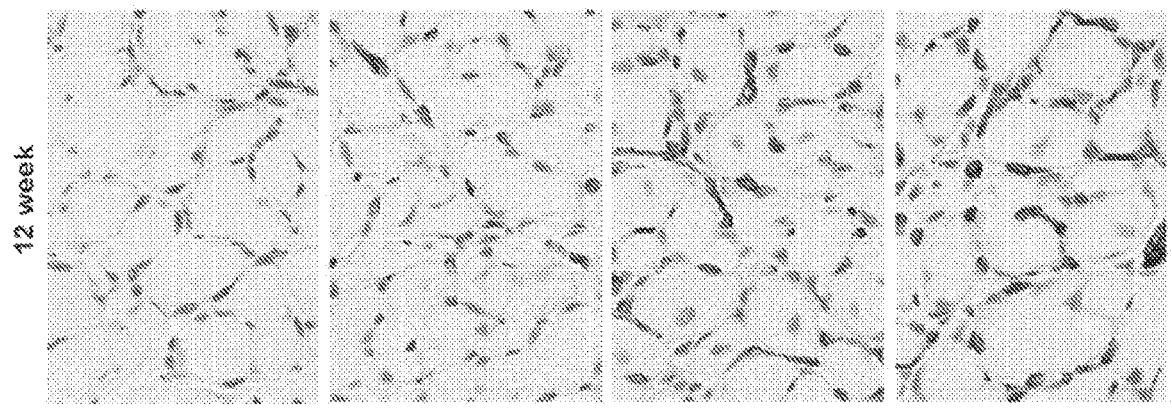
Figures 28A, 28B, 28C, 28D:
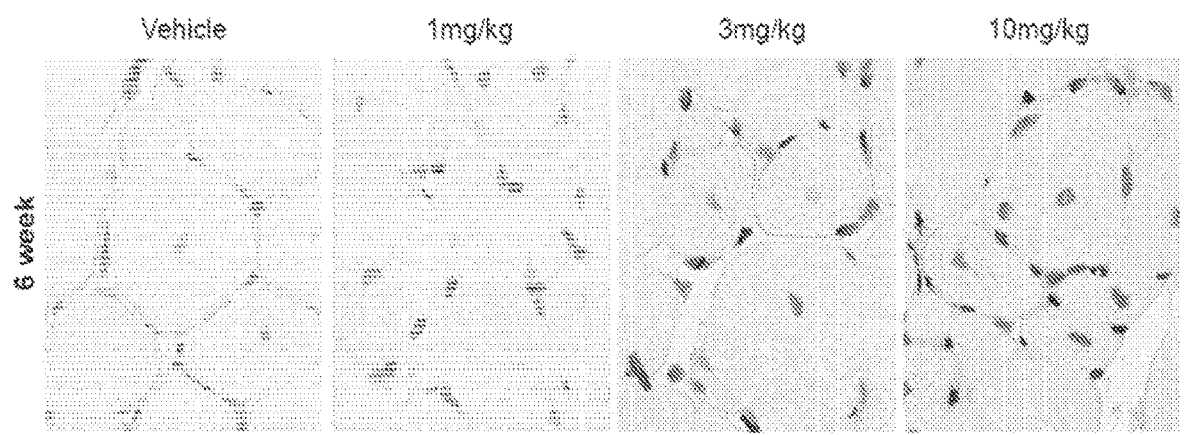
FIGS. 28A-28H show exemplary results of CD31 staining of tissue sections obtained from the gastrocnemius muscle of mdx mice administered anti-Flt-1 antibody 21B3 or vehicle control for 6 weeks (28A-28D) or 12 weeks (28E-28H).
Figures 28E, 28F, 28G, 28H:
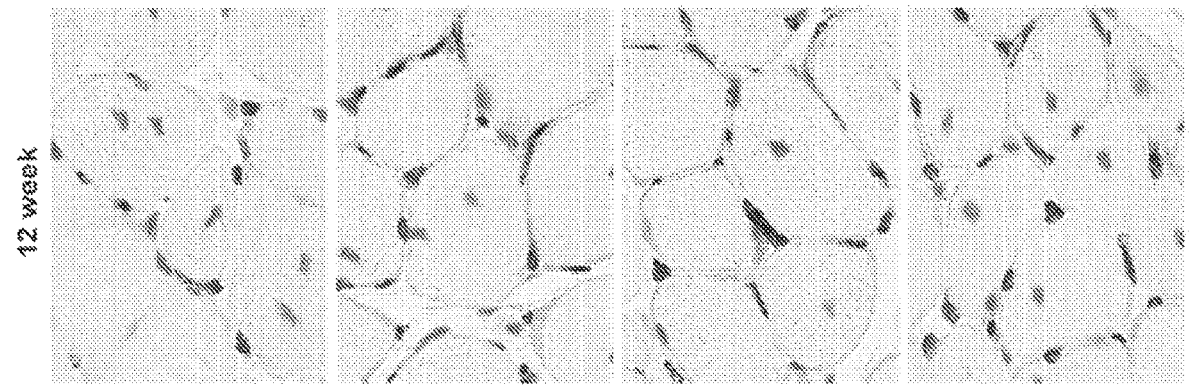
Figures 29A, 29B, 29C, 29D:
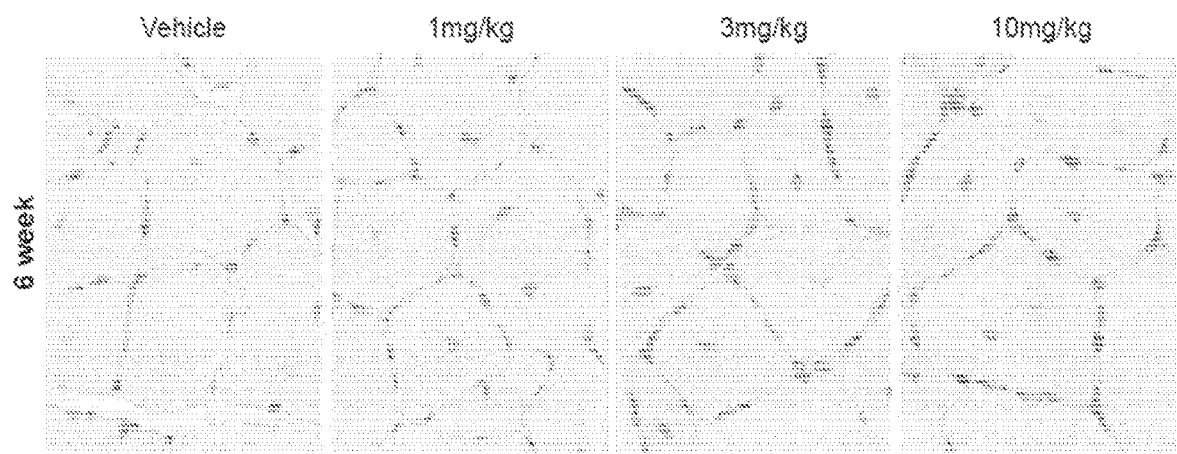
FIGS. 29A-29H show exemplary results of CD31 staining of tissue sections obtained from the tibialis muscle of mdx mice administered anti-Flt-1 antibody 21B3 or vehicle control for 6 weeks (29A-29D) or 12 weeks (29E-29H).
Figures 29E, 29F, 29G, 29H:
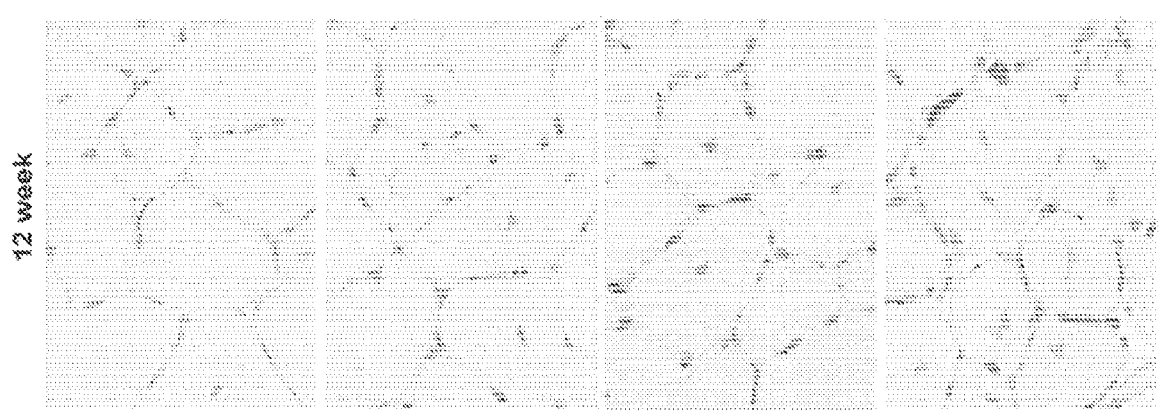

To assess serum levels of VEGF, blood was collected from the mice 4 days after the intravenous dose administered at 2, 4, 7 and 10 weeks. The sacrifice sample was collected 24 hours after the last dose (FIG. 26). Administration of antibody 21B3 induced a dose dependent increase in serum VEGF levels. At the 10 mg/kg dose, there was a statistically significant difference in serum levels of VEGF at all time points relative to the serum levels of VEGF in mice receiving the isotype control antibody. At the 3 mg/kg dose, there was a statistically significant difference in serum levels of VEGF at week 7 and at sacrifice relative to the serum levels of VEGF in mice receiving the isotype control antibody. At the 1 mg/kg dose, there was a statistically significant difference in serum levels of VEGF at sacrifice relative to the serum levels of VEGF in mice receiving the isotype control antibody.

Histopathology

Mice were sacrificed at weeks 6 and 12 of the treatment period and the diaphragm, gastrocnemius and tibialis anterior muscles were collected and sectioned to determine if treatment with the anti-Flt-1 antibody induced angiogenesis and prevented fibrosis and necrosis in skeletal muscle.

Angiogenesis

Figure 30A:
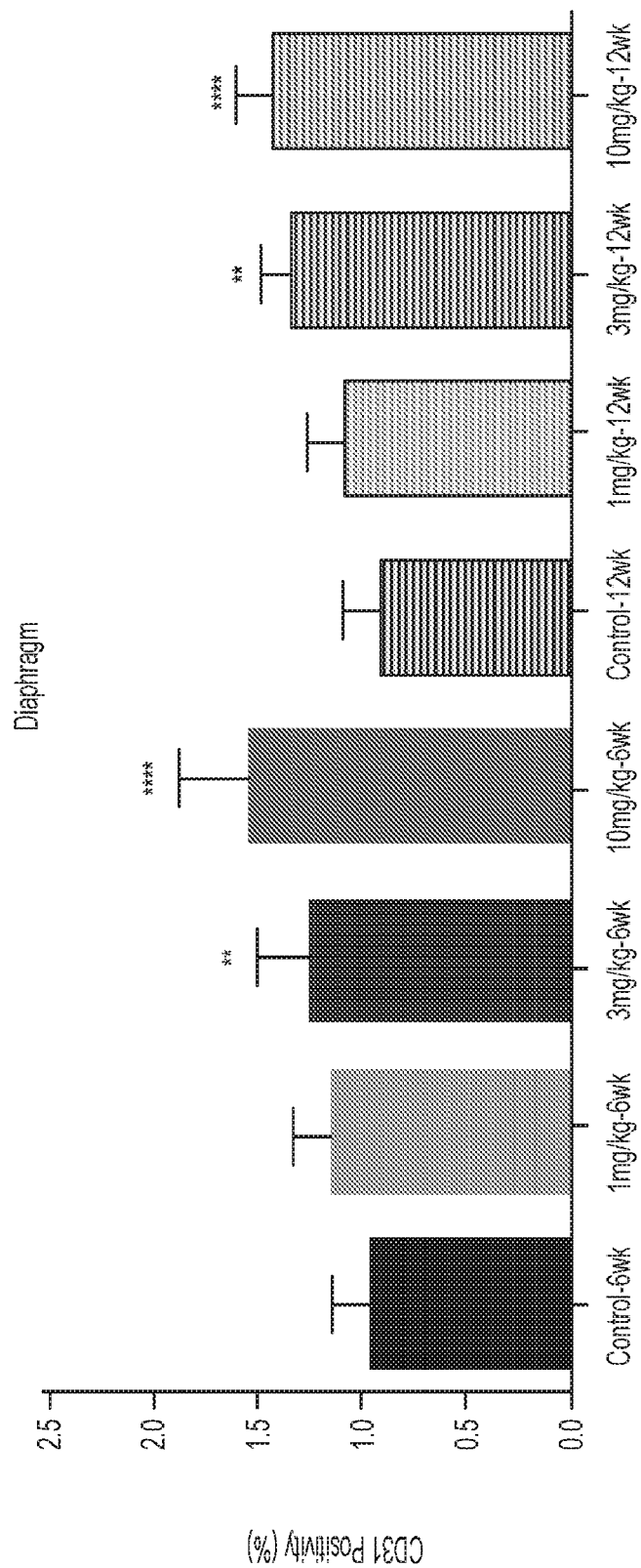
Figure 30B:
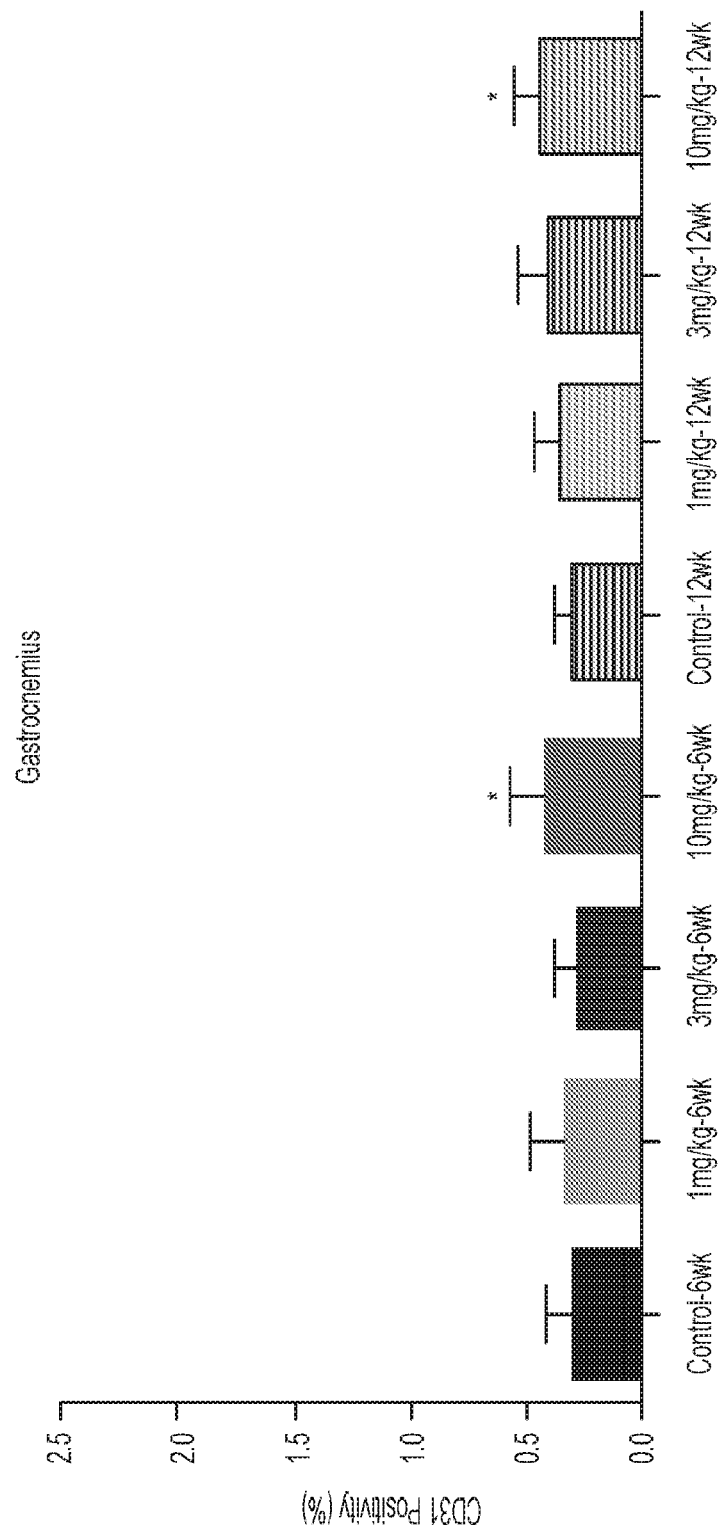
Figures 31A, 31B, 31C, 31D:
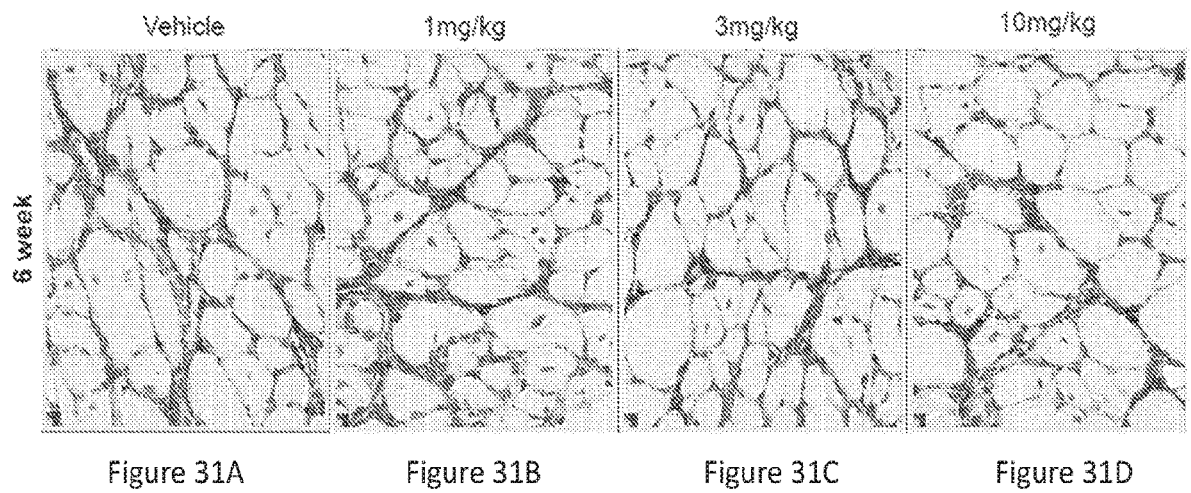
FIGS. 31A-31H show exemplary results of collagen type I immunohistochemical staining of tissue sections obtained from the diaphragm muscle of mdx mice administered anti-Flt-1 antibody 21B3 or vehicle control for 6 weeks (31A-31D) or 12 weeks (31E-31H).
Figures 31E, 31F, 31G, 31H:
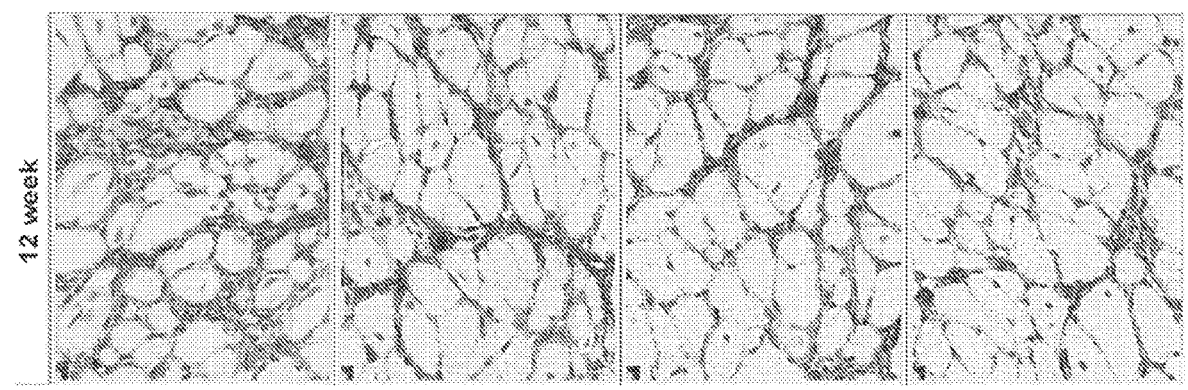
Figures 32A, 32B, 32C, 32D:
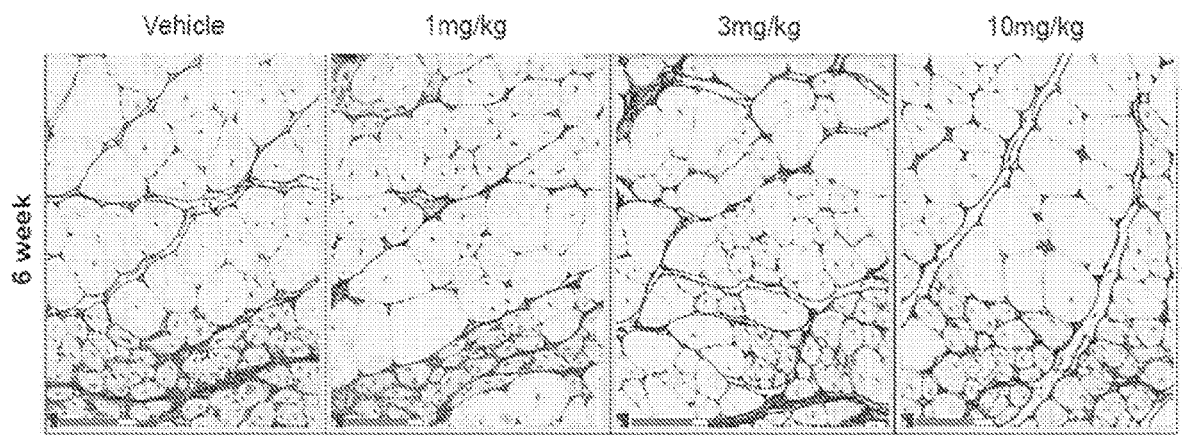
FIGS. 32A-32H show exemplary results of collagen type I immunohistochemical staining of tissue sections obtained from the gastrocnemius muscle of mdx mice administered anti-Flt-1 antibody 21B3 or vehicle control for 6 weeks (32A-32D) or 12 weeks (32E-32H).
Figures 32E, 32F, 32G, 32H:
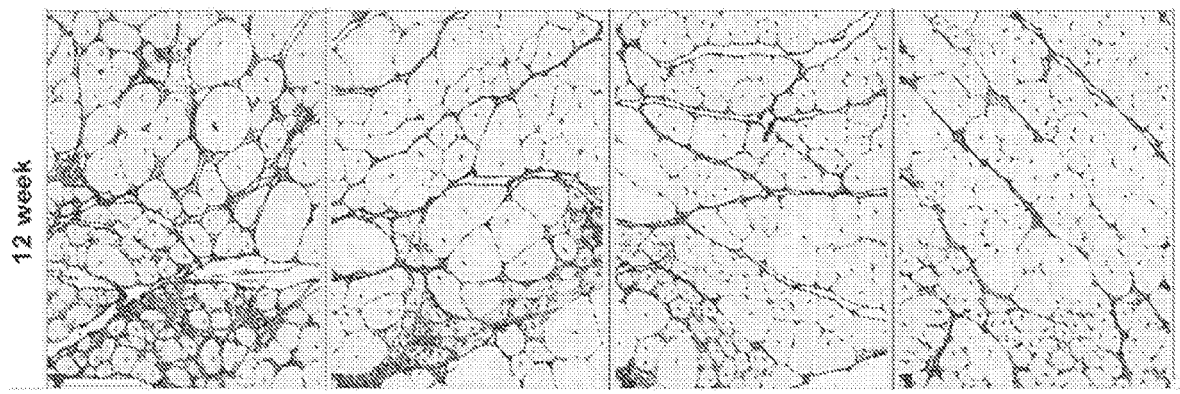
Figures 33A, 33B, 33C, 33D:
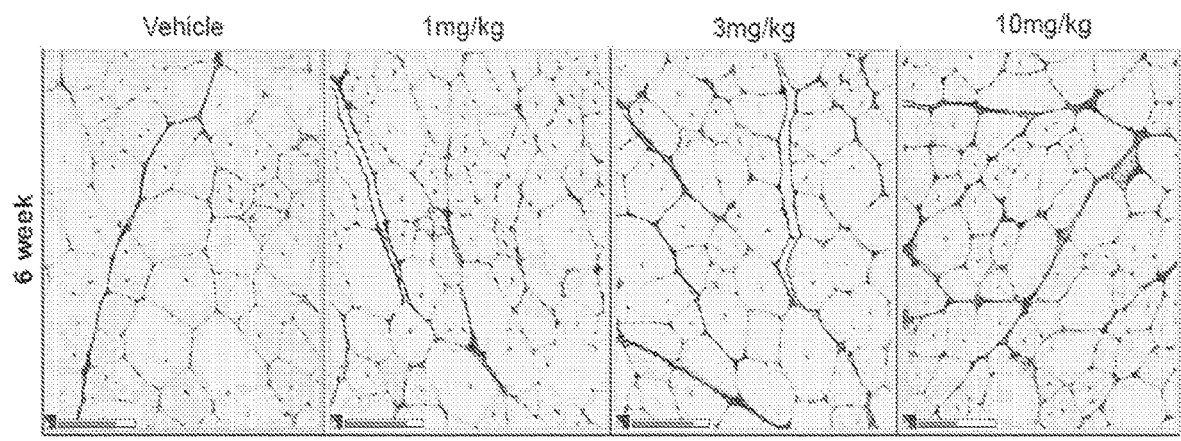
FIGS. 33A-33H show exemplary results of collagen type I immunohistochemical staining of tissue sections obtained from the tibialis muscle of mdx mice administered anti-Flt-1 antibody 21B3 or vehicle control for 6 weeks (33A-33D) or 12 weeks (33E-33H).
Figures 33E, 33F, 33G, 33H:
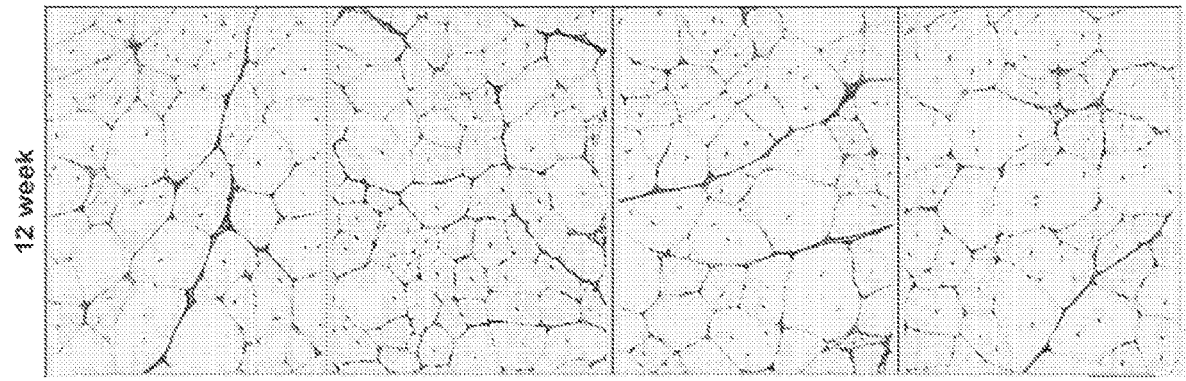

Sections of muscle were stained for the endothelial cell marker CD31 (FIGS. 27A-27H, 28A-28H and 29A-29H). A significant increase in capillary density was seen in all muscle groups studied in the mice treated with antibody 21B3 as compared to the muscles of mice treated with the isotype control antibody. The data were quantified using automated quantitative imaging software. There was a statistically significant increase in the CD31 positive area in the diaphragm muscle of mice treated with 3 mg/kg (p<0.01) and 10 mg/kg (p<0.0001) of antibody 21B3 at 6 and 12 weeks as compared to the CD31 positive area in the diaphragm muscle of mice treated with the isotype control antibody. There was a statistically significant increase in the CD31 positive area in the gastrocnemius muscle of mice treated with 10 mg/kg (p<0.05) of antibody 21B3 at 6 and 12 weeks as compared to the CD31 positive area in the gastrocnemius muscle of mice treated with isotype control antibody. There was a statistically significant increase in the CD31 positive area in the tibialis anterior muscle of mice treated with 3 mg/kg of antibody 21B3 at 6 weeks (p<0.05) and 12 weeks (p<0.0001) and of mice treated with 10 mg/kg (p<0.0001) of antibody 21B3 at 6 and 12 weeks as compared to the CD31 positive area in the tibialis anterior muscle of mice treated with the isotype control antibody. (FIGS. 30A-30C).

Fibrosis

Figure 34A:
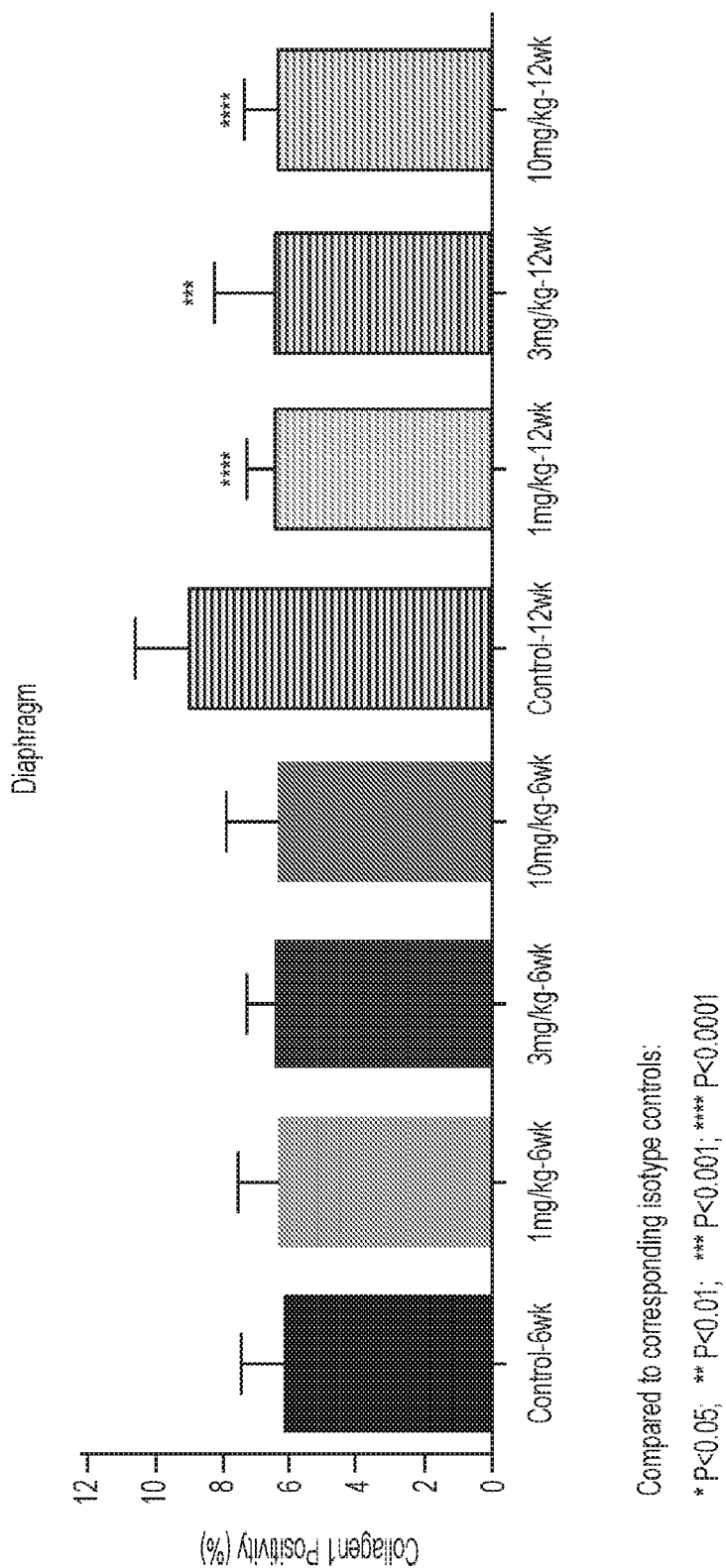
FIGS. 34A-34C show exemplary results of quantification of the percent positivity of collagen type I staining in tissue sections obtained from the diaphragm, gastrocnemius and tibialis muscle of mdx mice administered anti-Flt-1 antibody 21B3 or vehicle control antibody for 6 or 12 weeks.
Figure 34B:
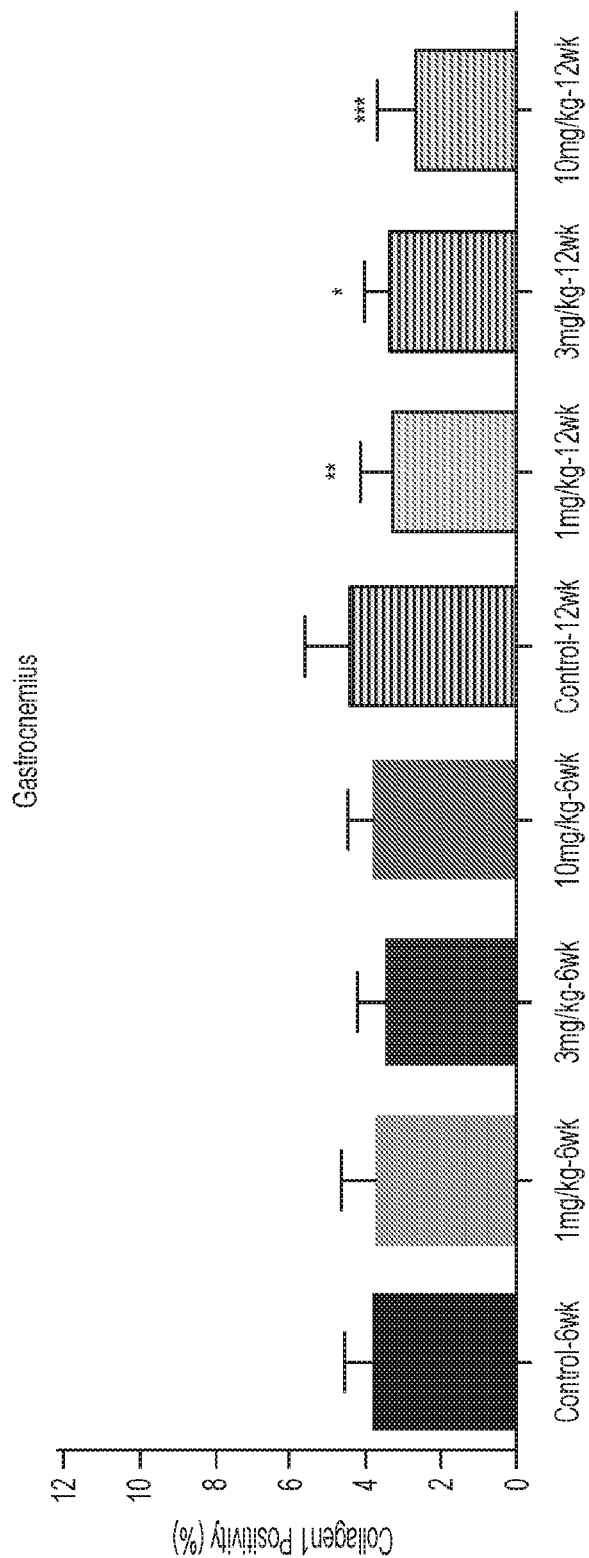
Figure 34C:
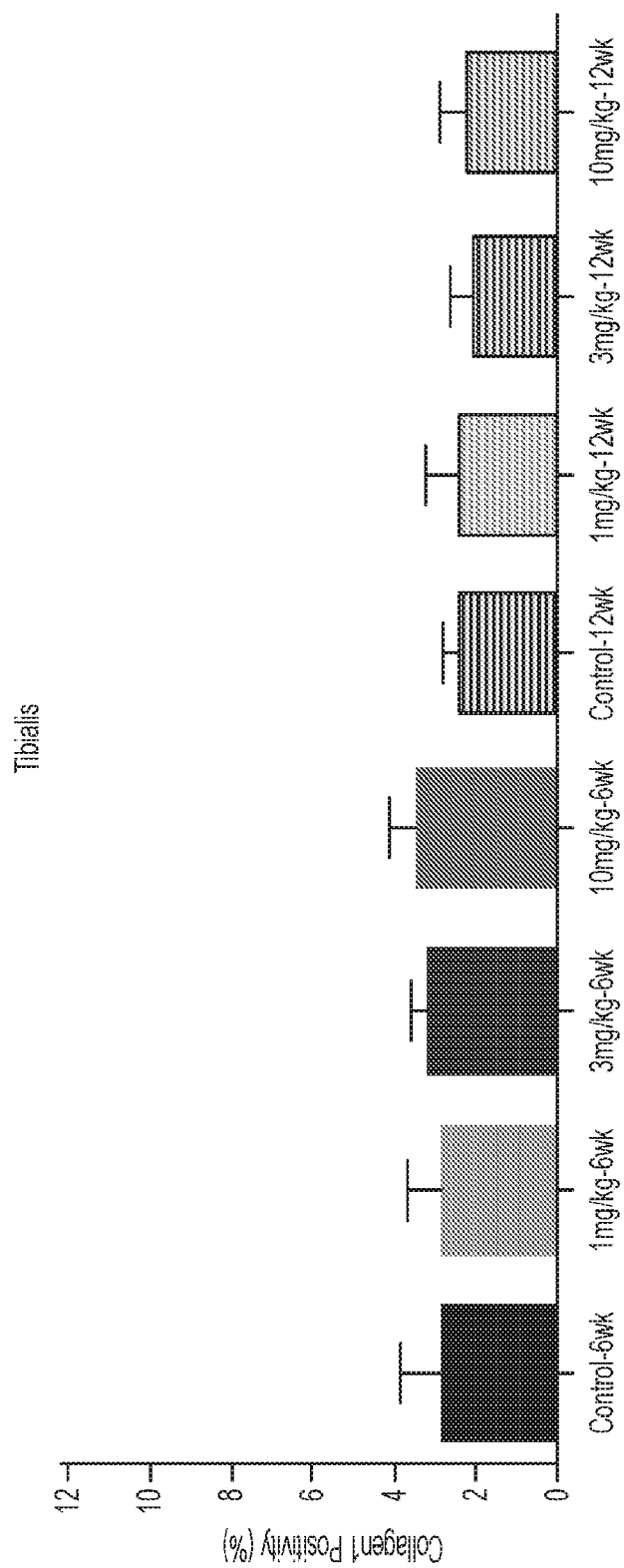

Sections of muscle were also stained by immunohistochemistry for type I collagen (FIGS. 31A-31H, 32A-32H and 33A-33H). A significant decrease in type I collagen staining was seen in the diaphragm and gastrocnemius muscle of mice treated with antibody 21B3 as compared to the diaphragm and gastrocnemius muscle of mice treated with the isotype control antibody. There was a statistically significant decrease in the type I collagen staining in the diaphragm muscle of mice treated with 1 mg/kg ($p<0.0001$), 3 mg/kg ($p<0.001$) and 10 mg/kg ($p<0.0001$) of antibody 21B3 at 12 weeks as compared to the type I collagen staining in the diaphragm muscle of mice treated with the isotype control antibody. There was a statistically significant decrease in type I collagen staining in the gastrocnemius muscle of mice treated with 1 mg/kg ($p<0.01$), 3 mg/kg ($p<0.05$) and 10 mg/kg ($p<0.001$) of antibody 21B3 at 12 weeks as compared to the type I collagen staining in the gastrocnemius muscle of mice treated with the isotype control antibody. (FIGS. 34A-34C).

Necrosis

Figure 35A:
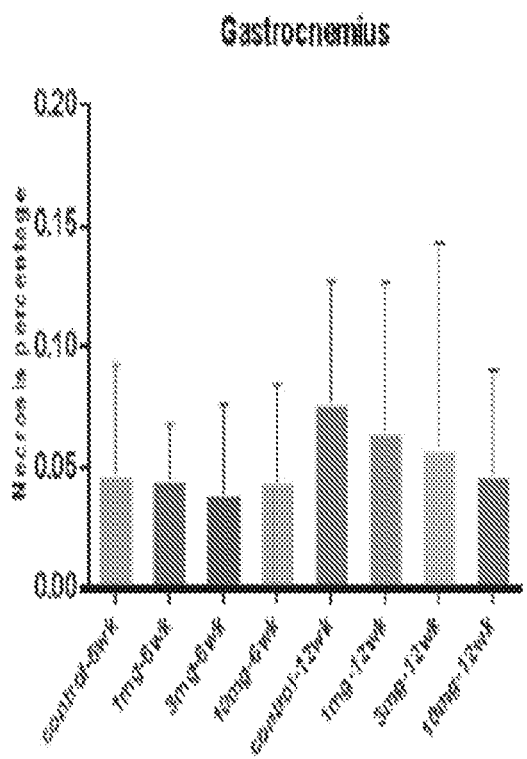
FIGS. 35A and 35B show exemplary results of quantification of the percent necrosis of gastrocnemius muscle of mdx mice administered anti-Flt-1 antibody 21B3 or vehicle control antibody for 6 or 12 weeks.
Figure 35B:
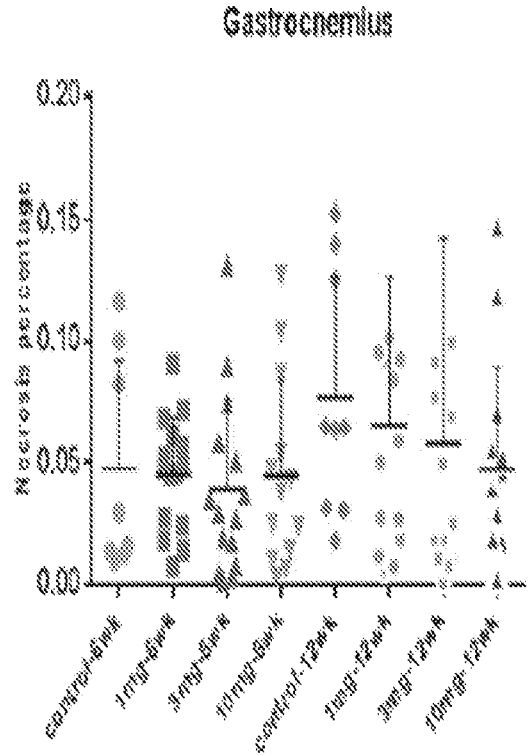

The percentage of necrosis present in the gastrocnemius muscle of mice treated with the 21B3 antibody was determined relative to the percentage of necrosis present in the gastrocnemius muscle of mice treated with the isotype control antibody. A trend toward improvement in necrosis was seen (FIGS. 35A-35B).

Example 9. Mapping of the Epitope on Human sFlt-1 Targeted by Anti-Flt-1 Antibodies 21B3 and 21C6

The peptide level epitopes on human sFlt-1 targeted by anti-human sFlt-1 monoclonal antibodies (mAbs) 21B3 and 21C6 were established by hydrogen deuterium exchange (HDX) mass spectrometry.

Pepsin Digestion and LC-MS

For pepsin digestion, 10 µg of sFlt-1 or sFlt-1 and antibody (21B3) mixture (10 µg:20 µg) or sFlt-1 and antibody (21C6) mixture (10 µg:20 µg) was denatured in 0.365 M TCEP and 1.7 M guanidine hydrochloride (pH 2.5). The mixture was subjected to online pepsin digestion and the resultant peptides were analyzed using an UPLC-MS system comprised of a Waters Acquity UPLC coupled to a Micro-TOF-Q2 mass spectrometer (Bruker). The peptides were separated on a 50 mm×1 mm C8 column with a 19 min gradient from 5-28.5% solvent B (0.1% formic acid in acetonitrile). Solvent A is 0.1% formic acid in water. The solvent mixture valve, injection valve, C8 column and all the connecting stainless steel tubings were immersed in a chilled circulating water bath maintained at 0° C. Peptide identification was done through searching MS/MS data against the sFlt-1 sequence with Mascot. The mass tolerance for the precursor and product ions was 0.1 Da and 0.2 Da, respectively.

Deglycosylation Treatment

200 µg of human sFlt-1 recombinant protein was incubated with 10 µl of PNGase F at 37° C. for 4 hrs.

Fab Preparation

Fabs were prepared from two anti-sFlt-1 mAbs (21B3 and 21C6) with papain digestion and Protein A capture using Pierce Fab Preparation Kit.

Size Exclusion Chromatography (SEC)

To check the binding between either native or deglycosylated human sFlt-1 and two anti-human sFlt-1 mAbs (21B3 and 21C6) on SEC, 10 µg of sFlt-1 (either native or deglycosylated) was mixed with 40 µg of anti-sFlt-1 mAbs. Native or deglycosylated sFlt-1 alone, anti-sFlt-1 mAb alone or the complexes were injected to a SEC column at flow rate of 0.35 ml/min with PBS as the mobile phase and the proteins were monitored at 280 nm. Fabs generated from anti-sFlt-1 mAbs (21B3 and 21C6), and the binding between anti-sFlt-1 Fabs and sFlt-1 were also assessed using SEC.

HDX

10 µL human sFlt-1 (10 µg) or sFlt-1 and mAb (21B3) mixture (10 µg:20 µg) or sFlt-1 and mAb (21C6) mixture (10 µg:20 µg) was incubated with 90 µL deuterium oxide labeling buffer (50 mM phosphate, 100 mM sodium chloride at pH 7.4) for 0 s, 30 s, 2 min, 10 min, 1 hr or 4 hr. Deuterium exchange was quenched by adding 100 µL of 3.4 M guanidine hydrochloride, 0.73 M TCEP buffer with a final pH of 2.5, and then subjected to pepsin digestion and LC-MS analysis described above. The mass spectra were recorded in MS only mode. Raw MS data was processed using HDExaminer software (Sierra Analytics, CA). The deuterium levels were calculated using the average mass difference between the deuterated peptide and its native form (to).

Results

To verify that glycan removal does not alter the binding of human sFlt-1 to the antibodies, native and deglycosylated sFlt-1 protein were mixed with the anti-human sFlt-1 IgGs (21B3 and 21C6) and the complex formation was monitored on size exclusion chromatography. The data demonstrated that native human sFlt-1 completely binds to the two anti-human sFlt-1 IgGs (21B3 and 21C6) while deglycosylated human sFlt-1 incompletely binds to anti-human sFlt-1 mAb (21B3) or does not bind to anti-human sFlt-1 mAb (21C6), which indicated that deglycosylation perturbs the interactions between human sFlt-1 and the antibodies. Therefore, native human sFlt-1 was selected to perform HD exchange experiments. Poor sequence coverage was achieved initially for native human sFlt-1 due to the high complexity of heterogeneous glycosylation and 12 N-linked glycosyltation sites. To improve the sequence coverage, glycan masses at each glycosylation site were identified and high sequence coverage (85.2%) was achieved for native human sFlt-1.

Figure 36:
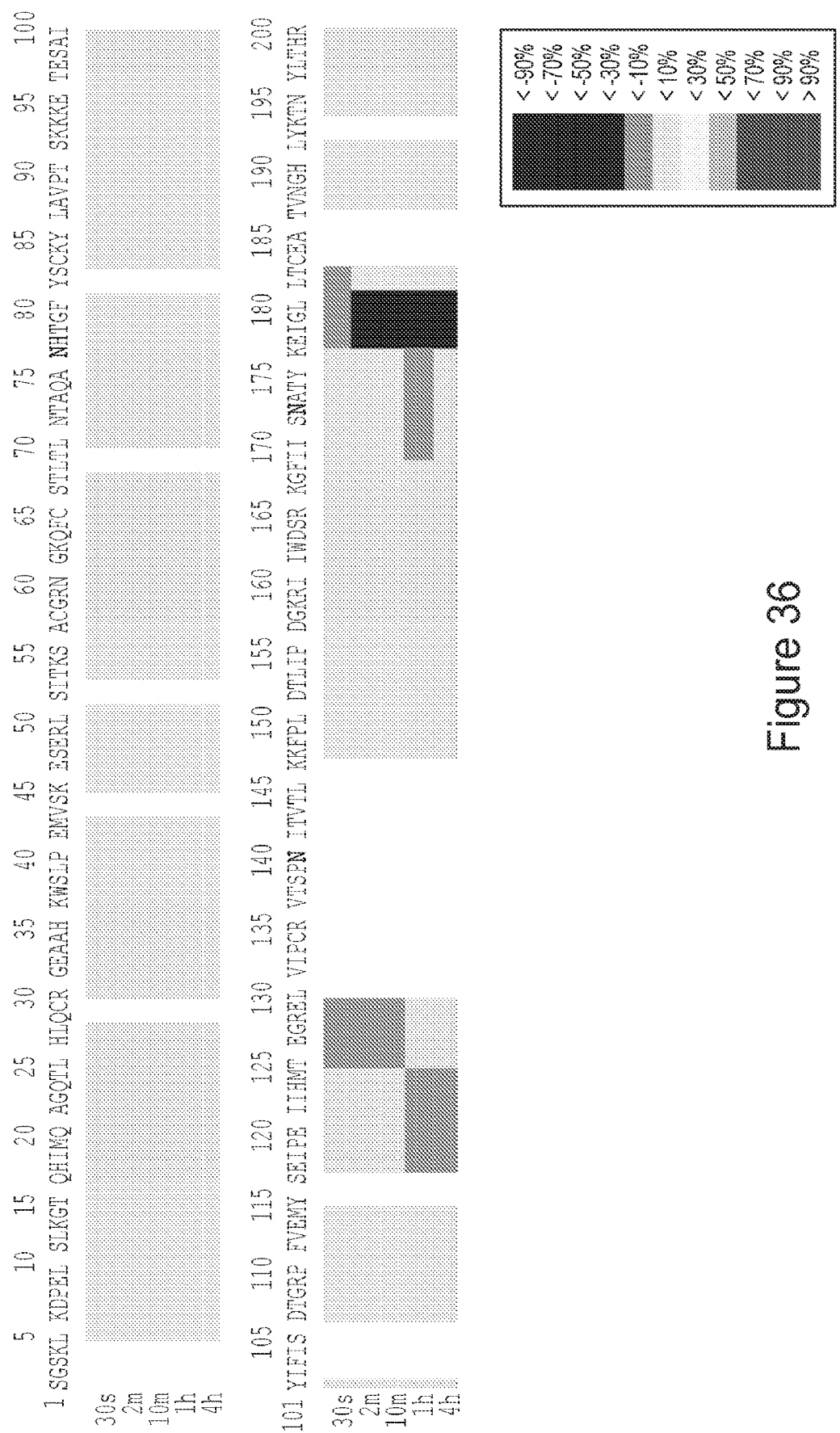
FIG. 36 shows exemplary results depicting a differential heat map comparing hydrogen/deuterium exchange of human sFlt-1 alone to that of human sFlt-1 and anti-Flt-1 antibody (21B3) mixture. Grey: no deuterium protection; blue: deuterium protection upon Fab binding.
Figure 36:
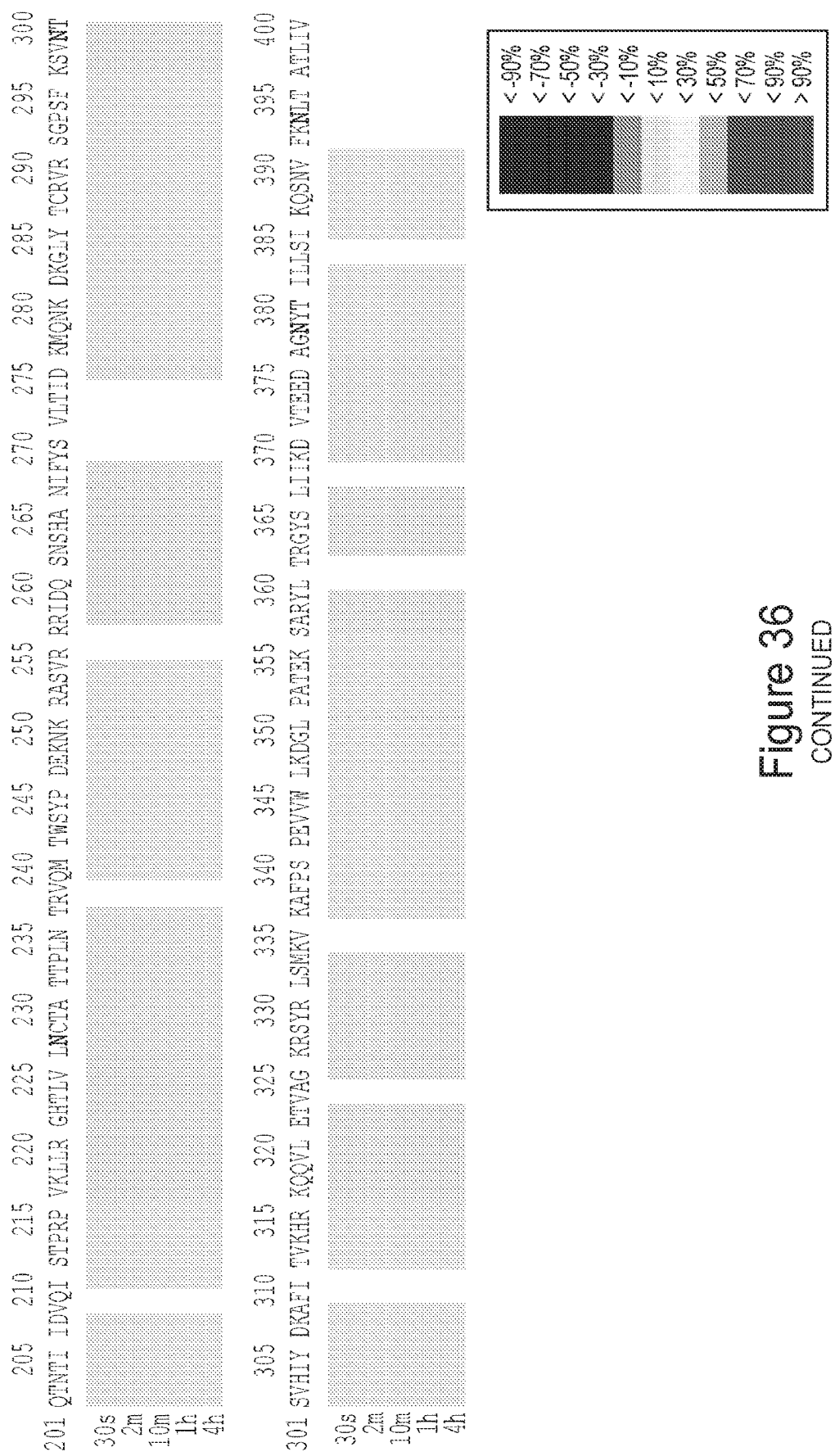
Figure 36:
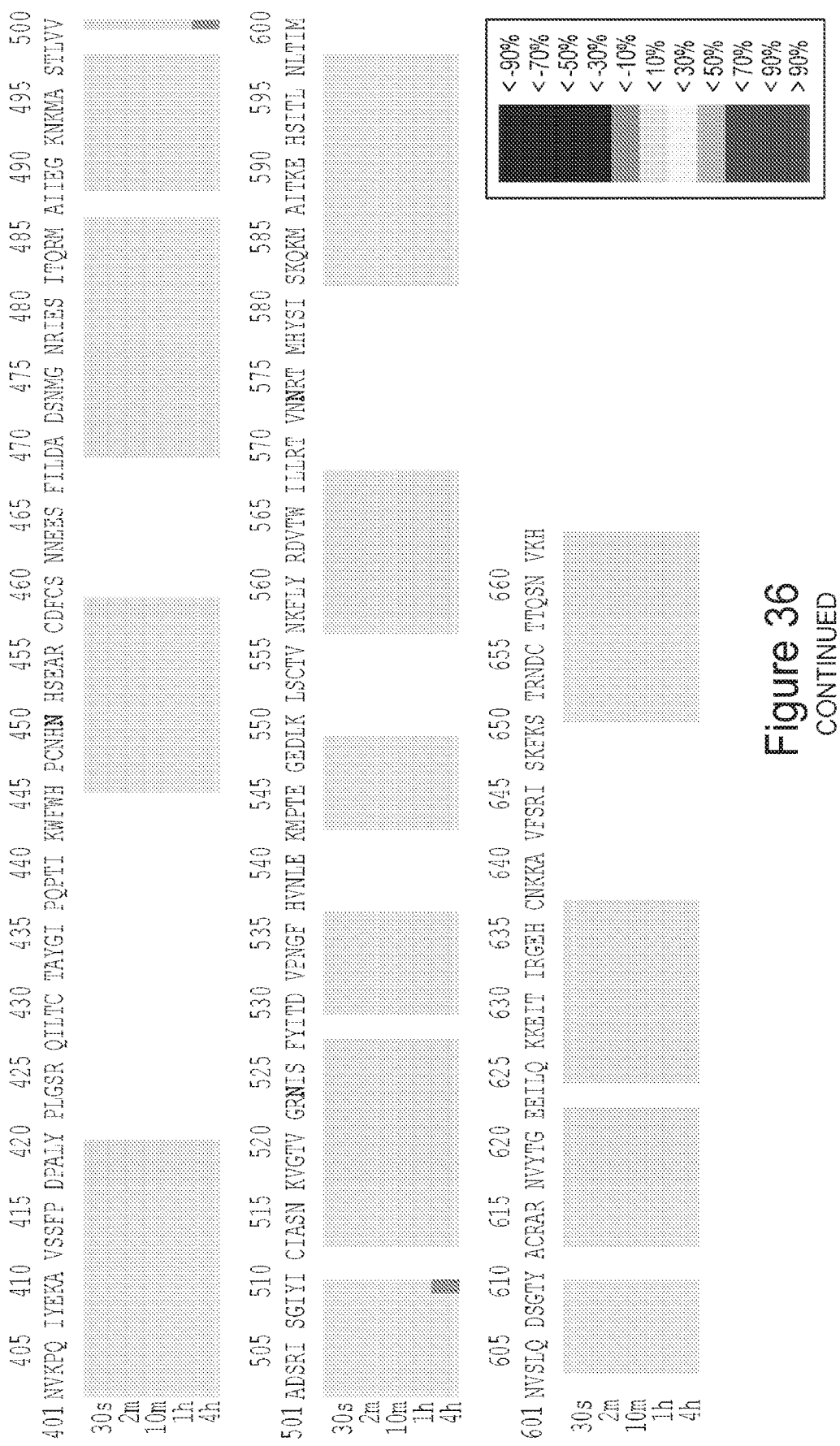
Figure 37:
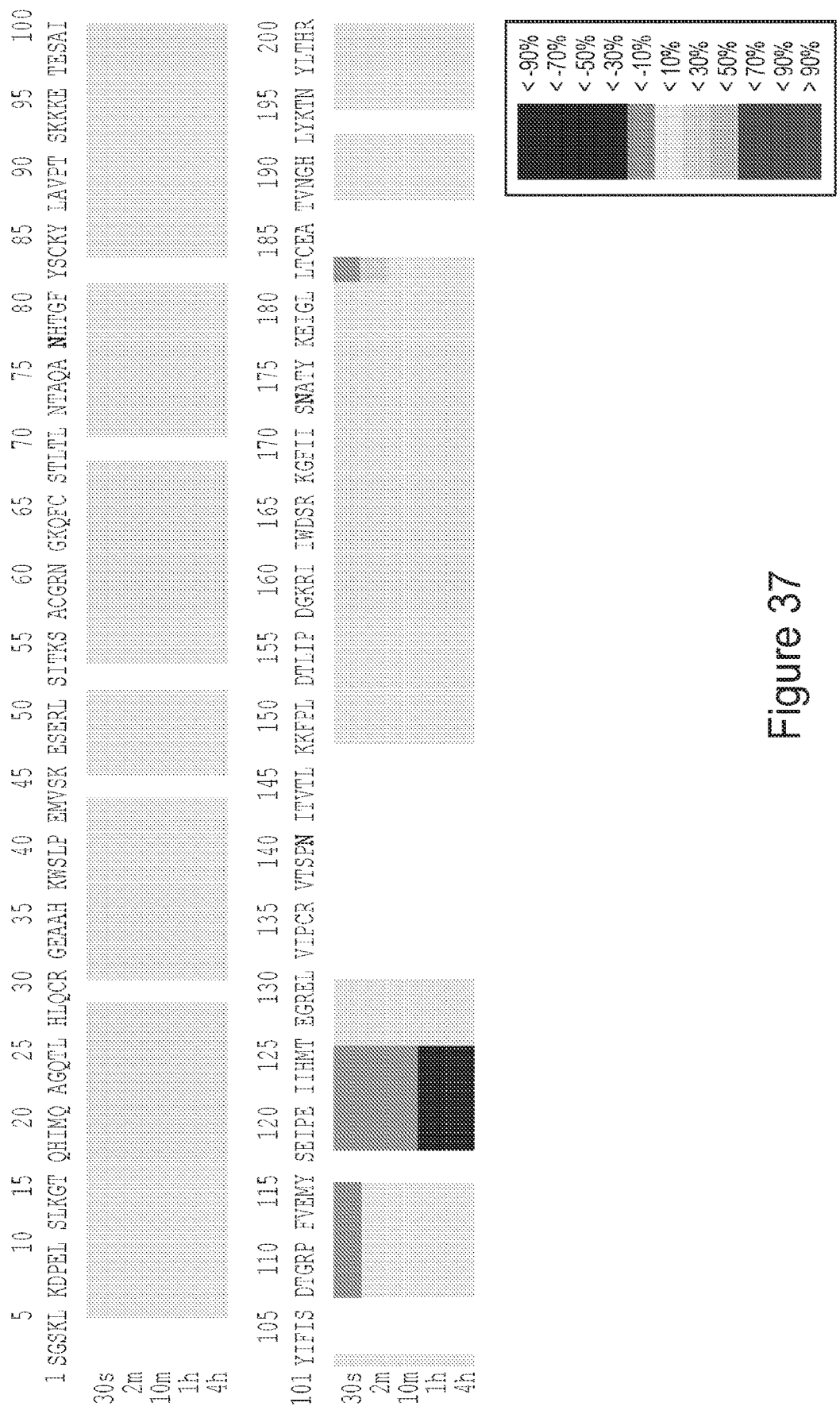
FIG. 37 shows exemplary results depicting a differential heat map comparing hydrogen/deuterium exchange of human sFlt-1 alone to that of human sFlt-1 and anti-Flt-1 antibody (21C6) mixture. Grey: no deuterium protection; blue: deuterium protection upon Fab binding.
Figure 37:
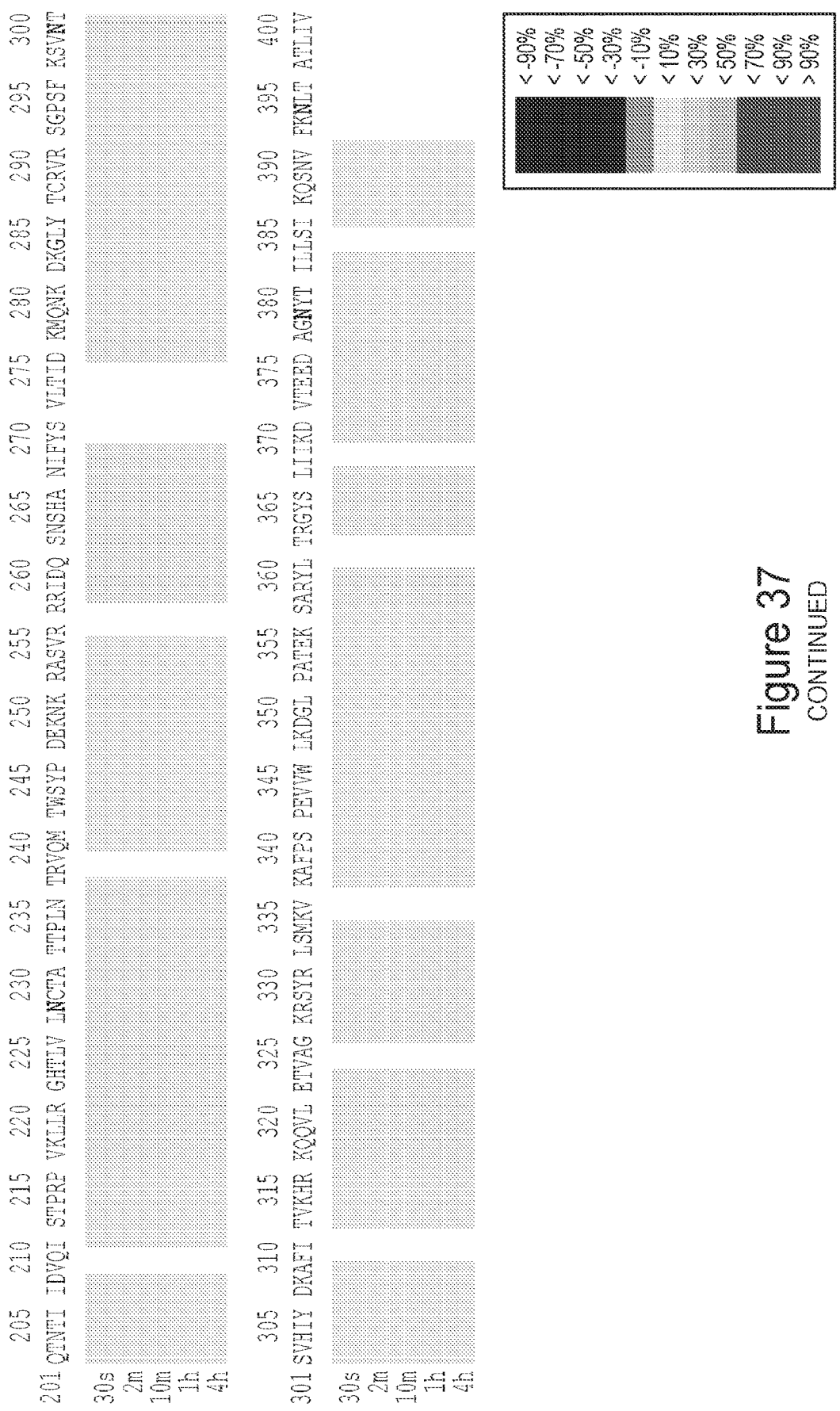
Figure 37:
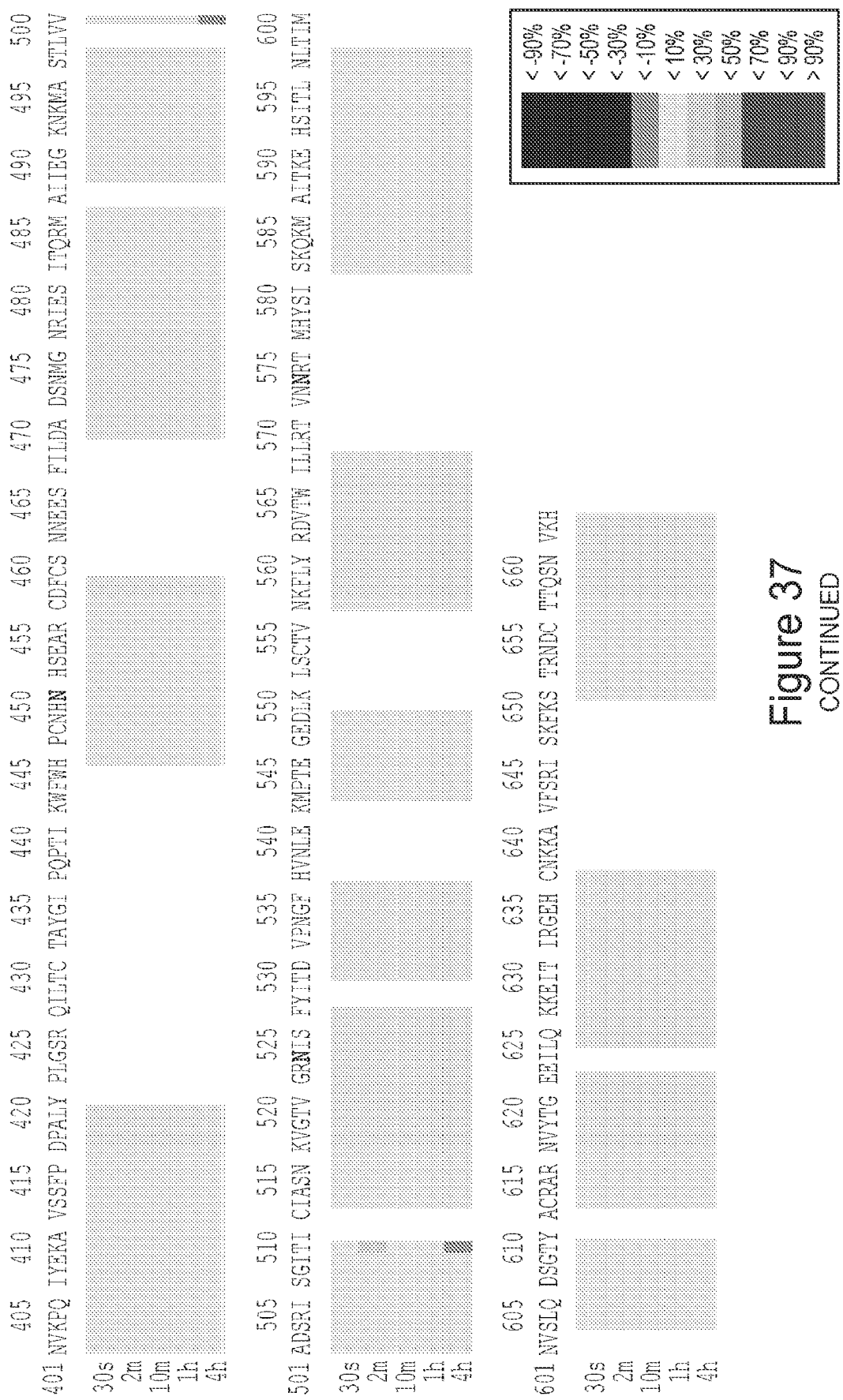
Figure 38A:
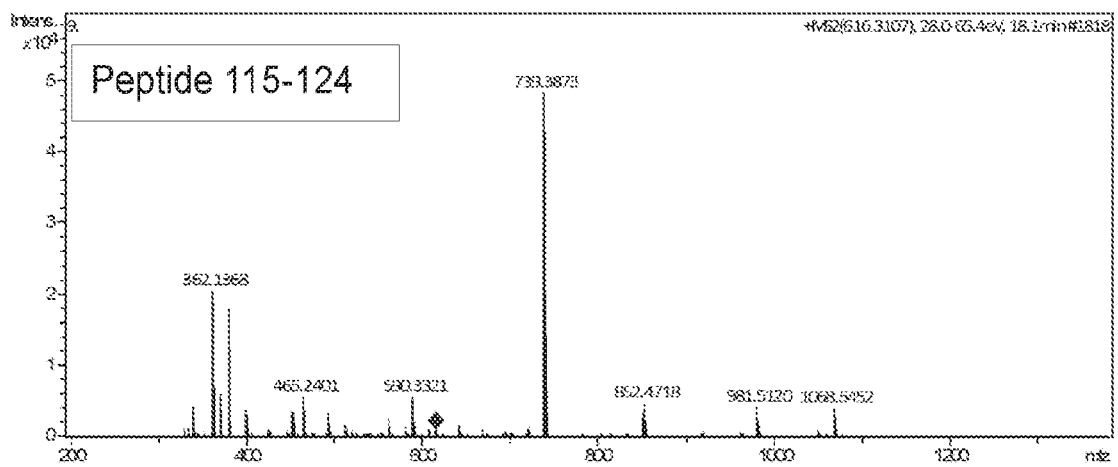
Figure 38B:
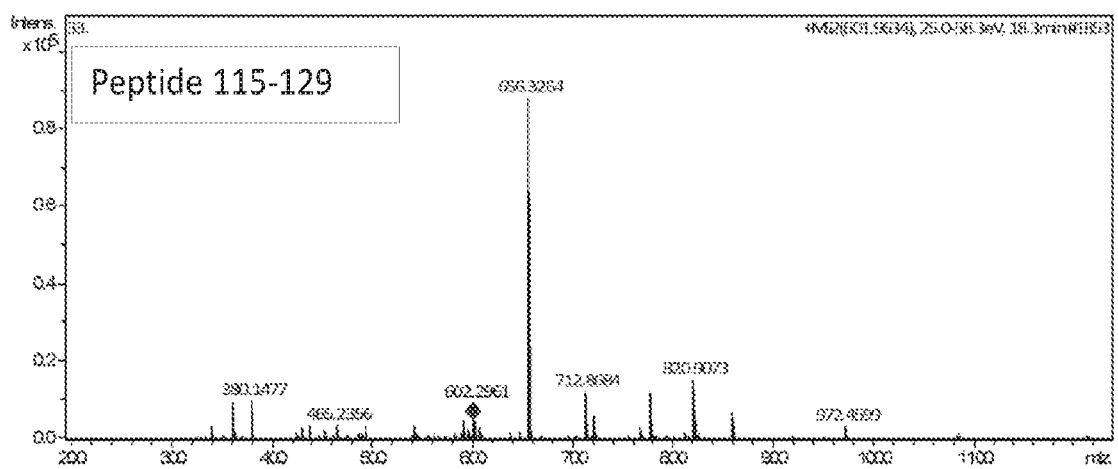
Figure 38C:
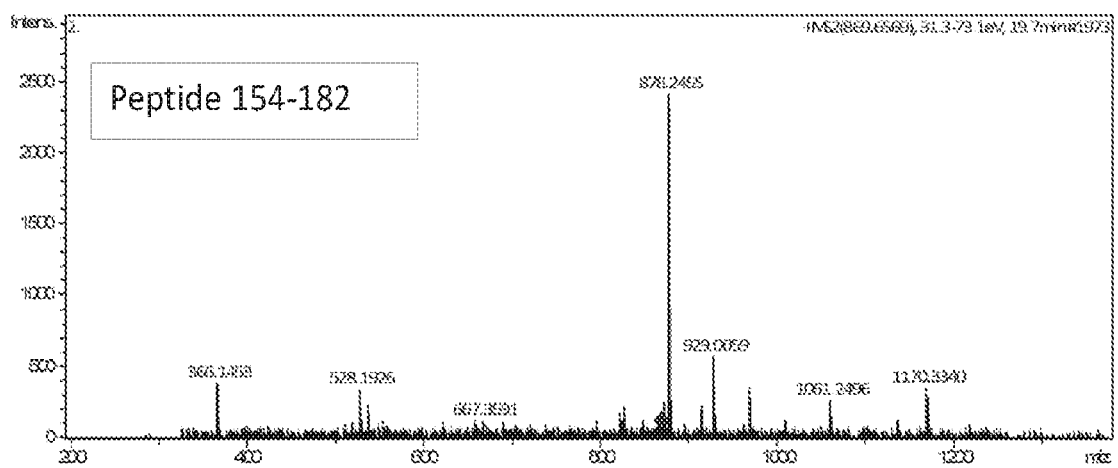
Figure 38D:
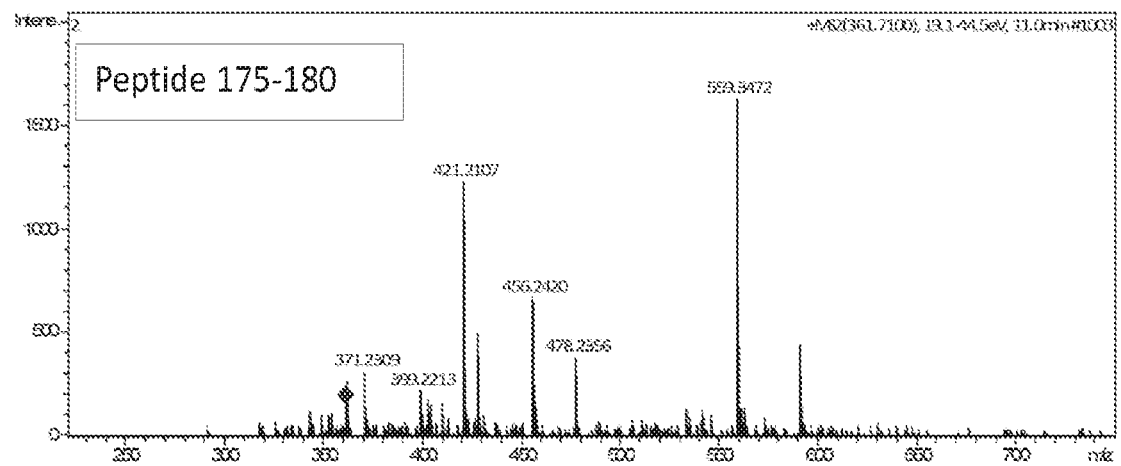
Figure 38E:
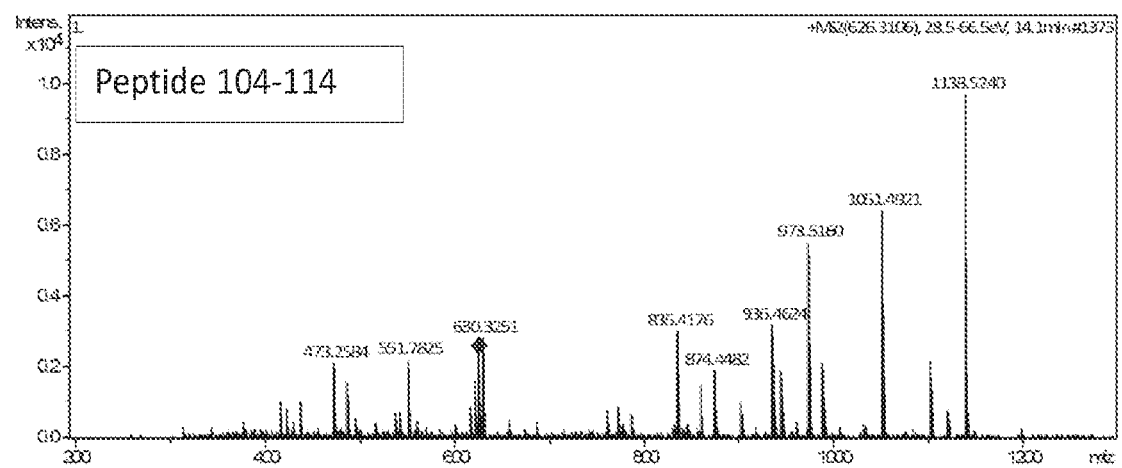

Native human sFlt-1 was incubated in deuterium oxide either alone or in complex with either anti-human sFlt-1 mAb (21B3) or anti-human sFlt-1 mAb (21C6). The deuterium exchange was carried at room temperature for 0 sec, 30 sec, 2 min, 10 min, 60 min and 240 min. The exchange reaction was quenched by low pH and the proteins were digested with pepsin. The deuterium levels at the identified peptides were monitored from the mass shift on LC-MS. The deuterium buildup curves over exchange time for all the peptides were plotted. While most of human sFlt-1 peptides displayed identical or similar deuterium levels with and without anti-human sFlt-1 mAbs (21B3 and 21C6), several peptide segments had significantly decreased deuterium incorporation upon mAb 21B3 or mAb 21C6 binding. Residues 117-129 (corresponding to amino acids 141-153 of SEQ ID NO:90) and 169-182 (corresponding to amino acids 193-206 of SEQ ID NO:90) experienced strong deuterium protection upon binding to anti-human sFlt-1 mAb 21B3, whereas residues 106-114 (corresponding to amino acids 130-138 of SEQ ID NO:90) and 117-124 (corresponding to amino acids 141-148 of SEQ ID NO:90) experienced strong deuterium protection upon binding to anti-human sFlt-1 mAb 21C6. These strongly protected regions were assigned as the epitope peptides for anti-human sFlt-1 mAbs (21B3 and 21C6) and highlighted in blue in the differential heat map shown in FIG. 36 and FIG. 37. The MS/MS spectra for identified peptides containing amino acid residues from epitope regions are shown in FIG. 38A-38E. Peptide 115-124 corresponds to amino acids 139-148 of SEQ ID NO:90; peptide 115-129 corresponds to amino acids 139-153 of SEQ ID NO:90; peptide 154-182 corresponds to amino acids 178-206 of SEQ ID NO:90; peptide 175-180 corresponds to amino acids 119-204 of SEQ ID NO:90; and peptide 104-114 corresponds to amino acids 128-138 of SEQ ID NO:90.

CONCLUSION 85.2% sequence coverage was achieved for human sFlt-1. Residues 117-129 and 169-180 experienced strong deuterium protection upon binding to anti-human sFlt-1 mAb 21B3, whereas residues 106-114 and 117-124 experienced strong deuterium protection upon binding to anti-human sFlt-1 mAb 21C6. These strongly protected regions were assigned as the epitope peptides for the corresponding anti-human sFlt-1 mAb.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

TABLE 13

```
Human Flt-1 amino acid sequence isoform 1 (NP_002010.2
GI:156104876; SEQ ID NO: 90)
    1   MVSYWDTGVL LCALLSCLLL TGSSSGSKLK DPELSLKGTQ HIMQAGQTLH LQCRGEAAHK

61   WSLPEMVSKE SERLSITKSA CGRNGKQFCS TLTLNTAQAN HTGFYSCKYL AVPTSKKKET

121   ESAIYIFISD TGRPFVEMYS EIPEIIHMTE GRELVIPCRV TSPNITVTLK KFPLDTLIPD

181   GKRIIWDSRK GFIISNATYK EIGLLTCEAT VNGHLYKTNY LTHRQTNTII DVQISTPRPV

241   KLLRGHTLVL NCTATTPLNT RVQMTWSYPD EKNKRASVRR RIDQSNSHAN IFYSVLTIDK

301   MQNKDKGLYT CRVRSGPSFK SVNTSVHIYD KAFITVKHRK QQVLETVAGK RSYRLSMKVK

361   AFPSPEVVWL KDGLPATEKS ARYLTRGYSL IIKDVTEEDA GNYTILLSIK QSNVFKNLTA

421   TLIVNVKPQI YEKAVSSFPD PALYPLGSRQ ILTCTAYGIP QPTIKWFWHP CNHNHSEARC

481   DFCSNNEESF ILDADSNMGN RIESITQRMA IIEGKNKMAS TLVVADSRIS GIYICIASNK

541   VGTVGRNISF YITDVPNGFH VNLEKMPTEG EDLKLSCTVN KFLYRDVTWI LLRTVNNRTM

601   HYSISKQKMA ITKEHSITLN LTIMNVSLQD SGTYACRARN VYTGEEILQK KEITIRDQEA

661   PYLLRNLSDH TVAISSSTTL DCHANGVPEP QITWFKNNHK IQQEPGIILG PGSSTLFIER

721   VTEEDEGVYH CKATNQKGSV ESSAYLTVQG TSDKSNLELI TLTCTCVAAT LFWLLLTLFI

781   RKMKRSSSEI KTDYLSIIMD PDEVPLDEQC ERLPYDASKW EFARERLKLG KSLGRGAFGK

841   VVQASAFGIK KSPTCRTVAV KMLKEGATAS EYKALMTELK ILTHIGHHLN VVNLLGACTK

901   QGGPLMVIVE YCKYGNLSNY LKSKRDLFFL NKDAALHMEP KKEKMEPGLE QGKKPRLDSV

961   TSSESFASSG FQEDKSLSDV EEEEDSDGFY KEPITMEDLI SYSFQVARGM EFLSSRKCIH

1021   RDLAARNILL SENNVVKICD FGLARDIYKN PDYVRKGDTR LPLKWMAPES IFDKIYSTKS

1081   DVWSYGVLLW EIFSLGGSPY PGVQMDEDFC SRLREGMRMR APEYSTPEIY QIMLDCWHRD

1141   PKERPRFAEL VEKLGDLLQA NVQQDGKDYI PINAILTGNS GFTYSTPAFS EDFFKESISA

1201   PKFNSGSSDD VRYVNAFKFM SLERIKTFEE LLPNATSMFD DYQGDSSTLL ASPMLKRFTW

1261   TDSKPKASLK IDLRVTSKSK ESGLSDVSRP SFCHSSCGHV SEGKRRFTYD HAELERKIAC

1321   CSPPPDYNSV VLYSTPPI

Human Flt-1 amino acid sequence, isoform X1 (XP_011533316.1
GI:767977511; SEQ ID NO: 91)
    1   MVSYWDTGVL LCALLSCLLL TGSSSGSKLK DPELSLKGTQ HIMQAGQTLH LQCRGEAAHK

61   WSLPEMVSKE SERLSITKSA CGRNGKQFCS TLTLNTAQAN HTGFYSCKYL AVPTSKKKET

121   ESAIYIFISD TGRPFVEMYS EIPEIIHMTE GRELVIPCRV TSPNITVTLK KFPLDTLIPD

181   GKRIIWDSRK GFIISNATYK EIGLLTCEAT VNGHLYKTNY LTHRQTNTII DVQISTPRPV

241   KLLRGHTLVL NCTATTPLNT RVQMTWSYPD EKNKRASVRR RIDQSNSHAN IFYSVLTIDK

301   MQNKDKGLYT CRVRSGPSFK SVNTSVHIYD KAFITVKHRK QQVLETVAGK RSYRLSMKVK

361   AFPSPEVVWL KDGLPATEKS ARYLTRGYSL IIKDVTEEDA GNYTILLSIK QSNVFKNLTA

421   TLIVNVKPQI YEKAVSSFPD RALYPLGSRQ ILTCTAYGIP QPTIKWFWHP CNHNHSEARC
```

TABLE 13-continued

```
481   DFCSNNEESF ILDADSNMGN RIESITQRMA IIEGKNKMAS TLVVADSRIS GIYICIASNK

541   VGTVGRNISF YITDVPNGFH VNLEKMPTEG EDLKLSCTVN KFLYRDVTWI LLRTVNNRTM

601   HYSISKQKMA ITKEHSITLN LTIMNVSLQD SGTYACRARN VYTGEEILQK KEITIRDQEA

661   PYLLRNLSDH TVAISSSTTL DCHANGVPEP QITWFKNNHK IQQEPDADPH IQKADCTFFF
```

Human Flt-1 amino acid sequence, isoform 2 precursor (NP_001153392.1
GI:229892220; SEQ ID NO: 92)
```
  1   MVSYWDTGVL LCALLSCLLL TGSSSGSKLK DPELSLKGTQ HIMQAGQTLH LQCRGEAAHK

61   WSLPEMVSKE SERLSITKSA CGRNGKQFCS TLTLNTAQAN HTGFYSCKYL AVPTSKKKET

121   ESAIYIFISD TGRPFVEMYS EIPEIIHMTE GRELVIPCRV TSPNITVTLK KFPLDTLIPD

181   GKRIIWDSRK GFIISNATYK EIGLLTCEAT VNGHLYKTNY LTHRQTNTII DVQISTPRPV

241   KLLRGHTLVL NCTATTPLNT RVQMTWSYPD EKNKRASVRR RIDQSNSHAN IFYSVLTIDK

301   MQNKDKGLYT CRVRSGPSFK SVNTSVHIYD KAFITVKHRK QQVLETVAGK RSYRLSMKVK

361   AFPSPEVVWL KDGLPATEKS ARYLTRGYSL IIKDVTEEDA GNYTILLSIK QSNVFKNLTA

421   TLIVNVKPQI YEKAVSSFPD RALYPLGSRQ ILTCTAYGIP QPTIKWFWHP CNHNHSEARC

481   DFCSNNEESF ILDADSNMGN RIESITQRMA IIEGKNKMAS TLVVADSRIS GIYICIASNK

541   VGTVGRNISF YITDVPNGFH VNLEKMPTEG EDLKLSCTVN KFLYRDVTWI LLRTVNNRTM

601   HYSISKQKMA ITKEHSITLN LTIMNVSLQD SGTYACRARN VYTGEEILQK KEITIRGEHC

661   NKKAVFSRIS KFKSTRNDCT TQSNVKH
```

Human Flt-1 amino acid sequence, isoform 3 precursor (NP_001153502.1
GI:229892300; SEQ ID NO: 93)
```
  1   MVSYWDTGVL LCALLSCLLL TGSSSGSKLK DPELSLKGTQ HIMQAGQTLH LQCRGEAAHK

61   WSLPEMVSKE SERLSITKSA CGRNGKQFCS TLTLNTAQAN HTGFYSCKYL AVPTSKKKET

121   ESAIYIFISD TGRPFVEMYS EIPEIIHMTE GRELVIPCRV TSPNITVTLK KFPLDTLIPD

181   GKRIIWDSRK GFIISNATYK EIGLLTCEAT VNGHLYKTNY LTHRQTNTII DVQISTPRPV

241   KLLRGHTLVL NCTATTPLNT RVQMTWSYPD EKNKRASVRR RIDQSNSHAN IFYSVLTIDK

301   MQNKDKGLYT CRVRSGPSFK SVNTSVHIYD KAFITVKHRK QQVLETVAGK RSYRLSMKVK

361   AFPSPEVVWL KDGLPATEKS ARYLTRGYSL IIKDVTEEDA GNYTILLSIK QSNVFKNLTA

421   TLIVNVKPQI YEKAVSSFPD RALYPLGSRQ ILTCTAYGIP QPTIKWFWHP CNHNHSEARC

481   DFCSNNEESF ILDADSNMGN RIESITQRMA IIEGKNKMAS TLVVADSRIS GIYICIASNK

541   VGTVGRNISF YITDVPNGFH VNLEKMPTEG EDLKLSCTVN KFLYRDVTWI LLRTVNNRTM

601   HYSISKQKMA ITKEHSITLN LTIMNVSLQD SGTYACRARN VYTGEEILQK KEITIRDQEA

661   PYLLRNLSDH TVAISSSTTL DCHANGVPEP QITWFKNNHK IQQEPELYTS TSPSSSSSSP

721   LSSSSSSSSS SSS
```

Human Flt-1 amino acid sequence, isoform 4 precursor (NP_001153503.1
GI:229892302; SEQ ID NO: 94)
```
  1   MVSYWDTGVL LCALLSCLLL TGSSSGSKLK DPELSLKGTQ HIMQAGQTLH LQCRGEAAHK

61   WSLPEMVSKE SERLSITKSA CGRNGKQFCS TLTLNTAQAN HTGFYSCKYL AVPTSKKKET

121   ESAIYIFISD TGRPFVEMYS EIPEIIHMTE GRELVIPCRV TSPNITVTLK KFPLDTLIPD

181   GKRIIWDSRK GFIISNATYK EIGLLTCEAT VNGHLYKTNY LTHRQTNTII DVQISTPRPV

241   KLLRGHTLVL NCTATTPLNT RVQMTWSYPD EKNKRASVRR RIDQSNSHAN IFYSVLTIDK

301   MQNKDKGLYT CRVRSGPSFK SVNTSVHIYD KAFITVKHRK QQVLETVAGK RSYRLSMKVK

361   AFPSPEVVWL KDGLPATEKS ARYLTRGYSL IIKDVTEEDA GNYTILLSIK QSNVFKNLTA

421   TLIVNVKPQI YEKAVSSFPD RALYPLGSRQ ILTCTAYGIP QPTIKWFWHP CNHNHSEARC
```

TABLE 13-continued

```
481 DFCSNNEESF ILDADSNMGN RIESITQRMA IIEGKNKLPP ANSSFMLPPT SFSSNYFHFL

541 P
```

TABLE 14

Fc Region Sequence (SEQ ID NO: 104)

```
209 TKVDKKVEPK SCDKTHTCPP CPAPELLGGP SVFLFPPKPK DTLMISRTPE VTCVVVDVSH

269 EDPEVKFNWY VDGVEVHNAK TKPREEQYNS TYRVVSVLTV LHQDWLNGKE YKCKVSNKAL

329 PAPIEKTISK AKGQPREPQV YTLPPSREEM TKNQVSLTCL VKGFYPSDIA VEWESNGQPE

389 NNYKTTPPVL DSDGSFFLYS KLTVDKSRWQ QGNVFSCSVM HEALHNHYTQ KSLSLSPG
```

We claim:

1. An anti-Flt-I antibody or antigen-binding fragment thereof, comprising:
   (a) a VL CDR1 defined by the amino acid sequence of SEQ ID NO:21, a VL CDR2 defined by the amino acid sequence of SEQ ID NO:24, a VL CDR3 defined by the amino acid sequence of SEQ ID NO: 26, a VH CDR1 defined by the amino acid sequence of SEQ ID NO: 2, a VH CDR2 defined by the amino acid sequence of SEQ ID NO: 6, and a VH CDR3 defined by the amino acid sequence of SEQ ID NO: 16;
   (b) a VL CDR1 defined by the amino acid sequence of SEQ ID NO:21, a VL CDR2 defined by the amino acid sequence of SEQ ID NO:24, a VL CDR3 defined by the amino acid sequence of SEQ ID NO: 27, a VH CDR1 defined by the amino acid sequence of SEQ ID NO: 2, a VH CDR2 defined by the amino acid sequence of SEQ ID NO: 7, and a VH CDR3 defined by the amino acid sequence of SEQ ID NO: 17;
   (c) a VL CDR1 defined by the amino acid sequence of SEQ ID NO:21, a VL CDR2 defined by the amino acid sequence of SEQ ID NO:24, a VL CDR3 defined by the amino acid sequence of SEQ ID NO: 26, a VH CDR1 defined by the amino acid sequence of SEQ ID NO: 3, a VH CDR2 defined by the amino acid sequence of SEQ ID NO: 12, and a VH CDR3 defined by the amino acid sequence of SEQ ID NO: 17;
   (d) a VL CDR1 defined by the amino acid sequence of SEQ ID NO:21, a VL CDR2 defined by the amino acid sequence of SEQ ID NO:24, a VL CDR3 defined by the amino acid sequence of SEQ ID NO: 28, a VH CDR1 defined by the amino acid sequence of SEQ ID NO: 2, a VH CDR2 defined by the amino acid sequence of SEQ ID NO: 8, and a VH CDR3 defined by the amino acid sequence of SEQ ID NO: 17; or
   (e) a VL CDR1 defined by the amino acid sequence of SEQ ID NO:21, a VL CDR2 defined by the amino acid sequence of SEQ ID NO:24, a VL CDR3 defined by the amino acid sequence of SEQ ID NO: 32, a VH CDR1 defined by the amino acid sequence of SEQ ID NO: 3, a VH CDR2 defined by the amino acid sequence of SEQ ID NO: 12, and a VH CDR3 defined by the amino acid sequence of SEQ ID NO: 17.

2. The antibody or antigen-binding fragment thereof of claim 1, wherein the anti-Flt-1 antibody or antigen-binding fragment thereof comprises:
   a VL CDR1 defined by an amino acid sequence of SEQ ID NO:21,
   a VL CDR2 defined by an amino acid sequence of SEQ ID NO:24;
   a VL CDR3 defined by an amino acid sequence of SEQ ID NO: 26;
   a VH CDR1 defined by an amino acid sequence of SEQ ID NO: 2,
   a VH CDR2 defined by an amino acid sequence of SEQ ID NO: 6, and
   a VH CDR3 defined by an amino acid sequence of SEQ ID NO: 16.

3. The antibody or antigen-binding fragment thereof of claim 1, wherein the anti-Flt-1 antibody or antigen-binding fragment thereof comprises:
   a VL CDR1 defined by an amino acid sequence of SEQ ID NO:21,
   a VL CDR2 defined by an amino acid sequence of SEQ ID NO:24;
   a VL CDR3 defined by an amino acid sequence of SEQ ID NO: 27;
   a VH CDR1 defined by an amino acid sequence of SEQ ID NO: 2,
   a VH CDR2 defined by an amino acid sequence of SEQ ID NO: 7, and
   a VH CDR3 defined by an amino acid sequence of SEQ ID NO: 17.

4. The antibody or antigen-binding fragment thereof of claim 1, wherein the anti-Flt-1 antibody or antigen-binding fragment thereof comprises:
   a VL CDR1 defined by an amino acid sequence of SEQ ID NO:21,
   a VL CDR2 defined by an amino acid sequence of SEQ ID NO:24;
   a VL CDR3 defined by an amino acid sequence of SEQ ID NO: 26;
   a VH CDR1 defined by an amino acid sequence of SEQ ID NO: 3,
   a VH CDR2 defined by an amino acid sequence of SEQ ID NO: 12, and
   a VH CDR3 defined by an amino acid sequence of SEQ ID NO: 17.

5. The antibody or antigen-binding fragment thereof of claim 1, wherein the anti-Flt-1 antibody or antigen-binding fragment thereof comprises:
   a VL CDR1 defined by an amino acid sequence of SEQ ID NO:21,
   a VL CDR2 defined by an amino acid sequence of SEQ ID NO:24;
   a VL CDR3 defined by an amino acid sequence of SEQ ID NO: 28;
   a VH CDR1 defined by an amino acid sequence of SEQ ID NO: 2,
   a VH CDR2 defined by an amino acid sequence of SEQ ID NO: 8, and
   a VH CDR3 defined by an amino acid sequence of SEQ ID NO: 17.

6. The antibody or antigen-binding fragment thereof of claim 1, wherein the antibody or antigen-binding fragment thereof is selected from the group consisting of IgG, F(ab')₂, F(ab)₂, Fab', Fab, ScFvs, diabodies, triabodies and tetrabodies, optionally wherein the antibody or antigen-binding fragment thereof is IgG, optionally wherein the antibody or antigen-binding fragment thereof is IgG1.

7. The antibody or antigen-binding fragment thereof of claim 1, wherein the antibody or antigen-binding fragment thereof is a monoclonal antibody,
wherein the monoclonal antibody contains a human Fc region,
wherein the Fc region contains one or more mutations that enhance the binding affinity
between the Fc region and the FcRn receptor such that the in vivo half-life of the antibody is prolonged, and
wherein the Fc region contains one or more mutations at positions corresponding to Leu 234, Leu 235 and/or Gly 237 of human IgG1.

8. The antibody or antigen-binding fragment thereof of claim 1, wherein the antibody or antigen-binding fragment thereof does not bind to VEGFR2 and/or VEGFR3.

9. The antibody or antigen-binding fragment thereof of claim 1, wherein the antibody or antigen-binding fragment thereof does not bind to a mouse or monkey Flt-1.

10. A pharmaceutical composition comprising the antibody or antigen-binding fragment thereof of claim 1 and a pharmaceutically acceptable carrier.

11. The antibody or antigen-binding fragment thereof of claim 1, wherein the anti-Flt-1 antibody or antigen-binding fragment thereof comprises:

(a) a light chain variable (VL) region comprising an amino acid sequence having at least 90% identity to SEQ ID NO: 60 and a heavy chain variable (VH) region comprising an amino acid sequence having at least 90% identity SEQ ID NO: 45, (b) a light chain comprising an amino acid sequence having at least 90% identity to of SEQ ID NO: 76 and a heavy chain comprising an amino acid sequence having at least 90% identity to SEQ ID NO: 71, (c) a light chain comprising an amino acid sequence having at least 90% identity to SEQ ID NO: 85 and a heavy chain comprising an amino acid sequence having at least 90% identity to SEQ ID NO:72, (d) a light chain comprising an amino acid sequence having at least 90% identity to SEQ ID NO: 84 and (ii) a heavy chain comprising an amino acid sequence having at least 90% identity to SEQ ID NO:71, (e) a light chain comprising an amino acid sequence having at least 90% identity to SEQ ID NO: 86 and a heavy chain comprising an amino acid sequence having at least 90%/0 identity to SEQ ID NO:73, or (f) a light chain comprising an amino acid sequence having at least 90% identity to SEQ ID NO: 83 and a heavy chain comprising an amino acid sequence having at least 90% identity to SEQ ID NO:70.

\* \* \* \* \*